US006057299A

United States Patent [19]
Henderson

[11] Patent Number: 6,057,299
[45] Date of Patent: *May 2, 2000

[54] TISSUE-SPECIFIC ENHANCER ACTIVE IN PROSTATE

[75] Inventor: Daniel R. Henderson, Palo Alto, Calif.

[73] Assignee: Calydon, Inc., Sunnyvale, Calif.

[*] Notice: This patent is subject to a terminal disclaimer.

[21] Appl. No.: 08/721,690

[22] Filed: Sep. 27, 1996

Related U.S. Application Data

[63] Continuation-in-part of application No. 08/380,916, Jan. 30, 1995, Pat. No. 5,648,478, which is a continuation-in-part of application No. 08/182,247, Jan. 13, 1994, Pat. No. 5,830,686, and a continuation-in-part of application No. 08/669,753, Jun. 26, 1996, Pat. No. 5,871,726, which is a continuation-in-part of application No. 08/495,034, Jun. 27, 1995, Pat. No. 5,698,443.

[51] Int. Cl.[7] ..................................................... A61K 48/00
[52] U.S. Cl. .......................... 514/44; 536/23.1; 536/24.1; 435/69.1; 435/320.1; 435/325; 435/455; 435/458; 424/93.21
[58] Field of Search .............................. 435/320.1, 172.3, 435/325; 514/2, 44; 424/93.21; 536/23.1, 24.1; 935/51, 61, 63, 455, 458, 69.1

[56] References Cited

U.S. PATENT DOCUMENTS

| | | | |
|---|---|---|---|
| 4,683,202 | 7/1987 | Mullis | 435/91 |
| 5,698,443 | 12/1997 | Henderson et al. | 435/320.1 |

FOREIGN PATENT DOCUMENTS

| | | |
|---|---|---|
| WO 91/14696 | 10/1991 | WIPO. |
| WO 91/16024 | 10/1991 | WIPO. |
| WO 91/17424 | 11/1991 | WIPO. |
| WO 91/17761 | 11/1991 | WIPO. |
| WO 91/17773 | 11/1991 | WIPO. |
| WO 92/05250 | 4/1992 | WIPO. |
| WO 92/06180 | 4/1992 | WIPO. |
| WO 92/13570 | 8/1992 | WIPO. |
| WO 94/03594 | 2/1994 | WIPO. |
| WO 94/28152 | 12/1994 | WIPO. |

OTHER PUBLICATIONS

Allison, J. et al. "Tissue–specific and hormonal regulation of the genes for rat prostatic steroid–binding protein in transgenic mice" *Molecular and Cellular Biology*(1989)9(5):2254–2257.

Banas et al. "Analysis of the promoter of the human prostatic acid phosphatase gene" *Biochimica et Biophysica Acta*(1994)1217:188–194.

Slawin et al. "Transgenic Studies: Evidence that a prostate–specific promoter acts by silencing inapporiate expression sites" *Journal of Urology*(1992)147(4 Suppl.):319A.

Taneja et al. "Construction of a prostate specific antigen promoter–driven gene transfer vector:a novel strategy for target specific gene therapy in prostate cancer" *Journal of Urology*(May 1994)151(5 Suppl.):491A.

Adair et al., "Targeted homologous recombination at the endogenous adenine phosphoribosyltransferase locus in Chinese hamster cells" *Proc. Natl. Acad. Sci. (USA)* (1989)86:4574–4578.

Allan et al., "Synergism between Steroid Response and Promoter Elements during Cell–free Transcription" *J. Biol. Chem.* (1991)226:5905–5910.

An et al., "Expression of bacterial β–galactosidase in animal cells" *Mol. Cell. Biol.* (1982) 2:1628–1632.

Bagchi et al., "Steroid Hormone–Dependent Interaction of Human Progesterone Receptor with its Target Enhancer Element" *Mol. Endocrinol.* (1988)2:1221–1229.

Beato, "Gene Regulation by Steroid Hormones" *Cell* (1989)56:335–344.

Behr et al., "Efficient gene transfer into mammalian primary endocrine cells with lipopolyamine–coated DNA" *Proc. Natl. Acad. Sci. (USA)* (1989)86:6982–6986.

Behringer et al., "Dwarf mice produced by genetic ablation of growth hormone–expressing cells" *Genes & Dev.* (1988) 2:453–461.

Bradshaw et al., "A Steroid Response Element can Function in the Absence of a Distal Promoter" *Mol. Endocrinol.* (1988) 2:1286–1993.

Brewster et al., "Gene therapy in urological oncology: principles, strategies and potential" *Eur. Urol.* (1994)25:177–182.

Brinster et al., "Introns increase transcriptional efficiency in transgenic mice" *Proc. Natl. Acad. Sci. (USA)* (1988) 85:836–840.

Capecchi, "Altering the Genome by Homologous Recombination" *Science* (1989) 244: 1288–1292.

Chaudhary et al., "Pseudomonas exotoxin contains a specific sequence at the carboxyl terminus that is required for cytotoxicity" *Proc. Natl. Acad. Sci. (USA)* (1990)87:308–312.

Cornetta et al., "No Retroviremia or Pathology in Long–Term Follow–Up of Monkeys Exposed to a Murine Amphotropic Retrovirus" *Hum. Gene Ther.* (1991) 2:215–219.

Dean et al., "Effects of Exogenous Amines on Mammalian Cells, will Particular Reference to Membrane Flow" *Biochem. J.* (1984) 217:27–40.

Dignam et al., "Accurate Transcription Initiation by RNA Polymerase II in a Soluble Extract From Isolated Mammalian Nuclei" *Nucl. Acids Res.* (1983) 11:1475–1489.

(List continued on next page.)

*Primary Examiner*—Bruce R. Campell
*Assistant Examiner*—Dave Trong Nguyen
*Attorney, Agent, or Firm*—Morrison & Foerster, LLP

[57] ABSTRACT

The invention provides a human prostate-specific transcriptional regulatory sequence, polynucleotide comprising such regulatory regions, toxin gene constructs wherein a toxin gene is expressed under the transcriptional control of a human prostate-specific transcriptional regulatory sequence, and methods for treating prostate disease using such toxin gene constructs.

34 Claims, 24 Drawing Sheets

OTHER PUBLICATIONS

Eckert et al., "DNA Polymerase Fidelity and the Polymerase Chain Reaction" *PCR Methods and Applications* (1991) 1:17–24.

Felgner et al. "Lipofection: A Highly Efficient, Lipid–Mediated DNA–Transfection Procedure" *Natl. Acad. Sci. USA* (1987) 84:7413–7417.

Frankel et al., "Selection and Characterization of Ricin Toxin A–Chain Mutations in *Saccharomyces cerevisiae*" *Mol. Cell. Biol.* (1989) 9:415–420.

Gao et al., "A Novel Cationic Liposome Reagent For Efficient Transfection of Mammalian Cells" *Biochem. Biophys. Res. Commun.* (1991) 179:280–285.

Ghadzizadeh et al., "Prostatic Origin of Metastases: Immunoperoxidase Localization of Prostate–Specific Antigen" *Urol. Int.* (1984) 39:9–12.

Gotoh et al., "New strategy of toxic gene therrapy for human prostate cancer cells" *J. Urol.* (1995) 153:308A (abstract No. 320).

Haddada et al., "Adenoviral Interleukin–2 Gene Transfer into P815 Tumor Cells Abrogates Tumorigenicity and Induces Antitumoral Immunity in Mice" *Human Gene Therapy* (1993) 4: 703–711.

Hamdy et al., "Circulating Prostate Specific Antigen–positive Cells Correlate with Metastatic Prostate Cancer" *Br. J. Urol.* (1992) 69:392–396.

Henttu et al., "cDNA coding for the entire human prostate specific antigen shows high homologies to the human tissue kallikrein genes" *Biochemical and Biophysical Research Communications* (1989) 160:903–910.

Ho et al., "Interactions Of Antigen–Sensitized Liposomes With Immobilized Antibody: A Homogenous Solid–Phase Immunoliposome Assay" *J. Immunol.* (1985) 134:4035–4040.

Hogan et al., Manipulating the Mouse Embryo: *A Laboratory Manual*, (1988) Cold Spring Harbor Laboratory. The title page and table of contents are included herewith.

Horoszewicz et al., "LNCaP Model of Human Prostatic Carcinoma" *Cancer Res.* (1983) 43:1809–1818.

Hwang et al., "Functional Domains of Pseudomonas Exotoxin Identified by Deletion Analysis of the gene Expressed in *E. Coli*" *Cell* (1987) 48:129–136.

Innis et al., eds., *PCR Protocols: A Guide to Methods and Applications*, (1990) Academic Press. The title page and table of contents are included herewith.

Johnson et al., "Targeting of Nonexpressed Genes in Embryonic Stem Cells via Homologous Recombination" *Science* (1989) 245:1234–1236.

Kolberg, "Gene–Transfer Virus Contaminant Linked To Monkey's Cancer" *J. NIH Res.* (1992) 4:43–44.

Kovarik et al., "Analysis of the Tissue–specific Promoter of the *MUC1* Gene" *J. Biol. Chem.* (1993) 268:9917–9926.

Lamb et al., "Nucleotide Sequence of Cloned cDNA Coding for Preproricin" *Eur. J. Biochem* (1985) 148:265–270.

Lemaigre et al., "Liver–specific Factor Binding to the Liver Promoter of a 6–Phosphofructo–2–kinase/Fructose–2, 6–bisphosphatase Gene" *J. Biol. Chem.* (1993) 268:19896–19905.

Litzinger et al., "Phosphatidylethanolamine liposomes: Drug Delivery, Gene Transfer and Immunodiagnostic Appications" *Biochem. Biophys. Acta* (1992) 1113:201–227.

Luke et al., "Human Androgen Receptor Binding to the Androgen Response Element of Prostate Specific Antigen" *J. Androl.* (1994) 15:41–51.

Lundwall, "Characterization of the Gene for Prostate–Specific Antigen, a Human Glandular Kallikrein" *Biochem. and Biophys. Res. Commun.* (1989) 161:1151–1159.

Lundwall et al., "Molecular Cloning of Human Prostate Specific Antigen cDNA" *FEBS Lett.* (1987) 214:317–322.

Mannino et al., "Liposome Mediated Gene Transfer" *Biotechniques* (1988) 6:682–690.

Mansour et al., "Disruption of the Proto–oncogene int–2 in Mouse Embryo–Derived Stem Cells: a General Strategy for Targeting Mutations to Non–Selectable Genes" *Nature* (1988) 336:348–352.

Mattila et al., "Fidelity of DNA Synthesis by the *Thermococcus litoralis* DNA Polymerase—an Extremely Heat Stable Enzyme with Proofreading Activity" *Nucleic Acids Res.* (1991) 19:4967–4973.

Maxwell et al., "Cloning, Sequence Determination, and Expression in Transfected Cells of the Coding Sequence for the tox 176 Attenuated Diphtheria Toxin A Chain" *Mol. Cell. Biol.* (1987) 7:1576–1579.

Maxwell et al., "Regulated Expression of Diphtheric Toxin A–Chain Gene Transfected into Human Cells: Possible Strategy for Inducing Cancer Cell Suicide" *Cancer Res.* (1986) 46:4660–4664.

Messing et al., "$P_o$ Promoter Directs Expression of Reporter and Toxin Genes to Schwann Cells of Transgenic Mice" *Neuron* (1992) 8:507–520.

Meyer et al., "Steroid hormone receptors compete for factors that mediate their enhancer function" *Cell* (1989) 57:433–442.

Miller et al., "Gene Transfer by Retrovirus Vectors Occurs Only in Cells that are Actively Replicating at the Time of Infection" *Mol. Cell. Biol.* (1990) 10: 4239–4242.

Mitchell et al., "Transcriptional Regulation in Mammalian Cells by Sequence–Specific DNA Binding Proteins" *Science* (1989) 245:371–378.

Mocellini et al., "Finasteride (MK–906) in the Treatment of Benign Prostatic Hyperphlasia" *The Prostate* (1993) 22:291–299.

Moss, Vaccinia virus: A tool for research and vaccine development (1991) 252:1662–1667.

Nabel et al., "Immunotherapy of Malignancy by in vivo Gene Transfer into Tumors" *Human Gene Therapy* (1992) 3:399–410. Note: pp. 400–401 are missing from the original document.

Nawaz et al., "Identification of Novel Steroid–Response Elements" *Gene Expr.* (1992) 2:39–47.

Nitsch et al., "The Distal Enhancer Implicated in the Developmental Regulation of the Tyrosine Amino Transferase Gene Is Bound by Liver–Specific and Ubiquitous Factors" *Mol. Cell. Biol.* (1993) 13:4494–4504.

Ozono et al., "The Vitamin D–responsive Element in the Human Osteocalcin Gene" *J. Biol. Chem.* (1990) 265:21881–21888.

Palmiter et al., "Cell Lineage Ablation in Transgenic Mice by Cell–Specific Expression of a Toxic Gene" *Cell* (1987) 50:435–443.

Papsidero et al., "Prostate Antigen: A Marker for Human Prostate Epithelial Cells" *J. Natl. Cancer Inst.* (1981) 66:37–42.

Pearson et al., "Improved Tools for Biological Sequence Comparison" *Proc. Natl. Acad. Sci. USA* (1988) 85:2444–2448.

Piatak et al., "Expression of Soluble and Fully Functional Ficin A Chain in *Escherichia coli* is Temperature–Sensitive" *J. Biol. Chem.* (1988) 263:4837–4843.

Redding et al., "Prostate Carcinoma Tumor Size in Rats Decrease after Administration of Antagonists of Luteinizing Hormore–releasing Hormone" *Proc. Natl. Acad. Sci.* (1982) 79:1273–1276.

Rhodes et al., "A Tissue–specific Enhancer Confers Pit–1–dependent Morphogen Inducibility and Autoregulation on the pit–1 Gene" *Genes Dev.* (1993) 7:913–932.

Rieger et al., eds., *Glossary of Genetics and Gytogenetics, Classical and Molecular*, 4th Ed., Springer–Verlag, Berlin, (1976) pp. 381–383.

Reigman et al., "Characterization of the Human Kallikrein Locus" *Genomics* (1992) 14:6–11.

Riegman et al., "Characterization of the Prostate–Specific Antigen Gene: a Novel Human Kallikrein–like Gene" *Biochem. Biophys. Res. Commun.* (1989) 159: 95–102.

Reigman et al., "The Promoter of the Prostate–specific Antigen Gene Containing a Functional Androgen Responsive Element" *Mol. Endocrinol.* (1991) 5:1921–1930.

Robertson, ed. *Teratocarcinomas and Embryonic Stem Cells: A Practical Approach*, , IRL Press, Washington, D.C., (1987). The title page and table of contents are included.

Roche et al., "A Consensus DNA–Binding Site for the Androgen Receptor" *Mol. Endocrinol.* (1992) 6:2229–2235.

Rosenfeld et al., "In vivo Transfer of the Human Cystic Fibrosis Transmembrane Conductance Regulator Gene to the Airway Epithelium" *Cell* (1992) 68: 143–155.

Rouet et al., "A Potent Enhancer Made of Clustered Liver–Specific Elements in the Transcription Control Sequences of Human α1–Microglobulin/Bikunin Gene" *J. Biol. Chem.* (1992) 267:20765–20773.

Sanda et al., "Gene Therapy for Urologic Cancer" *Urology* (1994) 44: 617–624.

Schuur et al., "Prostate–specific Antigen Expression is Regulated by an Upstream Enhancer" *J. Biol. Chem.* (1996) 271:7043–7051.

Schuur et al., "Chimeras of Herpes Simplex Viral VP16 and Jun are Oncogenic" *Cell Growth & Differentiation* (1993) 4:761–768.

Schwartzberg et al., "Germ–Line Transmission of a c–abl Mutation Produced by Targeted Gene Disruption in ES Cells" *Science* (1989) 246:799–803.

Siegall et al., "Functional Analysis of Domains II, Ib, and III of Pseudomonas Exotoxin" *J. Biol. Chem.* (1989) 264:14256–14261.

Taneja et al., "Construction of a Prostate Specific Antigen Promoter–Driven Gene Transfer Vector: a Novel Strategy for Target Specific Gene Therapy in Prostate Cancer" *Oncology* (1994) 491A, Abstract No. 1056.

Taneja et al., "Gene Therapy: Principles and Potential" *Cancer Surveys* (1995) 23: 247–266.

Taneja et al., "In vitro Target Specific Gene Therapy for Prostate Cancer Utilizing a Prostate Specific Antigen Promoter–Driven Adenoviral Vector" *Proceedings of the American Association for Cancer Research* (1991) 35:375 (Abstract No. 2236).

Taneja et al., "The Prostate–Specific Antigen Promoter Permits Androgen–Mediated Expression of Transfected Genes in Prostate Cancer Cell Line LNCaP" *Surgical Forum* (1994) 45:802–805.

Tijan et al., "Trancriptional Activation: A Complex Puzzle with Few Easy Pieces" *Cell* (1994) 77:5–8.

Trapman et al., "Characterization of the Prostate Specific Antigen Promoter and the Human Glandular Kallikrein–1 Promoter" *J. Cell Biochem.* (1992) 16:48(Abstract No. L433).

Trubetskoy et al., "Cationic Liposomes Enhance Targeted Delivery and Expression of Exogenous DNA Mediated by N–terminal Modified Poly (L–lysine)–Antibody Conjugate in Mouse Lung Endothelial Cells" *Biochem. Biophys. Acta* (1992) 1131:311–313.

Tsai et al., "Cooperative Binding of Steroid Hormone Receptors Contributes to Transcriptional Synergism at Target Enhancer Elements" *Cell* (1989) 57:443–448.

Wagner et al., "Transferrin–Polycation Conjugates as Carriers for DNA Uptake into Cells" *Proc. Natl. Acad. Sci. (USA).* (1990) 87:3410–3414.

Wang et al., "Highly Efficient DNA Delivery Mediated by pH–Sensitive Immunoliposomes" *Biochemistry* (1989) 28:9508–9514.

Wang et al., "pH–Sensitive Immunoliposomes Mediate Target–Cell–Specific Delivery and Controlled Expression of a Foreign Gene in Mouse" *Proc. Natl. Acad. Sci. (USA).* (1987) 84:7851–7855.

Wang et al., "Plasmid DNA Adsorbed to pH–sensitive liposomes efficiently transforms the target cells" *Biochem. Biophys. Res. Commun.* (1987) 147: 980–985.

Watanabe et al., "Induction of Antibodies to a κV Region by Gene Immunization" *J. Immunol.* (1993) 151:2871–2876.

Weinberger et al., "Human Steroid Receptors and erb–A Gene Products Form a Superfamily of Enhancer–Binding Proteins" *Clin. Physiol. Biochem.* (1987) 5:179–189.

Wilson et al., "Hepatocyte–directed Gene Transfer in vivo Leads to Transient Improvement of Hypercholesterolemia in Low Density Lipoprotein Receptor–deficient Rabbits" *J. Biol. Chem.* (1992) 267:963–967.

Wolf et al., "Transcriptional Regulation of Prostate Kallikrein–like Genes by Androgen" *Mol. Endocrinol.* (1992) 6:753–762.

Wright, et al., "Immunohistochemical Evaluation of the Expression of Prostate Tumor–Association Markers in the Nude Mouse Human Prostate Carcinoma Heterotransplant Lines PC–82, PC–EW, and PC–EG" *The Prostate* (1990) 17:301–316.

Wu et al., "Evidence for Targeted Gene Delivery to Hep G2 Hepatoma Cells in vitro" *Biochemistry* (1988) 27:887–892.

Wu et al., "Receptor–mediated Gene Delivery and Expression in vivo" *J. Biol. Chem.* (1988) 263:14621–14624.

Wu et al., "Receptor–mediated Gene Delivery in vivo" *J. Biol. Chem.* (1991) 266:14338–14342.

Wu et al., "Receptor–Mediated in vitro Gene Transformation by a Soluble DNA Carrier System" *J. Biol. Chem.* (1987) 262:4429–4432.

Wu et al., "Specific Inhibition of Hepatitis B Viral Gene Expression in vitro by Targeted Antisense Oligonucleotides" *J. Biol. Chem.* (1992) 267:12436–12439.

Young et al., "Tissue–Specific and Hormonal Regulation of Human Prostate–Specific Glandular Kallikrein" *Biochemistry* (1992) 31: 818–824.

Zenke et al., "Receptor–Mediated Endocytosis of Transferrin–Polycation Conjugates: An Efficient Way to Introduce DNA into Hematopoietic Cells" *Proc. Natl. Acad. Sci. (USA).* (1990) 87:3655–3659.

Zhou et al., "Lipophilic Polylysines Mediate Efficient DNA Transfection in Mammalian Cells" *Biochem. Biophys. Acta* (1991) 1065:8–14.

Zijlstra et al., "Germ–line Transmission of a Disrupted $\beta_2$–Microglobulin Gene Produced by Homologous Recombination in Embryonic Stem Cells" *Nature* (1989) 342:435–438.

Friedmann (Scientific American, Jun. 1997, pp. 96–101).

(Ronald Crystal, Science (1995) 270: 404–409).

Mastrangelo et al. (Seminars in Oncology, 1996, vol. 23, 1:4–21).

Sequence Range: -5824 to 12

>HinDIII

| | | | | |
|---|---|---|---|---|
| -5820-5815 | -5810-5805 | -5800-5795 | -5790-5785 | -5780-5775 | -5770-5765 |
| AAGCTTCTAG | TTTTCTTTTC | CCGGTGACAT | CGTGGAAAGC | ACTAGCATCT | CTAAGCAATG |
| -5760-5755 | -5750-5745 | -5740-5735 | -5730-5725 | -5720-5715 | -5710-5705 |
| ATCTGTGACA | ATATTCACAG | TGTAATGCCA | TCCAGGGAAC | TCAACTGAGC | CTTGATGTCC |
| -5700-5695 | -5690-5685 | -5680-5675 | -5670-5665 | -5660-5655 | -5650-5645 |
| AGAGATTTTT | GTGTTTTTT | CTGAGACTGA | GTCTCGCTCT | GTGCCAGGCT | GGAGTGCAGT |
| -5640-5635 | -5630-5625 | -5620-5615 | -5610-5605 | -5600-5595 | -5590-5585 |
| GGTGCAACCT | TGGCTCACTG | CAAGCTCCGC | CTCCTGGGTT | CACGCCATTC | TCCTGCCTCA |
| -5580-5575 | -5570-5565 | -5560-5555 | -5550-5545 | -5540-5535 | -5530-5525 |
| GCCTCCTGAG | TAGCTGGGAC | TACAGGCACC | CGCCACCACG | CCTGGCTAAT | TTTTTTGTAT |
| -5520-5515 | -5510-5505 | -5500-5495 | -5490-5485 | -5480-5475 | -5470-5465 |
| TTTTAGTAGA | GATGGGGTTT | CACTGTGTTA | GCCAGGATGG | TCTCAGTCTC | CTGACCTCGT |
| -5460-5455 | -5450-5445 | -5440-5435 | -5430-5425 | -5420-5415 | -5410-5405 |
| GATCTGCCCA | CCTTGGCCTC | CCAAAGTGCT | GGGATGACAG | GCGTGAGCCA | CCGCGCCTGG |
| -5400-5395 | -5390-5385 | -5380-5375 | -5370-5365 | -5360-5355 | -5350-5345 |
| CCGATATCCA | GAGATTTTT | GGGGGGCTCC | ATCACACAGA | CATGTTGACT | GTCTTCATGG |
| -5340-5335 | -5330-5325 | -5320-5315 | -5310-5305 | -5300-5295 | -5290-5285 |
| TTGACTTTTA | GTATCCAGCC | CCTCTAGAAA | TCTAGCTGAT | ATAGTGTGGC | TCAAAACCTT |

>XbaI

FIG. 1A

| | | | | |
|---|---|---|---|---|
| -5280/-5275 | -5270/-5265 | -5260/-5255 | -5250/-5245 | -5240/-5235 | -5230/-5225 |
| CAGCACAAAT | CACACCGTTA | GACTATCTGG | TGTGGCCCAA | ACCTTCAGGT | GAACAAAGGG |
| -5220/-5215 | -5210/-5205 | -5200/-5195 | -5190/-5185 | -5180/-5175 | -5170/-5165 |
| ACTCTAATCT | GGCAGGATAT | TCCAAAGCAT | TAGAGATGAC | CTCTTGCAAA | GAAAAAGAAA |
| -5160/-5155 | -5150/-5145 | -5140/-5135 | -5130/-5125 | -5120/-5115 | -5110/-5105 |
| TGGAAAAGAA | AAAGAAAGAA | AGGAAAAAAA | AAAAAAAAAA | GAGATGACCT | CTCAGGCTCT |
| -5100/-5095 | -5090/-5085 | -5080/-5075 | -5070/-5065 | -5060/-5055 | -5050/-5045 |
| GAGGGGAAAC | GCCTGAGGTC | TTTGAGCAAG | GTCAGTCCTC | TGTTGCACAG | TCTCCCTCAC |
| -5040/-5035 | -5030/-5025 | -5020/-5015 | -5010/-5005 | -5000/-4995 | -4990/-4985 |
| AGGGTCATTG | TGACGATCAA | ATGTGGTCAC | GTGTATGAGG | CACCAGCACA | TGCCTGGCTC |
| -4980/-4975 | -4970/-4965 | -4960/-4955 | -4950/-4945 | -4940/-4935 | -4930/-4925 |
| TGGGGAGTGC | CGTGTAAGTG | TATGCTTGCA | CTGCTGAATG | CTTGGGATGT | GTCAGGGATT |
| -4920/-4915 | -4910/-4905 | -4900/-4895 | -4890/-4885 | -4880/-4875 | -4870/-4865 |
| ATCTTCAGCA | CTTACAGATG | CTCATCTCAT | CCTCACAGCA | TCACTATGG | ATGGTATTA |
| -4860/-4855 | -4850/-4845 | -4840/-4835 | -4830/-4825 | -4820/-4815 | -4810/-4805 |
| CTGGCCTCAT | TTGATGGAGA | AAGTGGCTGT | GGCTCAGAAA | GGGGGACCA | CTAGACCAGG |
| | | | | >PstI | |
| -4800/-4795 | -4790/-4785 | -4780/-4775 | -4770/-4765 | -4760/-4755 | -4750/-4745 |
| GACACTCTGG | ATGCTGGGA | CTCCAGAGAC | CATGACCACT | CACCAACTGC | AGAGAAATTA |
| -4740/-4735 | -4730/-4725 | -4720/-4715 | -4710/-4705 | -4700/-4695 | -4690/-4685 |
| ATTGTGGCCT | GATGTCCCTG | TCCTGGAGAG | GGTGGAGGTG | GACCTTCACT | AACCTCCTAC |

FIG. 1B

| -4680-4675 | -4670-4665 | -4660-4655 | -4650-4645 | -4640-4635 | -4630-4625 |
|---|---|---|---|---|---|
| CTTGACCCTC | TCTTTTAGGG | CTCTTTCTGA | CCTCCACCAT | GGTACTAGGA | CCCCATTGTA |
| -4620-4615 | -4610-4605 | -4600-4595 | -4590-4585 | -4580-4575 | -4570-4565 |
| TTCTGTACCC | TCTTGACTCT | ATGACCCCCA | CTGCCCACTG | CATCCAGCTG | GGTCCCCTCC |
| -4560-4555 | -4550-4545 | -4540-4535 | -4530-4525 | -4520-4515 | -4510-4505 |
| TATCTCTATT | CCCAGCTGGC | CAGTGCAGTC | TCAGTGCCCA | CCTGTTTGTC | AGTAACTCTG |
| -4500-4495 | -4490-4485 | -4480-4475 | -4470-4465 | -4460-4455 | -4450-4445 |
| AAGGGGCTGA | CATTTTACTG | ACTTGCAAAC | AAATAAGCTA | ACTTTCCAGA | GTTTTGTGAA |
| -4440-4435 | -4430-4425 | -4420-4415 | -4410-4405 | -4400-4395 | -4390-4385 |
| TGCTGGCAGA | GTCCATGAGA | CTCCTGAGTC | AGAGGCAAAG | GCTTTTACTG | CTCACAGCTT |
| -4380-4375 | -4370-4365 | -4360-4355 | -4350-4345 | -4340-4335 | -4330-4325 |
| AGCAGACAGC | ATGAGGTTCA | TGTTCACATT | AGTACACCTT | GCCCCCCCA | AATCTTGTAG |
| -4320-4315 | -4310-4305 | -4300-4295 | -4290-4285 | -4280-4275 | -4270-4265 |
| GGTGACCAGA | GCAGTCTAGG | TGGATGCTGT | GCAGAAGGGG | TTTGTGCCAC | TGGTGAGAAA |
| -4260-4255 | -4250-4245 | -4240-4235 | -4230-4225 | -4220-4215 | -4210-4205 |
| CCTGAGATTA | GGAATCCTCA | ATCTTATACT | GGGACAACTT | GCAAACCTGC | TCAGCCTTTG |
| -4200-4195 | -4190-4185 | -4180-4175 | -4170-4165 | -4160-4155 | -4150-4145 |
| TCTCTGATGA | AGATATTATC | TTCATGATCT | TGGATTGAAA | ACAGACCTAC | TCTGGAGGAA |
| >ClaI | | | | | |
| -4140-4135 | -4130-4125 | -4120-4115 | -4110-4105 | -4110-4095 | -4090-4085 |
| CATATTGTAT | CGATTGTCCT | TGACAGTAAA | CAAATCTGTT | GTAAGAGACA | TTATCTTTAT |

FIG. 1C

```
-4080-4075  -4070-4065  -4060-4055  -4050-4045  -4040-4035  -4030-4025
TATCTAGGAC  AGTAAGCAAG  CCTGGATCTG  AGAGAGATAT  CATCTTGCAA  GGATGCCTGC
-4020-4015  -4010-4005  -4000-3995  -3990-3985  -3980-3975  -3970-3965
TTTACAAACA  TCCTTGAAAC  AACAATCCAG  AAAAAAAAAG  GTGTTGCTGT  CTTTGCTCAG
-3960-3955  -3950-3945  -3940-3935  -3930-3925  -3920-3915  -3910-3905
AAGACACACA  GATACGTGAC  AGAACCATGG  AGAATTGCCT  CCCAACGCTG  TTCAGCCAGA
            >PstI
-3900-3895  -3890-3885  -3880-3875  -3870-3865  -3860-3855  -3850-3845
GCCTTCCACC  CTTGTCTGCA  GGACAGTCTC  AACGTTCCAC  CATTAAATAC  TTCTTCTATC
-3840-3835  -3830-3825  -3820-3815  -3810-3805  -3800-3795  -3790-3785
ACATCCTGCT  TCTTTATGCC  TAACCAAGGT  TCTAGGTCCC  GATCGACTGT  GTCTGGCAGC
                                    >BamHI
-3780-3775  -3770-3765  -3760-3755  -3750-3745  -3740-3735  -3730-3725
ACTCCACTGC  CAAACCCAGA  ATAAGGCAGC  GCTCAGGATC  CCGAAGGGGC  ATGGCTGGGG
-3720-3715  -3710-3705  -3700-3695  -3690-3685  -3680-3675  -3670-3665
ATCAGAACTT  CTGGGTTTGA  GTGAGGAGTG  GGTCCACCCT  CTTGAATTTC  AAAGGAGGAA
-3660-3655  -3650-3645  -3640-3635  -3630-3625  -3620-3615  -3610-3605
GAGGCTGGAT  GTGAAGGTAC  TGGGGGAGGG  AAAGTGTCAG  TTCCGAACTC  TTAGGTCAAT
-3600-3595  -3590-3585  -3580-3575  -3570-3565  -3560-3555  -3550-3545
GAGGGAGGAG  ACTGGTAAGG  TCCCAGCTCC  CGAGGTACTG  ATGTGGAAT   GGCCTAAGAA
```

FIG. 1D

| | | | | | |
|---|---|---|---|---|---|
| -3540-3535 TCTCATATCC | -3530-3525 TCAGGAAGAA | -3520-3515 GGTGCTGGAA | -3510-3505 TCCTGAGGGG | -3500-3495 TAGAGTTCTG | -3490-3485 GGTATATTTG |
| -3480-3475 TGGCTTAAGG | -3470-3465 CTCTTTGGCC | -3460-3455 CCTGAAGGCA | -3450-3445 GAGGCTGGAA | -3440-3435 CCATTAGGTC | -3430-3425 CAGGGTTTGG |
| -3420-3415 GGTGATAGTA | -3410-3405 ATGGGATCTC | -3400-3395 TTGATTCCTC | -3390-3385 AAGAGTCTGA | -3380-3375 GGATCGAGGG | -3370-3365 TTGCCCATTC |
| -3360-3355 TTCCATCTTG | -3350-3345 CCACCTAATC | -3340-3335 CTTACTCCAC | -3330-3325 TTGAGGGTAT | -3320-3315 CACCAGCCCT | -3310-3305 TCTAGCTCCA |
| -3300-3295 TGAAGGTCCC | -3290-3285 CTGGGCAAGC | -3280-3275 ACAATCTGAG | -3270-3265 CATGAAAGAT | -3260-3255 GCCCCAGAGG | -3250-3245 CCTTGGGTGT |
| -3240-3235 CATCCACTCA | -3230-3225 TCATCCAGCA >PstI | -3220-3215 TCACACTCTG | -3210-3205 AGGGTGTGGC | -3200-3195 CAGCACCATG | -3190-3185 ACGTCATGTT |
| -3180-3175 GCTGTGACTA | -3170-3165 TCCCTGCAGC | -3160-3155 GTGCCTCTCC | -3150-3145 AGCCACCTGC | -3140-3135 CAACCGTAGA | -3130-3125 GCTGCCCATC |
| -3120-3115 CTCCTCTGGT >BamHI | -3110-3105 GGGAGTGGCC | -3100-3095 TGCATGGTGC | -3090-3085 CAGGCTGAGG | -3080-3075 CCTAGTGTCA | -3070-3065 GACAGGGAGC |
| -3060-3055 CTGGAATCAT | -3050-3045 AGGGATCCAG | -3040-3035 GACTCAAAAG | -3030-3025 TGCTAGAGAA | -3020-3015 TGGCCATATG | -3010-3005 TCACCATCCA |

FIG. 1E

```
-3000-2995  -2990-2985  -2980-2975  -2970-2965  -2960-2955  -2950-2945
TGAAATCTCA  AGGGCTTCTG  GGTGGAGGGC  ACAGGGACCT  GAACTTATGG  TTTCCCAAGT
-2940-2935  -2930-2925  -2920-2915  -2910-2905  -2900-2895  -2890-2885
CTATTGCTCT  CCCAAGTGAG  TCTCCCAGAT  ACGAGGCACT  GTGCCAGCAT  CAGCCTTATC
                                    >ApaI
-2880-2875  -2870-2865  -2860-2855  -2850-2845  -2840-2835  -2830-2825
TCCACCACAT  CTTGTAAAAG  GACTACCCAG  GGCCCTGATG  AACACCATGG  TGTGTACAGG
-2820-2815  -2810-2805  -2800-2795  -2790-2785  -2780-2775  -2770-2765
AGTAGGGGT   GGAGGCACGG  ACTCCTGTGA  GGTCACAGCC  AAGGGAGCAT  CATCATGGGT
-2760-2755  -2750-2745  -2740-2735  -2730-2725  -2720-2715  -2710-2705
GGGGAGGAGG  CAATGGAGAAC GCTTGAGAAC GGGGATGTGG  TTGTATTTGG  TTTTCTTTGG
-2700-2695  -2690-2685  -2680-2675  -2670-2665  -2660-2655  -2650-2645
TTAGATAAAG  TGCTGGGTAT  AGGATTGAGA  GTGGAGTATG  AAGACCAGTT  AGGATGGAGG
-2640-2635  -2630-2625  -2620-2615  -2610-2605  -2600-2595  -2590-2585
ATCAGATTGG  AGTTGGGTTA  GATAAAGTGC  TGGGTATAGG  ATTGAGAGTG  GAGTATGAAG
-2580-2575  -2570-2565  -2560-2555  -2550-2545  -2540-2535  -2530-2525
ACCAGTTAGG  ATGGAGGATC  AGATTGGAGT  TGGGTTAGAG  ATGGGTAAA   ATTGTGCTCC
-2520-2515  -2510-2505  -2500-2495  -2490-2485  -2480-2475  -2470-2465
GGATGAGTT   GGGATTGACA  CTGTGGAGGT  GGTTTGGGAT  GGCATGGCTT  TGGGATGGAA
-2460-2455  -2450-2445  -2440-2435  -2430-2425  -2420-2415  -2410-2405
ATAGATTTGT  TTTGATGTTG  GCTCAGACAT  CCTTGGGGAT  TGAACTGGGG  ATGAAGCTGG
```

FIG. 1F

| | | | | | |
|---|---|---|---|---|---|
| -2400-2391 GTTTGATTTT | -2390-2381 GGAGGTAGAA | -2380-2371 GACGTGGAAG | -2370-2361 TAGCTGTCAG | -2360-2351 ATTTGACAGT | -2350-2341 GGCCATGAGT |
| -2340-2331 TTTGTTTGAT | -2330-2321 GGGGAATCAA | -2320-2311 ACAATGGGGG | -2310-2301 AAGACATAAG | -2300-2291 GGTTGGCTTG | -2290-2281 TTAGGTTAAG |
| -2280-2271 TTGCGTTGGG | -2270-2261 TTGATGGGGT | -2260-2251 CGGGCTGTG | -2250-2241 TATAATGCAG | -2240-2231 TTGGATTGGT | -2230-2221 TTGTATTAAA >BamHI |
| -2220-2211 TTGGGTTGGG | -2210-2201 TCAGGTTTTG | -2200-2191 GTTGAGGATG | -2190-2181 AGTTGAGGAT | -2180-2171 ATGCTTGGGG | -2170-2161 ACACCGGATC |
| -2160-2151 CATGAGGTTC | -2150-2141 TCACTGGAGT | -2140-2131 GGAGACAAAC | -2130-2121 TTCCTTTCCA | -2120-2111 GGATGAATCC | -2110-2101 AGGGAAGCCT |
| -2100-2091 TAATTCACGT | -2090-2081 GTAGGGGAGG | -2080-2071 TCAGGCCACT | -2070-2061 GGCTAAGTAT | -2060-2051 ATCCTTCCAC | -2050-2041 TCCAGTCTA |
| -2040-2031 AGATGGTCTT | -2030-2021 AAATTGTGAT | -2020-2011 TATCTATATC | -2010-2001 CACTTCTGTC | -2000-1991 TCCCTCACTG | -1990-1981 TGCTTGGAGT |
| -1980-1971 TTACCTGATC | -1970-1961 ACTCAACTAG | -1960-1951 AAACAGGGGA | -1950-1941 AGATTTTATC | -1940-1931 TCCCTTACTG | -1930-1921 TTTTTTTT |
| -1920-1911 TTTTTTTGA | -1910-1901 GACAGAGTCT | -1900-1891 CACTCTGTTG | -1890-1881 AGATTTTATC | -1880-1871 AGTGCAGTGG | -1870-1861 CGCAGTCTCG |
| -1860-1851 GCTCACTGCA | -1850-1841 ACCTCTGCCT | -1840-1831 CCCAGGTTCA | -1830-1821 CCCAGGCTGG | -1820-1811 AGTGCAGTGG | -1810-1801 CGCAGTCTCG |
| | | | | | -1810-1801 CTCCTGAGT |

FIG. 1G

| -1800--1795 | -1790--1785 | -1780--1775 | -1770--1765 | -1760--1755 | -1750--1745 |
|---|---|---|---|---|---|
| GCTGGGATTA | CAGGCATGCA | GCACCATGCC | CAGCTAATTT | TTGTATTTTT | AGTAGAGATG |
| -1740--1735 | -1730--1725 | -1720--1715 | -1710--1705 | -1700--1695 | -1690--1685 |
| GGGTTTCACC | AATGTTTGCC | AGGCTGGCCT | CGAACTCCTG | ACCTGGTGAT | CCACCTGCCT |
| -1680--1675 | -1670--1665 | -1660--1655 | -1650--1645 | -1640--1635 | -1630--1625 |
| CAGCCTCCCA | AAGTGCTGGG | ATTACAGGCG | TCAGCCACCG | CGCCCAGCCA | CTTTTGTCAA |
| -1620--1615 | -1610--1605 | -1600--1595 | -1590--1585 | -1580--1575 | -1570--1565 |
| ATTCTTGAGA | CACAGCTCGG | GCTGGATCAA | GTGAGCTACT | CTGGTTTTAT | TGAACAGCTG |
|  |  |  |  |  | >KpnI |
| -1560--1555 | -1550--1545 | -1540--1535 | -1530--1525 | -1520--1515 | -1510--1505 |
| AAATAACCAA | CTTTTTGGAA | ATTGATGAAA | TCTTACGGAG | TTAACAGTGG | AGGTACCAGG |
| -1500--1495 | -1490--1485 | -1480--1475 | -1470--1465 | -1460--1455 | -1450--1445 |
| GCTCTTAAGA | GTTCCCGATT | CTCTTCTGAG | ACTACAAATT | GTGATTTTGC | ATGCCACCTT |
| -1440--1435 | -1430--1425 | -1420--1415 | -1410--1405 | -1400--1395 | -1390--1385 |
| AATCTTTTT | TTTTTTTTT | TAAATCGAGG | TTTCAGTCTC | ATTCTATTTC | CCAGGCTGGA |
| -1380--1375 | -1370--1365 | -1360--1355 | -1350--1345 | -1340--1335 | -1330--1325 |
| GTTCAATAGC | GTGATCACAG | CTCACTGTAG | CCTTGAACTC | CTGGCCTTAA | GAGATTCTCC |
| -1320--1315 | -1310--1305 | -1300--1295 | -1290--1285 | -1280--1275 | -1270--1265 |
| TGCTTCGGTC | TCCCAATAGC | GTAGTCCACC | TAAGACTACA | ACCATATCCA | GATAATTTTT |
| -1260--1255 | -1250--1245 | -1240--1235 | -1230--1225 | -1220--1215 | -1210--1205 |
| AAATTTTTG | GGGGGCCGGG | CACAGTGGCT | CACGCCTGTA | ATCCCAACAC | CATGGGAGGC |

FIG. 1H

| -1200 -1195 | -1190 -1185 | -1180 -1175 | -1170 -1165 | -1160 -1155 | -1150 -1145 |
|---|---|---|---|---|---|
| TGAGATGGGT | GGATCACGAG | GTCAGGAGTT | TGAGACCAGC | CTGACCAACA | TGGTGAAACT |
| -1140 -1135 | -1130 -1125 | -1120 -1115 | -1110 -1105 | -1100 -1095 | -1090 -1085 |
| CTGTCTCTAC | TAAAAAAAAA | AAAAATAGAA | AAATTAGCCG | GGCGTGGTGG | CACACGGCAC |
| -1080 -1075 | -1070 -1065 | -1060 -1055 | -1050 -1045 | -1040 -1035 | -1030 -1025 |
| CTGTAATCCC | AGCTACTGAG | GAGGCTGAGG | CAGGAGAATC | ACTTGAACCC | AGAAGGCAGA |
| -1020 -1015 | -1010 -1005 | -1000 -995 | -990 -985 | -980 -975 | -970 -965 |
| GGTTGCAATG | AGCCGAGATT | GCGCCACTGC | ACTCCAGCCT | GGGTGACAGA | GTGAGACTCT |
| -960 -955 | -950 -945 | -940 -935 | -930 -925 | -920 -915 | -910 -905 |
| CTCTCAAAAA | AAAAAATTT | TTTTTTTTT | TTTGTAGAGA | TGGATCTTGC | TTTGTTTCTC |
| -900 -895 | -890 -885 | -880 -875 | -870 -865 | -860 -855 | -850 -845 |
| TGGTTGGCCT | TGAACTCCTG | GCTTCAAGTG | ATCCTCCTAC | CTTGGCCTCG | GAAAGTGTTG |
| -840 -835 | -830 -825 | -820 -815 | -810 -805 | -800 -795 | -790 -785 |
| GGATTACAGG | CGTGAGCCAC | CATGACTGAC | CTGTCGTTAA | TCTTGAGGTA | CATAAACCTG |
| -780 -775 | -770 -765 | -760 -755 | -750 -745 | -740 -735 | -730 -725 |
| GCTCCTAAAG | GCTAAAGGCT | AAATATTTGT | TGGAGAAGGG | GCATTGGATT | TTGCATGAGG |
| -720 -715 | -710 -705 | -700 -695 | -690 -685 | -680 -675 | -670 -665 |
| ATGATTCTGA | CCTGGGAGGG | CAGGTCAGCA | GGCATCTCTG | TTGCACAGAT | AGAGTGTACA |
| -660 -655 | -650 -645 | -640 -635 | >EcoRI -630 -625 | -620 -615 | -610 -605 |
| GGTCTGGAGA | ACAAGGAGTG | GGGGTTATT | GGAATTCCAC | ATTGTTTGCT | GCACGTTGGA |

FIG. 1I

```
-600 -595*   -590 -585*   -580 -575*   -570 -565*   -560 -555*   -550 -545*
TTTGAAATG    CTAGGGAACT   TGGGAGACT    CATATTTCTG   GGCTAGAGGA   TCTGTGGACC
-540 -535*   -530 -525*   -520 -515*   -510 -505*   -500 -495*   -490 -485*
ACAAGATCTT   TTTATGATGA   CAGTAGCAAT   GTATCTGTGG   AGCTGGATTC   TGGGTTGGGA
-480 -475*   -470 -465*   -460 -455*   -450 -445*   -440 -435*   -430 -425*
GTGCAAGGAA   AAGAATGTAC   TAAATGCCAA   GACATCTATT   TCAGGAGCAT   GAGGAATAAA
-420 -415*   -410 -405*   -400 -395*   -390 -385*   -380 -375*   -370 -365*
AGTTCTAGTT   TCTGGTCTCA   GAGTGGTGCA   GGGATCAGGG   AGTCTCACAA   TCTCCTGAGT
-360 -355*   -350 -345*   -340 -335*   -330 -325*   -320 -315*   -310 -305*
GCTGGTGTCT   TAGGGCACAC   TGGGTCTTGG   AGTGCAAAGG   ATCTAGGCAC   GTGAGGCTTT
-300 -295*   -290 -285*   -280 -275*   -270 -265*   -260 -255*   -250 -245*
GTATGAAGAA   TCGGGGATCG   TACCCACCCC   CTGTTTCTGT   TTCATCCTGG   GCATGTCTCC
-240 -235*   -230 -225*   -220 -215*   -210 -205*   -200 -195*   -190 -185*
TCTGCCTTTG   TCCCCTAGAT   GAAGTCTCCA   TGAGCTACAA   GGGCCTGGTG   CATCCAGGGT
-180 -175*   -170 -165*   -160 -155*   -150 -145*   -140 -135*   -130 -125*
GATCTAGTAA   TTGCAGAACA   GCAAGTGCTA   GCTCTCCCTC   CCCTTCCACA   GCTCTGGGTG
-120 -115*   -110 -105*   -100  -95*    -90  -85*    -80  -75*    -70  -65*
TGGGAGGGG    TTGTCCAGCC   TCCAGCAGCA   TGGGGAGGGC   CTTGGTCAGC   CTCTGGGTGC
 -60  -55*   -50  -45*    -40  -35*    -30  -25*    -20  -15*    -10   -5*
CAGCAGGGCA   GGGGCGGAGT   CCTGGGAAT    GAAGGTTTTA   TAGGGCTCCT   GGGGAGGCT

>HinDIII
   1    6*       11
   CCCCAGCCCC   AAGCTT
```

FIG. 1J

CAT Assays to locate PSA Enhancer 1   2   3   4   5   6   7

| | LNCaP | PANC | MCF-7 | OVCAR | DU-145 | HBL-100 |
|---|---|---|---|---|---|---|
| CN 33  ⊢553⊢CAT | 1.0 | 1.0 | 1.0 | 1.0 | 1.0 | 1.0 |
| CN 65  x⊢1582⊢CAT | 24.3 | 1.3 | .4 | .8 | 1.0 | .8 |
| CN 102  x⊢1582⊢CAT | 31.1 | 2.0 | .6 | 1.8 | 1.2 | 1.0 |
| CN 103  x⊢1582⊢233⊢CAT | 48.4 | 2.8 | .6 | 1.4 | 1.1 | 1.3 |
| CN 105  x⊢1448⊢CAT | 25.8 | 2.5 | .7 | 1.2 | 1.2 | 1.1 |
| CN 104  x⊢1299⊢CAT | 16.0 | 4.6 | 1.6 | 2.0 | 1.2 | 1.9 |

FIG. 15

TISSUE-SPECIFIC ENHANCER ACTIVE IN PROSTATE

CROSS-REFERENCE TO RELATED APPLICATIONS

This application is a continuation-in-part of application Ser. No. 08/380,916, filed Jan. 30, 1995 now U.S. Pat. No. 5,648,478, which is a continuation-in-part of application Ser. No. 08/182,247, filed Jan. 13, 1994 now U.S. Pat. No. 5,830,686, and a continuation-in-part of application Ser. No. 08/669,753, filed Jun. 26, 1996, now U.S. Pat. No. 5,871,726 which is a continuation in-part of application Ser. No. 08/495,034, filed Jun. 27, 1995 now U.S. Pat. No. 5,698,443.

FIELD OF THE INVENTION

The invention provides novel transcriptional regulatory elements (enhancers) which preferentially enhance the net transcription of cis-linked transcription units in prostate tissue. The tissue-specific prostate enhancers of the present invention are preferentially active in prostatic cells as compared with other tissues. The invention also provides compositions suitable for genetic therapy of prostate hyperplasia and neoplasia, and methods for treating such disease conditions using the novel compositions, which comprise polynucleotides suitable for use as transgenes and/or gene-targeting constructs.

BACKGROUND

BPH. Prostate Neoplasia and Treatment Modalities

There are three significant diseases of the prostate: benign prostate hyperplasia (BPH), prostate cancer, and rostatitis. The costs of these three diseases are immense. In 1985, the annual treatment of prostate diseases in the US required 4.4 million physician visits, 836,000 hospitalizations, and cost over $3 billion. In 1985, the costs for BPH, prostate cancer, and prostatitis were $1.82, $0.97, and $0.29 billion respectively. clearly these diseases represent a significant percentage of the American health care dollar. In addition prostate cancer caused 39,215 deaths. BPH and prostate cancer are diseases of men over 50. Due to the aging US population, the incidence of BPH and prostate cancer will increase 50% in the next 15 years.

BPH causes urinary obstruction resulting in urinary incontinence. It occurs in almost 80% of men by the age of 80. Unregulated dihydrotestosterone is believed to cause hyperplastic prostate growth in aging men.

Pharmacotherapy for the treatment of BPH is currently aimed to relax prostate smooth muscle (alpha blockade) and decrease prostate volume (androgen suppression). Phase III clinical trials are underway evaluating selective $alpha_1$ blockers, anti-androgens, and 5-alpha reductase inhibitors for the treatment of BPH. The most promising of these is finasteride. It has shown an ability to cause regression of the hyperplastic prostate gland in a majority of patients (Mocellini et.al. (1993) *Prostate* 22:291).

BPH is treated surgically with a transurethral resection of the prostate (TURP). This procedure is most common: 500,000 TURPs are performed in the US each year and 25% of men will require surgery at some time in their lives to alleviate urinary obstruction. This makes BPH the second most common cause of surgery in males after cataract surgery. The TURP procedure requires several days hospitalization as well as the surgery itself. The average medical reimbursement cost of a TURP in 1987 dollars was $8,000; in 1993 dollars this is $14,000. Unfortunately, a side-effect of the TURP is the elimination of the ejaculatory ducts resulting in impotence in 90% of patients. A TURP is prefaced by an outpatient biopsy procedure to determine if the enlargement of the prostate is benign or cancerous.

Prostate cancer is the second most common cause of cancer death in American males where only lung cancer is greater. Prostate cancer is a latent disease; many men carry prostate cancer cells without overt signs of disease. Autopsies of individuals dying of other causes show prostate cancer cells in 30% of men at age 50; by the age of 80 years, the prevalence is 60% of prostates. Further, prostate cancer can take up to 10 years to kill the patient after initial diagnosis. Prostate cancer is newly diagnosed in slightly over 100,000 men in the US. each year of which over 40,000 will die of the disease. There is also high morbidity. Cancer metastasis to bone (late stage) is common and often associated with uncontrollable pain. Metastasis also occurs to lymph nodes (early stage).

The progression of the disease is from a well-defined mass within the prostate, to a breakdown and invasion of the lateral margins of the prostate, to metastasis to regional lymph nodes, to metastasis to the bone marrow. The aggressiveness of prostate tumors varies widely. Some tumors are relatively aggressive, doubling every six months, whereas other are extremely slow-growing, doubling once every five years. As a consequence of the slow growth rate, few cancer cells are actively dividing at any one time. As a result, prostate cancer is generally resistant to radiation and chemotherapy, although both therapeutic modalities are widely used. Surgery is the mainstay of treatment but it too is largely ineffective and also removes the ejaculatory ducts, resulting in impotence.

Unfortunately, in 80% of cases, diagnosis of prostate cancer is established when the disease has already metastasized to the bones. Of special interest is the observation that prostate cancers frequently grow more rapidly in sites of metastasis than within the prostate itself, the site of the primary cancer.

The diagnosis and management of prostate cancer has become simplified with the use of measurement of serum levels of prostate-specific antigen. Prostate-specific antigen (PSA) is a protease involved in the breakdown of the ejaculate coagulum. Serum levels of PSA vary from 2–4 ng/ml and usually a single determination of an individual's PSA level is meaningless. Most frequently PSA levels are elevated in both prostate cancer and BPH. A serum PSA level of over 4 ng/ml usually warrants further investigation. Even more telling are rapid increases in serum PSA levels which can indicate active prostate cancer. A rapid rise in PSA levels from 2–4 ng/ml to over 10 ng/ml indicates active disease (Hamdy, F.C., et al. (1992) *Br. J. Urol.* 69:392). In end-stage metastatic disease, PSA levels can reach 200 ng/ml. PSA is a single amino acid chain of 240 AA and has been cloned (Lundwall A. and Lilja H. (1987) *FEBS Lett* 214:317: Lundwall A (1989) *Biochem. Biophys. Res. Comm.* 161:1151; Riegman et al. (1989) *Biochem. Biophys. Res. Comm.* 159:95).

For the treatment of prostate cancer oral estrogens and luteinizing releasing hormone analogs are used as well as surgical removal of glands that produce androgens (orchiectomy or adrenalectomy). The Nobel prize was awarded in 1966 to Charles Huggins for utilizing castration for treatment of prostate cancer. Many patients showed marked improvement after castration, but this was only temporary relief. Most of these cancers soon relapsed and presented as a therapeutically resistant form that ultimately caused death. Current therapeutic techniques use chemical forms of medical castration by shutting down androgen production in the testes, or directly block androgen production in the prostate.

Estrogens are no longer recommended for therapy because of serious, even lethal, cardiovascular complications. Luteinizing hormone releasing hormone (LHRH) analogs are used instead. LHRH analogs are equally effective when compared to estrogens, or orchiectomy. LHRH treatments are reversible, do not involve surgery, and do not impact the patient psychologically. Thus, this treatment is preferable for producing androgenic deprivation. LHRH analogs initially increase pituitary LH secretion with a subsequent increase in serum testosterone. This results in a disease "flare" that rapidly subsides as the initial increase in LHRH-mediated LH secretion is reversed when over stimulation of pituitary LHRH receptors leads to a shutdown in their function and a consequent fall in LH secretion, and thus, testicular testosterone production (Redding et al. (1982) Proc. Natl. Acad. Sci. 79:1273). However, hormonal therapy invariably fails with time with the development of hormone-resistant tumor cells. It is not known whether these cells develop as a mutation of the original hormone sensitive cells, or as a separate class of cells. However, since 20% of patients fail to respond to hormonal therapy, it is believed that hormone-resistant cells are present at the onset of therapy.

Estramustine, a steroidal nitrogen mustard derivative, is undergoing clinical trials for advanced stage prostate cancer. Estramustine was originally thought to be suitable for targeted drug delivery through conjugation of estrogen to toxic nitrogen mustard. Surprisingly however, estramustine has no alkylating or hormonal effects. Rather, estramustine disassembles microtubles inhibiting cell division. Phase II and Phase III clinical trials over the past 15 years have been disappointing when survival is used as an endpoint.

Finasteride, a 4-aza steroid (Proscar® from Merck & Co.) inhibits 5α-reductase, the enzyme responsible for the intracellular conversion of testosterone to dihydrotestosterone in the stroma of the prostate. Since dihydrotestosterone is the most potent androgen in the prostate, its elimination causes regression of prostate cancer by as much as 40% in volume. Casodexthin® is thought to inhibit cellular uptake of testosterone by blocking androgen receptors in the nucleus. However, almost all advanced cancer prostate cells fail to respond to androgen deprivation. At this stage there is no effective cytotoxic chemotherapy for prostate cancer.

A major, indeed the overwhelming, obstacle to cancer therapy is the problem of selectivity; that is, the ability to inhibit the multiplication of tumor cells, while leaving unaffected the function of normal cells. Thus, the therapeutic ratio, or ratio of tumor cell killing to normal cell killing of traditional tumor chemotherapy, is only 1.5:1. Thus, more effective treatment methods and pharmaceutical compositions for therapy and prophylaxis of prostatic hyperplasia and neoplasia are needed.

Transcriptional Regulatory Elements

Methods and compositions are provided for prostate cell specific transcription, particularly human prostate cells comprising prostate specific antigen, a glandular kallikrein. An approximately 2.5 kbp fragment from about −2850 to about −5350 serves as a prostate specific enhancer ("PSE") in conjunction with a promoter to function to initiate transcription in prostate cells. constructions are provided for identifying cells which have the transcriptional components for regulating transcription in conjunction with the PSE and for genetically modifying neoplastic prostate cells to inhibit proliferation. The constructs employ the PSE in conjunction with a promoter region, particularly the 541 bp promoter region of the prostate-specific antigen, and a gene encoding a protein which permits selective ablation of prostate cells, particularly neoplastic prostate cells. Treatment of neoplastic cells comprises the introduction of the construct into neoplastic cells for specific ablation of the neoplastic cells.

Exploiting differential gene expression in neoplastic and hyperplastic cells represents one means for selectively killing such abnormal cells. The control of gene expression in various cell types commonly involved in neoplasia has been studied.

Recently, highly specific enhancers/promoters have been identified; that is, DNA sequences to which are bound proteins (e.g., transcription factors) that only exist in certain types of cells and which modulate the transcriptional activity of cis-linked DNA sequences. These enhancer-binding proteins are activators of transcription that regulate the expression of certain genes that are therefore expressed only in these cells and/or become transcriptionally active under certain conditions (e.g., when bound to a specific hormone, then phosphorylated, when certain other proteins are present). A number of transcriptionally active enhancer elements have been reported. Steroid-regulated enhancer elements have been identified and generally bind to ligand-bound steroid receptors (Nawaz et al. (1992) Gene Expr. 2: 39; Allan et al. (1991) 3 Biol. Chem. 266: 5905; Ozono et al. (1991) J. Biol. Chem. 265: 21881; Meyer et al. (1989) Cell 57: 443; Bagchi et al. (1988) Mol. Endocrinol.: 1221; Bradshaw et al. (1988) Mol. Endocrinol. 2 (12): 1286; Weinberger et al. (1987) Clin. Physiol. Biochem. 5: 179). Associated with expression of the prostate specific antigen is an androgen reponse element at position −175 to −155. A variety of tissue-specific enhancers and promoters have also been identified in numerous tissues, including liver (Rouet et al. (1992) J. Biol. Chem. 267: 20765; Lemaigne et al. (1993) J. Biol. Chem. 268: 19896; Nitsch et al. (1993) Mol. Cell. Biol. 13: 4494), stomach (Kovarik et al. (1993) J. Biol. Chem. 268: 9917), and pituitary gland (Rhodes et al. (1993) Genes Dev. 7: 913), among others.

Palmiter et al. (1987) Cell 50: 435, reports a strategy for using a pancreas-specific elastase I promoter/enhancer linked to a diphtheria toxin gene to form a chimeric transgene which, when introduced into fertilized murine eggs by micro-injection, can be used to generate a transgenic mouse wherein cells which normally express the elastase I gene are selectively deleted as a result of the expression of the diphtheria toxin encoded by the transgene. Similar strategies have also been used to produce transgenic mice lacking growth-hormone expressing cells (Behringer et al. (1988) Genes Dev. 2: 453) and transgenic mice that are deficient in Schwann cells (Messing et al. (1992) Neuron 8: 507).

The prostate-specific antigen (PSA) gene is preferentially expressed in prostate cells and has been cloned (Lundwall A and Lilja H (1987) FEBS Lett 214: 317; Lundwall A (1989) Biochem. Biophys. Res. Commun. 161: 1151; Riegmann et al. (1991) Molec. Endocrinol. 5: 1921).

However, tissue-specific enhancers and promoters which are active in prostate cells, and particularly in neoplastic or hyperplastic prostate cells, would be useful to those in the art, as would constructs suitable for therapeutic ablation of prostate tissue, especially neoplastic prostate epithelium. Therapy based on cell-specific transcriptional regulatory elements would provide a therapeutic modality which likely would be cell-type specific. For such an approach to be used for treating BPH and/or prostate cancer, it would be advantageous to have transcriptional regulatory elements which are preferentially active in prostate acinar cells, from which nearly all metastatic prostate carcinomas arise (Ghadzizadel et al. (1984) *Urol. Int.* 39: 9). Targeting acinar cells should leave the prostate stromal cells relatively unaffected, and retain the ejaculatory ducts and urethra that pass through it. This would be a significant advantage over present surgical approaches. The present invention fulfills these and other needs. The references discussed herein are provided solely for their disclosure prior to the filing date of the present application. Nothing herein is to be construed as an admission that the inventors are not entitled to antedate such disclosure by virtue of prior invention. All cited publications are incorporated herein by reference.

SUMMARY OF THE INVENTION

Methods and compositions are provided for specific transcription of genes incells expressing prostate specific antigen (PSA). A prostate specific enhancer(PSE) is provided which provides for enhanececd expression in cells having the transcription factors associated with expression of prostate specific antigen. Constructs providing for genes cis-linked and under the transcriptional control of the PSE are produced to allow for preferential enhancement of transcription in cells having transcription factors specific for the expression of PSA. The entire enhancer region of the PSA may be employed or fragments thereof, where the fragments are shown to bind to the transcription factors. Intervening sequences between the binding sequences, if present, may be the naturally occurring sequences or synthetic sequences.

In accordance with the foregoing, in one aspect of the invention is provided transcriptional regulatory elements, such as enhancers and promoters, which activate transcription of cis-linked sequences in prostate cells in a tissue-specific manner. Such elements are typically present in or adjacent to genes which are expressed preferentially in prostate cells but substantially not expressed in other cell types.

In one embodiment, the transcriptional regulatory element comprises an enhancer element present in the upstream flanking region of the prostate-specific antigen (PSA) gene, wherein said enhancer activates transcription of cis-linked sequences in prostate cells (e.g., prostate epithelium). In one variation, the transcriptional regulatory element comprises an approximately 5.3 kb fragment of the region immediately upstream of the human PSA gene; this 5.3 kb fragment is frequently isolated as a XbaI-HindIII fragment but restriction site polymorphisms may exist. In another variation, as much or more than 2.5 kp can be deleted internally within the approximately 5.3 kp fragment.

In one aspect of the invention are provided polynucleotides comprising a transcriptional regulatory element that activates transcription of cis-linked sequences in prostate cells such as neoplastic or hyperplastic prostate cells. Typically, such polynucleotides further comprise a structural gene (e.g., a cDNA or genomic gene or minigene) or an antisense sequence operably linked to the transcriptional regulatory element forming a transcription unit. Such a transcription unit generally comprises a structural gene operably linked to a promoter and optionally also a prostate-specific enhancer (i.e., an enhancer element functional in prostate cells but substantially inactive in other cell types). Most usually, the polynucleotides of the invention are used as transgenes and/or homologous targeting constructs and are typically dsDNA constructs.

In one variation, the polynucleotide comprises a transcriptional regulatory element which is expressed preferentially in prostate cells (preferably in neoplastic and/or hyperplastic prostate cells) and which is used to drive the expression of an operably linked toxin gene encoding a cytotoxic or cytostatic gene product. The toxin gene is expressed in prostate cells which have incorporated the polynucleotide, thereby ablating said prostate cells. Delivery of such polynucleotides to neoplastic or hyperplastic prostate cells results in specific ablation of undesired prostate cells for therapy or prophylaxis of benign prostatic hypertrophy, prostate neoplasia, and the like.

In one embodiment, the invention provides a method for treating or preventing benign prostatic hypertrophy and prostate cancer. The method comprises delivering a polynucleotide consisting essentially of toxin gene operably linked to a prostate-specific transcriptional regulatory element (i.e., promoter and/or enhancer) which is/are preferentially transcriptionally active in neoplastic or hyperplastic prostate cells. A preferred transcriptional regulatory element is a segment upstream of the prostate-specific antigen (PSA) gene which confers prostate-specific expression of a cis-linked gene sequence when transfected into cell expressing PSA. The segment of interest is encompassed in an upstream segment from the transcription initiation site of less than about 10 kbp. Commonly, the upstream segment comprises an approximately 6.0, particularly 5.3 kb, segment immediately upstream from the major PSA transcription initiation site, beginning at +16, particularly 0; often the 5.3 kb segment is conveniently isolated as a XbaI-HindIII fragment. In the method, the polynucleotide construct is typically delivered to prostate tissues (e.g., a prostate tumor mass) as dsDNA, either as naked DNA, as DNA-lipid complexes, by viral delivery, or the like.

In a variation of the invention, a prostate-specific transcriptional regulatory element is operably linked to a gene for use in a cell comprising the appropriate transcription factors, the gene encoding an RNA which may have activity of interest, e.g. antisense, telomerase modulator, ribosome modulator, etc., or may exress a protein, such as an immunogenic antigen which is highly visible to the immune system (i.e., readily identified by and reacted against by cytotoxic immune cells). Cells expressing the antigen are hereby rendered susceptible to ablation by, for example, natural killer (NK) cells and the like. Frequently, the antigen is a human immunoglobin V$\kappa$ region, SV40 large T antigen, or spike glycoproteins of enveloped viruses (e.g., glycoprotein H of human cytomegalovirus (hCMV). Such polynucleotides can be used to advantage for treating prostate hypertrophy and/or prostatic aplasia by eliciting an immune response against the tumor cells which incorporate and express the cis-linked antigen gene. The invention also provides a method of treating prostatic hypertrophy and prostatic neoplasia by administering a polynucleotide comprising a PSA gene transcriptional regulatory element operably linked to an antigen gene (e.g., immunoglobin V$\kappa$ region, SV40 large T).

In another aspect of the invention are provided polynucleotides comprising a prostate-specific gene transcriptional regulatory element operably linked to a gene encoding a lymphokine which activates an anti-tumor immune response (e.g., increased NK activity). Typically, such activating lymphokines include but are not limited to: IL-1, IL-2, IL-12, GM-CSF, IFN$\alpha$, IFN$\beta$, IFN$\gamma$, and the like. Frequently, the transcriptional regulatory element is a PSA gene promoter/enhancer. Polynucleotide constructs comprising a prostate-specific gene transcriptional regulatory element operably linked to an activating lymphokine gene are introduced into hypertrophic prostate cells or neoplastic prostate cells whereupon the prostate cells express the lymphokine and thereby enhance an immune reaction against the hypertrophic or neoplastic prostate cells. The invention also provides a method for treating prostate hypertrophy and prostate neoplasia, said method comprising delivering such a polynucleotide construct which expresses an activating lymphokine in prostate cells (e.g., cells expressing PSA). Typically, the step of delivering the polynucleotide construct is accomplished by direct administration of the construct in the form of naked DNA, lipid-DNA complexes, as condensed DNA bound by a polycation and optionally also a ligand for a prostate cell receptor (e.g., FGF receptor), or as viral-packaged DNA. Alternatively, hypertrophic or neoplastic prostate cells can be explanted from a patient, transfected with such a polynucleotide construct, and reintroduced into the patient (typically at the site of explant) to elicit an immune response in the patient against his own prostate tumor.

The invention also provides non-human animals harboring a transgene comprising a prostate-specific transcriptional regulatory element operably linked to a structural gene. Such transgenic animals express the structural gene in prostate cells. Frequently, the prostate-specific transcriptional regulatory element comprises a 5.3 kb immediate upstream region of the human PSA gene, or portions thereof, and the structural gene is expressed in cells which express an endogenous PSA gene. A variety of structural genes can be selected for operable linkage to the prostate-specific promoter/enhancer in the transgene. Advantageously, an activated oncogene or large T antigen gene can be selected as the structural gene, whereupon the transgenic animal can have an increased propensity for developing prostate neoplasia and serve as a disease model for BPH and prostatic carcinoma.

The invention also provides a method for purifying prostate-specific transcription factors, the method comprising contacting cell extracts (typically nuclear extracts) from prostate cells (e.g., a prostate tumor cell line) with DNA comprising a prostate-specific transcriptional regulatory element (e.g., a 5.3 kb segment immediately upstream of the human PSA gene). The step of contacting is typically performed under suitable conditions for specific binding of the transcription factor(s) to the recognition site(s) on the DNA, whereupon unbound material is removed by washing and the retained material containing the transcription factor(s) is recovered. Transcription factors present in prostate tissue and absent in other tissues are identified as prostate-specific transcription factors.

BRIEF DESCRIPTION OF THE FIGURES

FIG. 15 is a diagram of constructs of truncated PSE and the PSA promoter indicating the length of the construct and the cells in which the constructs are active relative to the absence of the enhancer and the full promoter region.

DEFINITIONS

Figure 1:
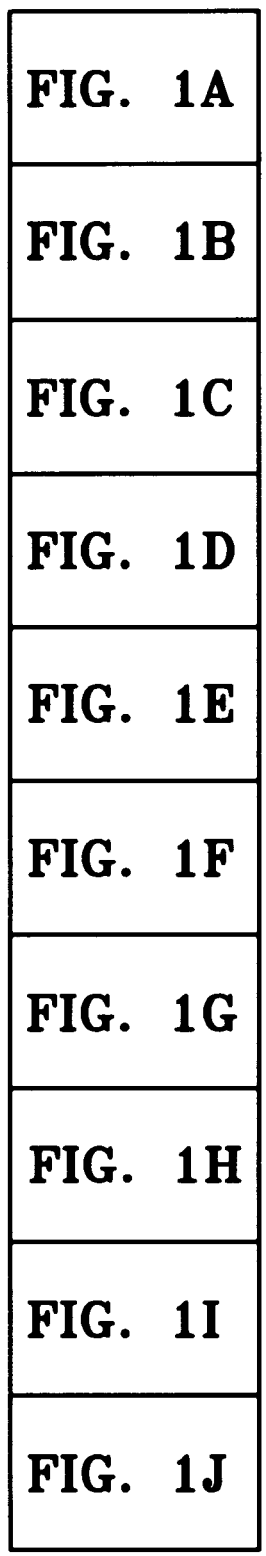
FIG. 1 shows the sequence of the 5' flanking region of the human prostate specific antigen to −5824 bp. (SEQ ID NO:01). The fragment runs from a HindIII site at −5824 bp to the HindIII site at +7 bp. The numbering system is +1 at the transcription start site of PSA mRNA (Lundwall, A., 1989, Characterization of the gene for Prostate-specific antigen, a human glandular kallikrein. Biochim. Biophys. Res. Commun. 161:1151–1159). The coding region of PSA starts at +42.
Figure 1:

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

The terms "substantially corresponds to", "substantially homologous", or "substantial identity" as used herein denotes a characteristic of a nucleic acid sequence, wherein a nucleic acid sequence has at least about 70 percent sequence identity as compared to a reference sequence, typically at least about 85 percent sequence identity, and preferably at least about 95 percent sequence identity as compared to a reference sequence, often at least 99 percent identical. The percentage of sequence identity is calculated excluding small deletions or additions which total less than 25 percent of the reference sequence. The reference sequence may be a subset of a larger sequence, such as a portion of a gene or flanking sequence, or a repetitive portion of a chromosome. However, the reference sequence is at least 18 nucleotides long, typically at least about 30 nucleotides long, and preferably at least about 50 to 100 nucleotides long. Desirably the extent of similarity between the two sequences will be at least about 80%, preferably at least about 90%, in accordance with the FASTA program analysis. (Pearson and Lipman, Proc. Natl. Acad. Sci. USA (1988) 85:2444–8))

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. As used herein, laboratory strains of rodents which may have been selectively bred according to classical genetics are considered naturally-occurring animals.

As used herein, a "heterologous" is defined in relation to a predetermined referenced gene sequence. For example, with respect to a structural gene sequence, a heterologous promoter is defined as a promoter which does not naturally occur adjacent to the referenced structural gene, but which is positioned by laboratory manipulation. For illustration, an SV40 large T antigen promoter is heterologous with respect to any gene other than large T antigen.

The term "transcriptional enhancement" is used herein to refer to functional property of producing an increase in the rate of transcription of linked sequences that contain a functional promoter.

As used herein, the term "transcriptional regulatory element" refers to a DNA sequence which activates transcription alone or in combination with one or more other DNA sequences. A transcriptional regulatory element can, for example, comprise a promoter, response element, negative regulatory element, and/or enhancer.

As used herein, a "transcription factor recognition site" and a "transcription factor binding site" refer to a polynucleotide sequence(s) or sequence motif(s) which are identified as being sites for the sequence-specific interaction of one or more transcription factors, frequently taking the form of direct protein-DNA binding. Typically, transcription factor binding sites can be identified by DNA footprinting, gel mobility shift assays, and the like, and/or can be predicted on the basis of known consensus sequence motifs, or by other methods known to those of skill in the art. For example and not to limit the invention, eukaryotic transcription factors include, but are not limited to: NFAT, AP1, AP-2, Sp1, OCT-I, OCT-2, OAP, NFKB, CREB, CTF, TFIIA, TFIIB, TFIID, Pit-I, C/EBP, SRF (Mitchell PJ and Tijan R (1989) Science 245: 371). For purposes of the invention, steroid receptors, RNA polymerases, and other proteins that interact with DNA in a sequence-specific manner and exert transcriptional regulatory effects are considered transcription factors. In the context of the present invention, binding sites for prostate-specific transcription factors (or prostate-specific transcription complexes) are often included in the prostate-specific transcriptional regulatory element (s).

As used herein, the term "operably linked" refers to a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the DNA sequences being linked are typically contiguous and, where necessary to join two protein coding regions, contiguous and in reading frame. However, since enhancers generally function when separated from the promoter by several kilobases and intronic sequences may be of variable lengths, some polynucleotide elements may be operably linked but not contiguous.

As used herein, the term "transcriptional unit" or "transcriptional complex" refers to a polynucleotide sequence that comprises a structural gene (exons), a cis-acting linked promoter and other cis-acting sequences necessary for efficient transcription of the structural sequences, distal regulatory elements necessary for appropriate tissue-specific and developmental transcription of the structural sequences, and additional cis sequences important for efficient transcription and translation (e.g., polyadenylation site, mRNA stability controlling sequences).

Unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' of the 5' end of the RNA transcript are referred to as "upstream sequences"; sequence regions on the DNA strand having the same sequence as the RNA and which are 3' to the 3' end of the RNA transcript are referred to as "downstream sequences".

As used herein, the term "toxin gene" refers to a polynucleotide sequence which encodes a polypeptide that, when expressed in a eukaryotic cell, typically a mammalian cell, kills the cell or causes the cell to exhibit apoptosis, cytostasis, senescence, or a block in expressing a differentiated function such as expression of a cell-type specific protein, and in one or more of these ways ablates a cell subpopulation. Preferred toxin genes of the invention are: diphtheria toxin A-chain gene (DTA), ricin A chain gene (Ric), herpesvirus thymidine kinase gene (tk), and Pseudomonas exotoxin gene (PE). Other suitable toxin genes will be apparent to those of skill in the art, such as suitable nucleases and proteases that, hen expressed intracellularly as cytoplasmic proteins, lead to cell death. Alternatively, genes encoding a defective mutant of an essential cell protein (e.g., a housekeeping gene such as GAPDH) may kill cells by acting as competitive or non-competitive inhibitors of the cognate normal protein (s). As used herein, the term "mutein" refers to a mutationally altered biologically active protein that retains the activity of the parent analog but comprises at least one deviation in primary amino acid sequence as compared to the sequence of the parent analog (Glossary of Genetics and gytogenetics, 4th Ed., p.381, Springer-Verlag (1976), incorporated herein by reference). For example but not by way of limitation, a DTA mutein may comprise a primary amino acid sequence having sequence identity to a naturally-occurring DTA polypeptide except at a residue position where an amino acid substitution (typically conservative) has been made, and the DTA mutein possesses cytotoxic activity, albeit not necessarily the same specific activity as naturally-occurring DTA.

DETAILED DESCRIPTION

Generally, the nomenclature used hereafter and the laboratory procedures in cell culture, molecular genetics, and nucleic acid chemistry and hybridization described below are those well known and commonly employed in the art. Standard techniques are used for recombinant nucleic acid methods, polynucleotide synthesis, cell culture, and transgene incorporation (e.g., electroporation, micro-injection, Lipofection). Generally enzymatic reactions, oligonucleotide synthesis, and purification steps are performed according to the manufacturer's specifications. The techniques and procedures are generally performed according to conventional methods in the art and various general references which are provided throughout this document. The procedures therein are believed to be well known in the art and are provided for the convenience of the reader. All the information contained herein is incorporated herein by reference.

Chimeric targeted mice are derived according to Hogan, et al., *Manipulating the Mouse Embryo: A Laboratory Manual*, Cold Spring Harbor Laboratory (1988) and *Teratocarcinomas and Embryonic Stem Cells: A Practical Approach*, E. J. Robertson, ed., IRL Press, Washington, D.C., (1987) which are incorporated herein by reference.

Embryonic stem cells are manipulated according to published procedures (*Teratocarcinomas and Embryonic Stem Cells: A Practical Approach*, E. J. Robertson, ed., IRL Press, Washington, D.C. (1987); Zjilstra et al., *Nature* 342:435–438 (1989); and Schwartzberg et al., *Science* 246:799–803 (1989), each of which is incorporated herein by reference).

Oligonucleotides can be synthesized on an Applied Bio Systems oligonucleotide synthesizer according to specifications provided by the manufacturer.

Methods for PCR amplification are described in the art (*PCR Technology: Principles and Applications for DNA Amplification* ed. H A Erlich, Freeman Press, New York, N.Y. (1992); *PCR Protocols: A Guide to Methods and Applications*, eds. Innis, Gelfland, Snisky, and White, Academic Press, San Diego, Calif. (1990); Mattila et al. (1991) *Nucleic Acids Res*. 19: 4967; Eckert, K. A. and Kunkel, T. A. (1991) *PCR Methods and Applications* 1: 17; *PCR*, eds. McPherson, Quirkes, and Taylor, IRL Press, Oxford; and U.S. Pat. No. 4,683,202, which are incorporated herein by reference).

Methods for electrophoretic mobility assays may be found in Abmayr, S M and Workman, J L (1994) in Current Protocols in Molecular Biology (Ausubel F M, Brent R, Kingston R E, Moore J G, Seidman J G, Smith J A, and Struhl K, eds) Vol. 2, pp.12.1.1–12.1.9, John Wiley & Sons, N.Y.; Dignam et al. (1983) Nucleic Acids Res. 11, 1475–1489 and Schuur et al. (1993) Cell Growth & Differ. 4, 761–768.

The existence of tissue/organ-specific transcriptional regulatory elements, e.g. enhancers/promoters, provides the opportunity for targeting anti-cancer agents to the specific organ where cancer has arisen. This can be done by (a) introducing into cells genes that provide for transcription of a product that can result in ablation of the cells in which the product is transcribed, e.g. genes that. encode highly toxic proteins or viruses which are cell specific for proliferation and lysis of cells, and (b) controlling the expression of such genes or proliferation of such viruses with highly specific enhancers/promoters. Thus, only cells of one particular site, that in which cancer has arisen, will be killed. The therapeutic ratio could improve from 1.5: 1 to 10:1 or more.

Identification of Prostate-Specific Transcriptional Regulatory Elements

DNA sequences within or flanking a gene which is preferentially expressed in prostate cells contain DNA sequence motifs which function to enhance or drive transcription of the cis-linked gene in prostate cells. These sequences are termed prostate-specific transcriptional regulatory sequences. Such sequences are isolated and evaluated for their capacity to enhance or drive transcription of an operably linked reporter gene (e.g., CAT) in prostate cells and substantially not in other cell types. Minimal functional sequences are defined by deletion analysis and/or linker-scanning mutagenesis and the like, followed by assay of transcriptional activity demonstrating transcription in transfected prostate cells but not in other cell types which have also been transfected with minimal reporter constructs.

A preferred prostate-specific transcriptional regulatory element is contained on the approximately 5.3 kb upstream flanking region of the human PSA gene. This 5.3 kb segment typically is represented by a XbaI-HindIII fragment which is isolated from a human genomic clone library probed with a PSA-specific nucleotide probe (e.g., a PSA cDNA sequence). Of particular interest in this fragment is the region from about −5300 to −2800, particularly −5322 to −2851 by itself or in combination with the region −541 to 0, as well as functional fragments thereof, e.g. the transcription factor binding sequences and response elements encompassed therein, individually or in combination.

A prostate-specific transcriptional regulatory element can comprise a promoter and/or enhancer. For example, a PSA enhancer is identified by deletion analysis of the PSA upstream region between −5.3 kb and −2.8 kb (infra), which typically can be isolated from the human genome as a XbaI-ApaI 2.5 kb fragment; this enhancer is termed the "upstream PSA enhancer." optionally, the naturally-occurring PSA promoter spanning the segment from about −541 to +12, particularly −320 to +12 of the human PSA gene can be included in operable linkage with the upstream PSA enhancer. This region includes an androgen response element. Alternatively, a heterologous promoter can be operably linked to the PSA upstream enhancer and used to drive expression of an operably linked structural gene sequence (e.g., a toxin gene, reporter gene, or other encoding sequence). Various deletions and point mutations can be made to the upstream sequences of the PSA gene, and each variant evaluated for the ability to drive or enhance transcription of a reporter gene (e.g., CAT) in neoplastic prostate cells (e.g., LNCaP) and for substantially lacking expression in non-prostatic cell types (e.g., NIH3T3, HBL100, HT1149, AR42J, NIH OVCAR-3, 293, or DU145, a human prostate cancer cell line that fails to synthesize PSA).

The enhancer portion of the sequence may be further refined by truncation at the 5' and/or 3' (in the direction of transcription) termini or by preparing fragments of the sequence and using electrophoretic mobility shift assays with a lysate of a PSA expressing cell in comparison with a control cell which does not express PSA, determining which fragments bind to proteins in the lysate of the PSA expressing cell as compared to the PSA non-expressing cell. In the former case, the 5' border of the upstream element is defined as being within 108 bp of the XbaI site (downstream from the XbaI site). The 3' border lies between the ClaI site at −4136 and −3738.

The following table provides the oligosequences which were found to bind in the EMSA experiments described in the Experimental section.

| oligo | 5' end | 3' end | LNCaP | MCF-7 |
| --- | --- | --- | --- | --- |
| 1 | −5443 | −5265 | + | + |
| 2 | −5300 | −5178 | + | + |
| 3 | −5203 | −5063 | + | + |
| 4 | −5120 | −4952 | − | − |
| 5 | −4980 | −4797 | + | − |
| 6 | −4847 | −4688 | − | − |
| 7 | −4710 | −4604 | + | − |
| 8 | −4636 | −4479 | + | − |
| 9 | −4588 | −4407 | + | + |
| 10 | −4424 | −4317 | + | + |
| 11 | −4336 | −4196 | + | + |
| 12 | −4224 | −4119 | + | + |
| 13 | −4168 | −4054 | + | − |
| 14 | −4076 | −3945 | + | − |
| 15 | −3968 | −3801 | + | − |
| 16 | −3825 | −3739 | − | − |

As is evident from the above table, segments of the enhancer sequence which are found to bind transcription factors present in PSA producing cells include segments spanning −4980 to −4797; −4710 to −4479; and −4168 to −3801, which includes AREs at −4148 to −4000 (GGTACAnnnTGTT/CCT) (SEQ ID NO:3). The segments which may find use will range in size from about 50 to 250 bp, with individual regions requiring greater or lesser numbers of base pairs. In addition, segments which formed complexes with proteins from prostate cells which did not produce PSA, as well as with cells that produce PSA include segments spanning −5500 to −5000, and −4600 to −4000. Segments that did not bind to proteins from either lysate include segments spanning −5150 to −4950, −4850 to −4680 and −3850 to −3700. None of the oligonucleotide probes solely reacted with proteins from the MCF-7 lysate For the purposes of the subject invention those segments which do not bind to proteins from the LNCaP lysate serve as spacers and may be mutated, although except in special circumstances where one wished to have a specific sequence at that position, for example, a polylinker or a reduction in size of the construct or the like, there would be little point in modifying the sequence.

These segments are of interest in identifying proteins associated with transcriptional regulation of the PSA gene. With these segments lysates may be titrated for binding proteins and differentiated cells may be analyzed for the presence of common transcription factors. Recognition of the different transcription factors associated with the transcription of PSA and their role in other cells can serve to explain the development of cancer in prostate cells and lead to new therapies. In addition, the sequences may be used as decoys to inhibit the transcription factor binding to the PSE enhancer, so as to determine the degree to which the transcription factor plays a role in the regulation of PSA gene transcription. The segments can also be used in conjunction with segments from other enhancers to modify the transcriptional regulation of genes in novel ways.

Having identified the binding sequences mutational analysis is carried out to identify specific nucleotides which are essential or non-essential to the binding of the transcription factors. This can be readily achieved using PCR and providing for nucleotide degeneracy at one or more sites in the primer homologous to the target site to be mutagenized. Modifications may then be made which serve to enhance the binding affinity of the transcription factor to the mutated sequence to increase the induction in PSA expressing cells as compared to PSA non-expressing cells or the like. Since elements having the androgen response element sequence are present in the sequences which provide for PSA gene expression specificity, the role of the androgen receptor in the coregulated transcription of genes regulated by the androgen receptor may be analyzed in relation to the expression of PSA and cancer neoplasia initiation.

ANTI-PROLIFERATION CONSTRUCTS

Toxin Gene Constructs

The polynucleotide sequence encoding a toxin molecule is operably linked to cis-acting transcriptional regulatory sequences (e.g., promoter, enhancer, or functional portion thereof) of a prostate-specific gene (e.g., PSA), so that the toxin protein is expressed in prostate cells in a manner similar to the expression of the endogenous prostate-specific gene in naturally-occurring prostate cells, preferably neoplastic prostate cells. Thus, it is usually preferable to operably link a toxin-encoding sequence to transcriptional regulatory elements which naturally occur in or near the prostate-specific gene (e.g., PSA gene).

The operable linkage may be formed by homologous sequence targeting to replace the toxin gene downstream of (i.e., towards the carboxy-terminus of the encoded naturally-occurring polypeptide in translational reading frame orientation) a transcriptional regulatory sequence (i.e., a promoter and the additional elements which confer specific cell-type expression) of the endogenous prostate-specific gene.

Alternatively, the operable linkage may be formed exogenously as a transgene, wherein the toxin gene is operably linked to a transcriptional regulatory sequence isolated from an endogenous prostate-specific gene, typically by genomic DNA cloning. In such transgenes, the transcriptional regulatory sequence is at least the minimal sequence(s) required for efficient cell-type specific expression, which generally is at least a promoter and at least about 0.2 kilobase (kb) upstream of the promoter, preferably at least about 1 to 3 kb upstream of the promoter, more preferably at least about 5 kb upstream of the promoter, and frequently at least about 8 or more kb upstream of the promoter. In the case of the PSA gene, at least a functional promoter and the PSA upstream enhancer are combined to confer prostate-specific expression of operably linked structural gene (toxin gene) sequences. Frequently, sequences downstream of the promoter, especially intronic sequences, are included in the transgene constructs (Brinster et 31. (1988) *Proc. Natl. Acad. Sci. (U.S.A.)* 85: 836, incorporated herein by reference). Usually the sequences upstream of the promoter are used contiguously, although various deletions and rearrangements can be employed. Some desired regulatory elements (e.g., enhancers, silencers) may be relatively position-insensitive, so that the regulatory element will function correctly even if positioned differently in a transgene than in the corresponding germline gene. For example, an enhancer may be located at a different distance from a promoter, in a different orientation, and/or in a different linear order. For example, an enhancer that is located 3' to a promoter in germline configuration might be located 5' to the promoter in a transgene and in the naturally occurring or inverted order. Where convenient, it is preferred that a contiguous segment of genomic DNA sequence spanning the prostate-specific gene and containing as much upstream flanking sequence as convenient (typically at least about 1–10 kb) be used in the transgene or targeting construct, with the toxin gene inserted so as to replace or displace at least the first intron of the gene and to be operably linked to the promoter (s). It is further recognized that a prostate-specific gene may comprise multiple promoters, which may individually be cell type-specific, and it is necessary to operably link the toxin gene to at least one promoter (or other transcriptional element) which confers transcription in prostate (especially neoplastic prostate) cells. Transcriptional elements which confer transcription in non-prostate cells and which are not necessary for efficient transcription in prostate cells may be advantageously deleted from the transgene or targeting construct to provide additional cell-type specificity for ablating prostate cells and minimizing ablation of other cell types.

If the transcription regulatory sequence(s) selected are relatively inefficient in transcribing the toxin gene, it may be desirable to incorporate multiple copies of a transgene or targeting construct to compensate with an enhanced gene dosage of the transgene.

Toxin Genes

The toxin genes may be toxic independently of any ancillary agent or toxic only in conjunction with an ancillary agent. There are numerous natural toxins which result in cell death upon reaching a minimum intracellular concentration. Other toxic agents induce cell death in conjunction with a second agent, but are otherwise benign. Illustrative of this latter protein is thymidine kinase.

Several polynucleotide sequences are suitable for use as a toxin gene in the transgenes and targeting constructs of the invention. Preferred toxin genes are: diphtheria toxin A chain gene (Palmiter et al. (1987) op.cit. and erratum (1990) *Cell* 62: following p.608; Maxwell et al. (1987) *Mol. Cell. Biol.* 7: 1576; Behringer et al. (1988) op.cit.; Messing et al. (1992) op.cit., incorporated herein by reference), ricin A chain gene (Piatak et al. (1988) *J. Biol. Chem.* 263: 4837; Lamb et al. (1985) *Eur. J. Biochem.* 148: 265; Frankel et al. (1989) *Mol. Cell. Biol.* 9: 415, incorporated herein by reference), Pseudomonas exotoxin gene comprising at least domain III or amino acids 400–600 (Hwang et al. (1987) *Cell* 48: 129; Siegall et al. (1989) *J. Biol. Chem.* 264: 14256; Chaudhary et al. (1990) *Proc. Natl. Acad. Sci. (U.S.A.)* 87: 308, incorporated herein by reference), and the HSV tk gene (Zjilstra et al. (1989) *Nature* 342:435; Mansour et al. (1988) *Nature* 336: 348; Johnson et al. (1989) *Science* 245: 1234: Adair et al. (1989) *Proc. Natl. Acad. Sci (U.S.A.)* 86: 4574; Capecchi, M. (1989) *Science* 244:1288, incorporated herein by reference).

The DTA, Ric, and PE act directly to kill cells in which they are expressed. The HSV tk gene requires the presence of a negative selection agent such as gancyclovir to effect toxicity in vivo. Generally, the dosage of gancyclovir is calibrated by generating a standard dose-response curve and determining the dosage level at which a desired level of ablation of prostate cells is observed. Information regarding administration of gancyclovir (GANC) to animals is available in various sources in the art, including human prescribing directions from package inserts. When used in cell culture, a selective concentration of gancyclovir is typically about 1 $\mu$M, with about 0.2 $\mu$M used for in vitro applications and about 1–5 $\mu$M administered for in vivo applications (typically administered over about 24 hours by continuous infusion from an osmotic pump loaded with 125 mg/ml of gancyclovir in aqueous solution).

Various other toxin genes may be used in the discretion of the practitioner and may include mutated or truncated forms of naturally-occurring proteins which competitively or non-competitively inhibit the correct functioning of the naturally-occurring forms and thereby kill the cell. Alternatively, a toxin gene may comprise a polynucleotide that encodes an engineered cytoplasmic variant of a potent nuclease (e.g., RNase A) or protease (e.g., trypsin, chymotrypsin, proteinase K, etc.) which, when expressed as an enzymatically active polypeptide in the cytoplasm of a cell, produces the death of the cell (as determined, for example, by exclusion of Trypan Blue dye). Alternatively, a toxin gene may comprise a gene that, when expressed in a cytotoxic cell type, causes apoptosis (programmed cell death) of that cell type.

Antigen and Lymphokine Genes

For embodiments where a toxin gene is not employed, one variation of the invention comprises forming an expression polynucleotide by operably linking a prostate-specific transcriptional regulatory element with a structural gene encoding a lymphokine or an antigen which potentiates or elicits an immune response directed against cells expressing said lymphokine or antigen. Typically, a DNA segment comprising a PSA upstream enhancer and promoter are operably linked to the structural gene, forming an expression construct. Typical lymphokine genes are exemplified by, but not limited to, the following: IL-I, IL-2, IL-12, GM-CSF, IFN$\alpha$, IFN$\beta$, and IFN$\gamma$. Typical antigen genes are those which are immunogenic and can be exemplified by, for example, immunoglobin $\kappa$V region and SV40 large T antigen (Watanabe et al. (1993) *J. Immunol.* 151: 2871, incorporated herein by reference). In one embodiment, a DNA-mediated tumor vaccine where a prostate specific enhancer drives a highly visible antigen such as the immunoglobin $\kappa$V region of human IgG or SV40 T antigen is used to treat prostate neoplasia. Tumor vaccines of this nature can elicit natural killer cells to ablate any remaining tumor cells. Prostate cells expressing PSA would now become immunogenic and visible to the immune system. These therapies can also be delivered as described for transrectal fine needle biopsy (infra).

Viral Genes

The subject enhancers can be used to regulate essential genes of viruses. The modified viruses will then be limited in their ability to proliferate to those cells which have the specific transcription factors necessary for transcription of the essential gene(s). In this way cells can be preferentially lysed in mixtures of cells in vitro and in vivo. For example, cancerous cells may be specifically targeted for viral proliferation, where the cancerous cells have the necessary transcription factors for transcription of the essential gene(s) under the transcriptional control of the cell lineage enhancer or enhancer specifically associated with cancerous cells.

By way of illustration, adenovirus may be modified by providing for early genes, e.g. E1A, E1B, E2, E3 and E4, being under the transcriptional regulation of the PSE. See, U.S. application Ser. No. 08/669,753, whose disclosure is incorporated herein by reference. By replacing the naturally occurring viral transcriptional regulatory region with a transcriptional regulatory region comprising an enhancer, either naturally occurring or modified, in conjunction with a promoter, either the wild-type promoter associated with the enhancer or a promoter associated with a different gene one can provide for cell specific proliferation.

Anti-sense Sequences

Instead of having a gene encoding a protein, one may have an antisense sequence of at least about 30 bp, usually at least about 50 bp, having as a target the coding region of an essential gene for the proliferation or viability of the host. Numerous proteins associated with transcription, translation, metabolic pathways, cytostructural genes, or the like may be the target of the antisense. Desirably, the target should be essential, present at relatively low levels, and particularly associated with neoplastic cells. Of particular interest would be transcription factors associated with genes necessary for proliferation, e.g. oncogenes, or cytoskeleton genes, e.g. β-actin and tubulin, etc.

In the usual context, the antisense gene may be synthesized in accordance with conventional ways, using manual synthesis or automated synthesizers. In the context of PSE, the PSE would be operably linked to encode an antisense construct such that the transcription of the antisense would only occur in cells in which the PSE is active.

Transcriptional Regulatory Sequences

Transgenes and expression polynucleotides of the invention comprise a transcriptional regulatory sequence of a prostate-specific gene operably linked to a toxin gene or other structural gene (e.g., activating lymphokine or immunogenic antigen), or any gene of interest, whether encoding a protein or an RNA sequence having a function of interest, and targeting constructs of the invention may comprise such a transcriptional regulatory sequence. Suitable transcriptional regulatory sequences are those which confer prostate-specific transcription of the linked gene, although low levels of transcription may occur in other cell types as well so long as such non-prostate cell expression does not substantially interfere with the health and prognosis of patients treated with the transgenes/expression polynucleotides.

Suitable transcriptional regulatory sequences of the invention generally are derived from or correspond to polynucleotide sequences within or flanking a gene which is preferentially expressed in a neoplastic prostate cell population. Various prostate-specific genes are suitable, and specific genes may be selected at the discretion of the practitioner. For example, genes which have prostate-specific transcriptional regulatory sequences include prostatic acid phosphatase (PAP); and the genes encoding anitgens which are detected by the monoclonal antibodies TURP-27, Leu 7, 7E 11-C5, and PD41 (Wright et al. (1990) *The Prostate* 17: 301). For many intended purposes, the human PSA gene is the preferred suitable source for obtaining prostate-specific transcription regulatory sequences.

The human PSA gene has been cloned and characterized by sequencing (Lundwall A (1989) op.cit; Riegman et al. (1991) *Molec. Endocrinol.* 5:1921, incorporated herein by reference). A toxin gene or other structural gene is preferably inserted in operable linkage with the PSA gene upstream enhancer (and optionally including the PSA promoter). The toxin gene (or other structural gene) is positioned to ensure correct transcription and translation according to standard cloning methods in the art. A targeting construct may be produced having recombinogenic homology regions flanking the toxin gene (or other structural gene) which correspond to the sequences flanking the chosen insertion site, which will be downstream of the transcription start site. A transgene comprising the regulatory sequences identified herein as the PSA upstream enhancer may also be produced, however it may be desirable to include additional sequences upstream or downstream of the PSA upstream enhancer; such sequences can be readily isolated by routine "chromosome walking" screening of a human genomic library.

Decoys

The PSE region may also serve to be used as decoys, where dsDNA is introduced into the target cells by any convenient means as described previously. The dsDNA may be synthesized from naturally occurring nucleotides or unnatural nucleotides, so long as the dsDNA will bind to the target transcription factor. By introducing decoys into the prostate cells, the transcription factors binding to the PSE will be diverted to the decoys, so that PSA and other genes requiring the transcription factor(s) regulating PSA will be diverted. This will serve to identify those genes which are coordinately regulated with PSA and can also serve to modulate the viability and growth of prostate cells.

By having segment sequences of the enhancer region which are involved with binding transcription factors, one or more of the segments may be joined together, where the segments may be naturally occurring or mutated while retaining competitive binding capability with the natural sequence, and used as decoys. This will serve to further refine the function of the various sequences and indicate what other genes are coregulated with the particular enhancer.

DNA DELIVERY METHODOLOGIES

A large number of methodologies for DNA delivery have been developed and new ones are continuing to be developed. The presently available methodologies may be divided into three major groups: transfection with a viral vector; fusion with a lipid; and cationic supported DNA introduction. Each of these techniques has advantages and disadvantages, so that the selection of which technique to use will depend upon the particular situation and its demands. In some situations, disadvantages may prove to be advantages and it is not necessary to have an ideal delivery system, so long as it gets the work done without being unduly detrimental to the patient's recovery.

DNA Delivery to Prostate Cells and Prostatic Carcinoma Cells

Delivery of the polynucleotide constructs of the invention to prostate cells, especially neoplastic prostate cells, can be accomplished by any suitable art-known method.

The invention provides methods and compositions for transferring such expression constructs, transgenes, and homologous recombination constructs into cells, especially in vivo for gene therapy of prostate disease. It is also an object of the invention to provide compositions for the therapy of BPH and prostatic neoplastic diseases.

For gene therapy of such diseases to be practicable, it is desirable to employ a DNA transfer method that accomplishes the following objectives: (1) is capable of directing the therapeutic polynucleotides into specific target cell types (e.g., neoplastic cells, prostate cells), (2) is highly efficient in mediating uptake of the therapeutic polynucleotide into the target cell population, and (3) is suited for use in vivo for therapeutic application.

So far, the majority of the approved gene transfer trials in the United States rely on replication-defective retroviral vectors harboring a therapeutic polynucleotide sequence as part of the retroviral genome (Miller et al. (1990) *Mol. Cell. Biol.* 10: 4239; Kolberg R (1992) *J. NIH Res.* 4: 43; Cornetta et al. (1991) *Hum. Gene Ther.* 2: 215). The major advantages of retroviral vectors for gene therapy are: the high efficiency of gene transfer into replicating cells, the integration of the transferred genes into cellular DNA, and the lack of further spread of the sequences after gene transduction. Major disadvantages include the inability of retroviral vectors to infect nondividing cells, the inherent inability to characterize completely the retroviral vectors used for gene transduction because retroviral vectors cannot be made synthetically but rather must be produced by infected cultured cells, the inability to target distinct cell types selectively, and the potential for undesirable insertional mutagenesis of the host cell genome, among other problems.

Adenoviral vectors have also been described for potential use in human gene therapy (Rosenfeld et al. (1992) *Cell* 68: 143). The advantages and disadvantages of the use of adenovirus vectors will depend on the manner in which they are used. In some instances, a disdvantage may be an advantage and vice versa. In the case of target cell intracellular expression, major advantages of adenovirus vectors are their potential to carry larger insert polynucleotide sequences than retroviral vectors, very high viral titres, ability to infect non-replicating cells, and suitability for infecting tissues in situ, especially in the lung. Major disadvantages are the inclusion of many adenovirus genes in the vectors which encode viral proteins that are immunogenic or have other adverse effects (e.g., cytopathic penton proteins), and potential instability of gene expression because the virus does not integrate stably into chromosomal DNA. These disadvantages are advantageous if one is controlling viral proliferation in a cell with a cell specific enhancer.

Moreover, because of their inherent antigenicity, most gene therapy methods employing viral vectors require additional treatments, e.g. immunosuppression, for multiple administrations, such as may be required to treat chronic diseases such as, for example, cancer.

The other gene transfer method that has been approved for use in humans is physical transfer of plasmid DNA in liposomes directly into tumor cells in situ. Unlike viral vectors which must be propagated in cultured cells, plasmid DNA can be purified to homogeneity and thus reduces the potential for pathogenic contamination. In some situations (e . g., tumor cells) it may not be necessary for the exogenous DNA to stably integrate into the transduced cell, since transient expression may suffice to kill the tumor cells. Liposome-mediated DNA transfer has been described by various investigators (Wang and Huang (1987) *Biochem. Biophys. Res. Commun.* 147: 980; Wang and Huang (1989) *Biochemistry* 28: 9508; Litzinger and Huang (1992) *Biochem. Biophys. Acta* 1113: 201; Gao and Huang (1991) *Biochem. Biophys. Res. Commun.* 179: 280; Felgner WO91/17424; WO91/16024). Unfortunately, liposomal compositions usually do not possess specificity for delivering the exogenous DNA to a predetermined cell type; liposomes are generally indiscriminate in fusing to a wide variety of cell types with approximately equal frequency and often require non-physiological pH conditions for efficient fusion.

Immunoliposomes have also been described as carriers of exogenous polynucleotides (Wang and Huang (1987) *Proc. Natl. Acad. Sci.* (*U.S.A.*) 84: 7851; Trubetskoy et al. (1992) *Biochem. Biophys. Acta* 1131: 311). Immunoliposomes hypothetically might be expected to have improved cell type specificity as compared to liposomes by virtue of the inclusion of specific antibodies which presumably bind to surface antigens on specific cell types. Unfortunately, antibodies frequently are cross-reactive and bind to a variety of proteins bearing cross-reactive epitopes. This might be expected to pose a particular problem when the antibody is raised against a cell surface antigen that is a member of a conserved gene family or a cell surface antigen that contains a conserved sequence present in many other cell surface proteins. Moreover, immunoglobulins which bind cell surface proteins may be inefficiently endocytosed and/or may cause premature disruption of the immunoliposome upon binding antigen, undesirably releasing the exogenous DNA from the immmunoliposome prior to fusion (Ho and Huang (1985) *J. Immunol.* 134: 4035). In addition, immunoliposome-DNA preparations are relatively inefficient for transfection.

Behr et al. (1989) *Proc. Natl. Acad. Sci.* (*U.S.A.*) 86: 6982 report using lipopolyamine as a reagent to mediate transfection itself, without the necessity of any additional phospholipid to form liposomes. However, lipopolyamines do not impart a predetermined targeting specificity to the exogenous DNA; for the most part, cells are transfected indiscriminately.

Low molecular weight polylysine ("PL") and other polycations have also been described as carriers to promote DNA-mediated transfection into cultured mammalian cells. Zhou et al. (1991) *Biochem. Biophys. Acta* 1065: 8 reports synthesis of a polylysine-phospholipid conjugate, a lipopolylysine comprising PL linked to N-glutarylphosphatidylethanolamine, which reportedly increases the transfection efficiency of DNA as compared to lipofectin, a commercially used transfection reagent. Unfortunately, a lipopolylysine does not provide satisfactory cell type specificity and it was reported by the authors to be quite inefficient in transforming cells in suspension.

Polylysine molecules conjugated to asialoorosomucoid ("ASOR") (Wu GY and Wu CH (1987) *J. Biol. Chem.* 262: 4429; Wu GY and Wu CH (1988) *Biochemistry* 27: 887; Wu GY and Wu CH (1988) *J. Biol. Chem.* 263: 14621; Wu GY and Wu CH (1992) 3 *Biol. Chem.* 267: 12436; Wu et al. (1991) *J. Biol. Chem.* 266: 14338; and Wilson et al. (1992) *J. Biol. Chem.* 267: 963, WO92/06180; WO92/05250; and WO91/17761) or transferrin (Wagner et al. (1990) *Proc. Natl. Acad. Sci.* (*U.S.A.*) 87: 3410; Zenke et al. (1990) Proc. Natl. Acad. Sci. (U.S.A.) 87: 3655; Birnstiel WO92/13570) have been described; such conjugates have been predicted to afford target-specific delivery of associated DNA to cells which express the appropriate receptor (i.e., asialoglycoprotein receptor or transferrin receptor, respectively). WO91/14696 describes covalently bound conjugates consisting of oligonucleotides in disulfide linkage to a targeting agent that promotes transport across cell membranes for transferring short antisense oligonucleotides into cells. Birnstiel, WO91/17773, describes polycation conjugates comprising a anti-CD4 antibody or a HIV gp120 fragment to confer targeting specificity for CD4+T cells. Similar methods can be used to specifically deliver DNA to prostate cells expressing a cell surface receptor which may be targeted with a ligand or a specific antibody reactive with the receptor. Although such methods increase the specificity of delivering the exogenous polynucleotides to a particular cell type, these methods often have a low transfection efficiency as compared to lipofection methods.

Liposome mediated transfection is highly efficient and generally not cell type specific, and lipid:DNA complexes rapidly associate with cells of the reticuloendothelial system (Mannino and Gould-Fogerite (1988) *BioTech* 6: 682). Receptor-mediated transfection theoretically should allow any size DNA or RNA to be transfected, however efficiency is affected by lysosomal degradation of nucleic acid. This has necessitated the use of inhibitors of lysosomal degradation, referred to a lysosomotropic agents, which are usually administered to cells contemporaneously (i.e., within about 1–6 hours prior to or subsequent to) transfection. Unfortunately cytotoxicity of most of these agents like chloroquine limits the universal employment of receptor mediated transfection (Dean et al. (1984) *Biochem. J.* 217: 27).

Essentially any suitable DNA delivery method can be used, although it is generally believed that direct physical application of naked DNA comprising the expression construct/transgene to the target cell population (e.g., prostate tumor mass) is believed to be preferred in many cases.

Therapeutic Method for Prostate Hypertrophy and Neoplasia

Prostate cancer and benign prostate hyperplasia can be treated, arrested, or prevented using gene therapy wherein a DNA construct which comprises a prostate-specific transcriptional regulatory element can be delivered to prostate cells for targeted expression of a gene.

The nucleic acid compositions can be stored and administered in a sterile physiologically acceptable carrier, where the nucleic acid is dispersed in conjunction with any agents which aid in the introduction of the DNA into cells. Various sterile solutions may be used for adminstration of the composition, including water, PBS, ethanol, lipids, etc. The concentration of the DNA will be sufficient to provide a therapeutic dose, which will depend on the efficiency of transport into the cells. Adminstration may be by syringe needle, trocar, cannula, catheter, etc., as a bolus, a plurality doses or extended infusion, etc. The dose may be administered intralesionally, intravascularly or other appropriate site.

The diphtheria A toxin gene is placed 3' to a prostate-specific enhancer, such as the PSA upstream enhancer. This DNA is delivered by direct injection of the DNA as naked DNA, as a liposome, or other lipofection complex and the like directly into a prostate tumor cell mass in an outpatient procedure analogous to a transrectal fine needle biopsy of the prostate using the Franzen needle. The fine needle biopsy is commonly used for differential diagnosis of BPH and prostate carcinoma as well as staging of prostate carcinoma. The fine needle injection of DNA as a therapeutic can be directed by index finger palpation of nodules, ultrasound, or rectal endoscope. It is possible to repeatedly inject DNA therapeutically with this modality. Frequently, it is preferable that delivery is accomplished by intravenous injection.

The compositions containing the present prostate-specific polynucleotides encoding a toxin or vaccine protein can be administered for prophylactic and/or therapeutic treatments. In therapeutic application, compositions are administered to a patient already affected by the particular neoplastic/hypertrophic prostate disease, in an amount sufficient to cure or at least partially arrest the condition and its complications. An amount adequate to accomplish this is defined as a "therapeutically effective dose" or "efficacious dose." Amounts effective for this use will depend upon the severity of the condition, the general state of the patient, and the route of administration.

EXPERIMENTAL EXAMPLES

Identification of a Tissue-Specific PSA Upstream Enhancer

The promoter of prostate-specific antigen has been reported (Riegman et al. (1991) op.cit, incorporated herein by reference). The promoter from –320 to +12 contains a TATA-box, a GC-box, and a hormonal response element at –170 to –156. However, transfection of CAT constructs from –1600 to +12 into human prostate LNCaP cells were reportedly unsuccessful. Indeed the functional domains described were found by cotransfecting the CAT constructs into monkey kidney COS cells with an androgen receptor expression plasmid. It was unclear from this work whether the lack of activity of CAT constructs in LNCaP cells was due to poor transfection efficiency or due to a lack of a suitable tissue-specific enhancer element (Reigman et al (1991) op.cit).

Figure 4:
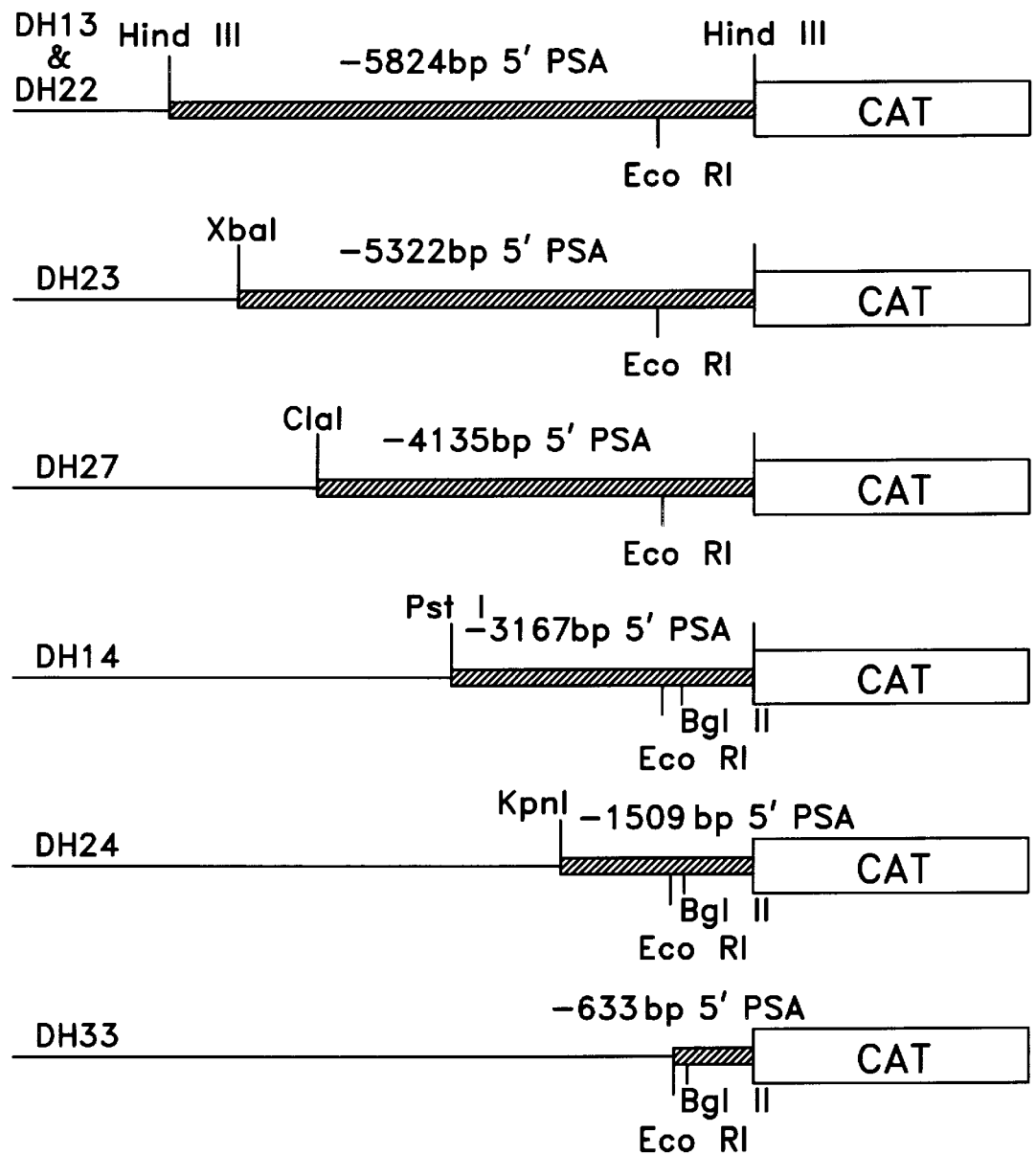
FIG. 4 shows expression constructs wherein various lengths of the region upstream of the human PSA gene are operably linked to a reporter gene, chloramphenicol acetyltransferase (CAT); these constructs were evaluated for transcriptional activity in transfected human prostate LNCaP cells.

A 6 kb fragment representing the 5' flanking region of the prostate specific antigen (PSA) gene which was isolated from a human genomic library in the phage vector Charon 4A was kindly provided by Lundwall (1989) op.cit. This represents a 6 kb fragment in a pUC18 backbone as a HindIII fragment. Restriction digest analysis of the 6 kb 5' flanking region of PSA provided the map of unique sites shown in FIG. 2. The ability of this 6 kb DNA fragment to drive CAT activity was tested by transfection of human prostate LNCaP cells (ATCC). LNCaP cells were plated at a density of $7 \times 10^5$ cells/6cm dish in 5 ml of RPMI 1640 supplemented with 10% fetal calf serum, 100 U each of penicillin and streptomycin. 24 hrs later cells were washed twice with 2 ml of phosphate buffered saline (PBS) and transfected gently with cationic liposomes. 15 ug of DNA mixed with 30 ug of Lipofectin (Gibco BRL) was added to 3 ml of serum free media/plate. After 24 hrs, the media was removed and replaced with 5 ml of RPMI 1640, 10 FCS. Cells were harvested after an additional incubation of 48 hrs. To prepare extracts, cells were washed twice with PBS, and removed with lml 150 mM NaCl, 50 mM Tris-HCl pH 7.4, 1 mM EDTA. Cells were collected by centrifugation and lysed by 3x freeze-thaw in 100 ul 0.25M Tris-HCl pH 7.4. Following centrifugation at 14,000 RPM, 4° C., 5', the supernatant was removed and stored at –20° C. CAT assays were performed on 50ug protein of cell extract. The clones shown in FIG. 4 were constructed containing various size deletions of the of the 6 kb 5' flanking region of the PSA gene. Constructs were either in pCAT Basic (Promega) or in pBS KSII+ (Stratagene). Constructs in either plasmid backbone performed substantially identically. To test these constructs, LNCaP cells were transfected with 15 ug DNA/ 733 $10^5$ cells in 6 cm dishes with Lipofectin. Lane 1 contained no DNA, lane 2=promoterless CAT, lane 3=–5824 bp 5' PSA CAT, lane 4=–5322 5' PSA CAT, lane 5 –4135 bp 5' PSA CAT, lane 6=–3167 bp 5' PSA CAT, lane 6=–1509 bp 5' PSA CAT, lane 7=–633 bp 5' PSA CAT.

Of these constructs only the full −5824 bp HindIII construct and the −5322 bp XbaI construct were found to be capable of driving CAT in human prostate LNCaP cells. Constructs of −4136 bp (a unique ClaI site), or less, were incapable of driving CAT in these cells. Thus, the putative PSA enhancer lies between −5322 bp and −4136 bp: between unique XbaI and ClaI sites and extending some base pairs 3' of the ClaI site as shown in the FIGS. 14 and 15. The XbaI-ClaI fragment of about 1.2 kb (SEQ ID NO:02) was transferred to pBSKSII+and sequenced using primers from the multiple cloning site and then synthesized primers. Both strands of DNA were sequenced using the Sanger dideoxy method. The sequence of this region is shown in the whole sequence of FIG. 1. (SEQ ID NO:01) This region can be conveniently cloned out of a human genomic DNA library or can be amplified by PCR from human genomic DNA, among other methods at the practitioner's discretion.

A computer search of GenBank showed no substantially related sequences to that of FIG. 1.(SEQ ID NO:01).

Prostate specific antigen has enjoyed widespread acceptance as a serum marker for benign hyperplasia and cancer of the prostate. While normal ranges of PSA are from 0 to 4.0 ng/ml, a single measurement of serum PSA levels is not prognostic of a disease condition. However, repeated measurements showing rising levels of PSA over 10 mg/ml and rapid rises within months are cause for serious concern. Such indications are followed by biopsy to determine if the rising PSA levels are due to benign hyperplasia, or prostate cancer. PSA has been shown to be synthesized exclusively in prostate tissue or metastases of neoplastic prostate tissue. Interestingly, to date all metastases of prostate cancer and primary cultures of prostate tissue synthesize PSA (Ghazizadeh et al. (1984) *Urol. Int.* 39: 9). Of great interest is the question of whether this putative PSA enhancer is tissue-specific. Specifically, does the enhancer direct CAT expression only in prostate tissues and not in other tissues? Table I shows in vitro transfection data of a variety of cell lines with the −6.0 kb 5' PSA flanking sequence driving CAT. LnCaP cells were transfected with Lipofectin. All other cells were transfected by the DEAE-dextran method.

TABLE I

Tissue Specificity of PSA Enhancer

| Cell Line | | CAT Activity |
| --- | --- | --- |
| human cancer prostate | LNCaP | + |
| mouse fibroblast | NIH3T3 | − |
| rat pancreas | AR42J | − |
| human kidney | 293 | − |
| human cancer ovary | NIH OVCAR-3 | − |
| human breast cancer | HBL100 | − |
| human cancer prostate | DU145 | − |
| human bladder cancer | HT1149 | − |

All transfections were negative for promoter less CAT and positive for CAT driven by the SV40 early promoter (SVCAT) with the exception of LNCaP which was also negative for SVCAT. The data in Table I show the putative PSA enhancer to be tissue-specific for prostate tissue that is actively expressing prostate specific antigen. It is interesting to note that DU145, a human prostate tumor line that does not express PSA, also fails to drive CAT from the PSA enhancer. However, tissue-specific expression of PSA is pathognomonic for BPH and prostate cancer questioning the value of PSA negative cell lines for the study of prostate disease. The bladder cell line was chosen since embryologically bladder is the closest relative of the prostate.

The PSA upstream prostate-specific enhancer can be used to form toxin gene expression polynucleotides for cytotoxic therapy of the prostate, for tumor vaccines of the prostate, as well as injection of gene delivery vehicle to target tumor metastases occurring in lymph nodes and bone.

Nude Mice Harboring Prostate-Specific Transgene

Traditionally, in vivo tissue-specificity of enhancers has been shown in transgenic mice. However, the construction of transgenic mice is only conclusive for enhancers which are functional in the mouse. To test the in vivo tissue specificity of the PSA upstream enhancer, a transgene comprising the human PSA upstream enhancer operably linked to the CAT gene driven by a heterologous promoter was injected into nude mice carrying the human prostate tumor LNCaP. 3–4 week-old male nude mice were injected subcutaneously in the back of the neck with 0.5 ml containing 0.25 ml Matrigel (Collaborative Biomedical) and 0.25 ml Dulbecco's MEM without fetal calf serum or antibiotics and containing $1 \times 10^6$ LNCaP cells at 4° C. Large tumors of about 0.5 to 1.0 grams developed within 4–5 weeks. Mice carrying tumors were injected I.V. into the tail vein with 100 μl containing 100 μg of a DNA expression construct including the PSA upstream enhancer and PSA promoter driving the CAT gene, 0.5% dextrose, and 800 ng of DDAB/DOPE (dimethyldioctadecylammonium bromide/dioleoylphosphatidyl-ethanolamine) (1:2) cationic liposomes.

Figure 12:
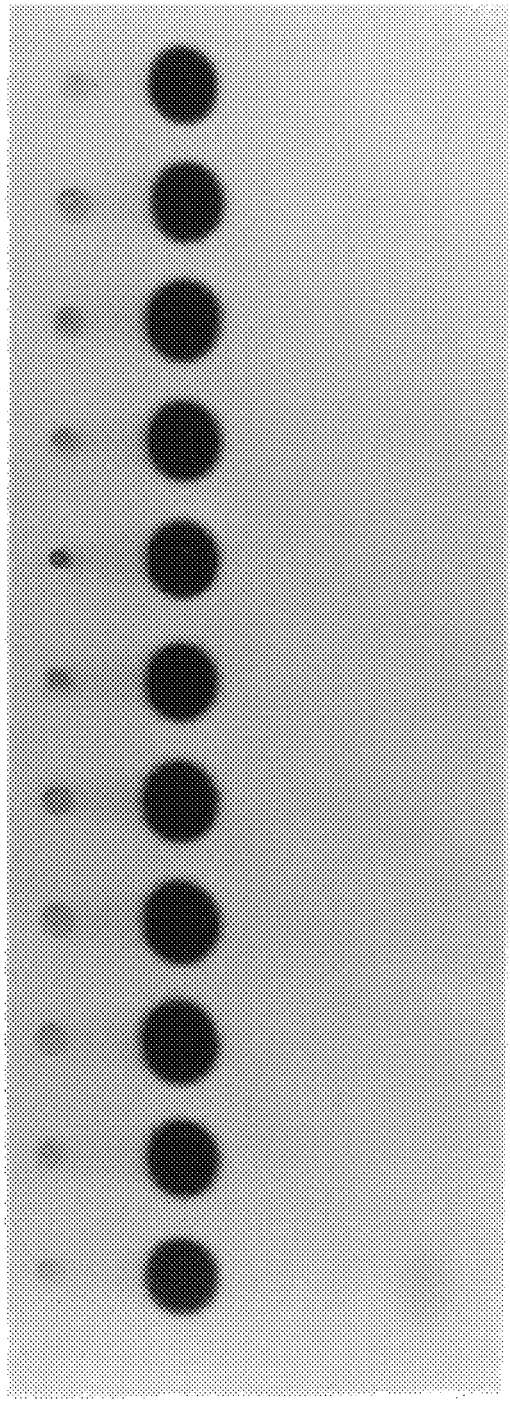
FIG. 12 shows the results of assaying CAT activity in tissue extracts from a nude mouse harboring a human prostate tumor administered a polynucleotide encoding CAT under the transcriptional control of the human PSE. CAT activities from kidney, heart, prostate, liver, pancreas, spleen, brain, lung, bone marrow, bladder and human prostatic tumor mass are shown.

Mice were sacrificed by $CO_2$ suffocation 24 hours later and dissected. Tissues harvested were: kidney, heart, prostate, liver, pancreas, spleen, brain, lung, bone marrow, bladder, and the tumor mass. Tissues were frozen on dry ice and stored at minus 70° C. Tissues (0.025 to 0.25 g) were broken in a ground glass Dounce homogenizer in 500–1000 μl 0.25M Tris pH 7.4, subjected to 3× freeze-thaw, and centrifuged at 14,000 rpm at 4° C. in a microfuge. The supernatant was removed, assayed for protein, and 50 μg protein used for CAT analysis. FIG. 12 shows the results of the CAT assays. The results show CAT activity only in the LNCaP tumors, but no substantial activity in other tissues. The results are consistent with the PSA upstream enhancer being specific to human prostate tissue. The LNCaP line is a human prostate tissue culture cell line producing PSA. The in vitro cell culture results (supra) also demonstrate that the PSA upstream enhancer is specific for human prostate tissue expressing PSA. Mouse prostate tissue may lack the capacity to recognize the human PSA upstream enhancer. It is interesting to note that mouse prostate, and the embryologically related bladder, failed to synthesize CAT under the tested conditions. The in vitro and in vivo results are consistent with the human PSA upstream enhancer being capable of directing gene expression only in human cells expressing PSA. Therefore, the enhancer can be used to ablate PSA-expressing cells with the gene therapy compositions and methods described herein (supra).

Toxin Construct and Introduction into Prostate Cells

A construct was prepared comprising the diphtheria toxin A subunit (DT-A) (540 bp) 5' to the SV40 t antigen, splice site, and poly A signal in BSKSII+. A triple stop translation codon was placed at the 5' end of the DT-A gene. This clone was designated CN47. The HindIII fragment of the PSE (−5824 to +12) was then cloned upstream of the DT-A gene, and designated CN45. Western blots of polyclonal antibody to diphtheria toxin were positive for expression from CN45.

Figure 11:
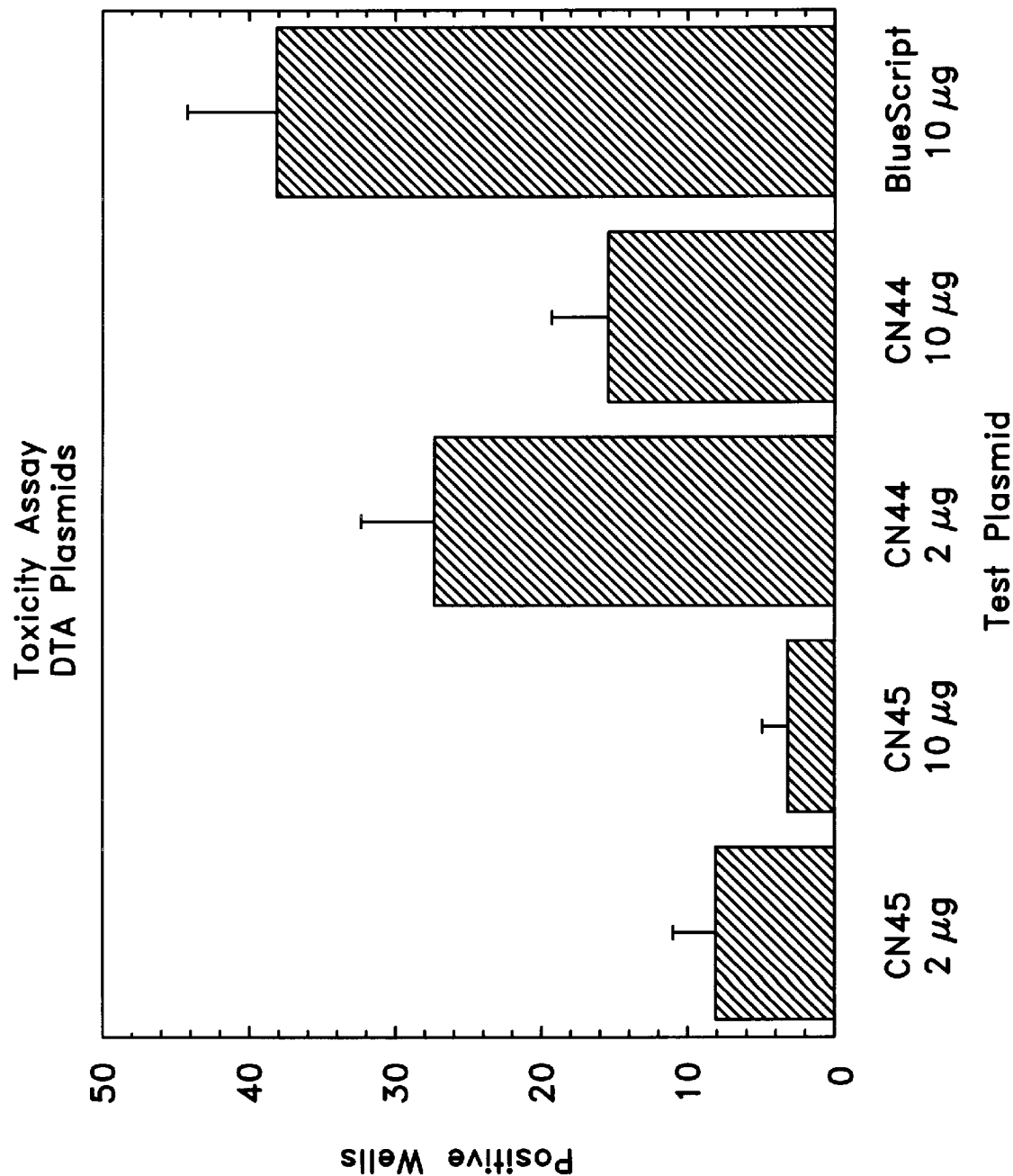
FIG. 11 is a bar diagram showing the in vitro toxicity of the CN45 construct in LNCaP cells. At 15 ug of CN45 DNA in the original transfection 9 colonies grew out. In comparison, BKSKII+ grew out 19 colonies and CN47 grew out 29 colonies. Thus, the presence of a functional diphtheria toxin-A chain in cells co-transfected with a neo expressing plasmid reduced the number of colonies recovered 2–3 fold.

Specifically, the DT-A portion of these constructs were transferred to prokaryotic expression vectors driven by the lac promoter. Following induction with IPTG, preparation of a lysate, gel electrophoresis, and blotting with antibody, CN45 gave a single band of 22,500 MW, the expected size of the DT-A subunit. Both CN45 and CN47 constructs were used to cotransfect LNCaP cells with the plasmid pcDNA3 (Invitrogen) in microtiter plates. pcDNA3 contains the neomycin gene neo, driven by the SV40 early promoter. 48 hours following co-transfection the cells were removed with trypsin and diluted to $10^5$ cells/ml. 100 ul of each cell suspension was added to each well of a 96-well microtiter plate and incubated for 24 h. The media was removed and replaced with fresh media containing G418 (500 ug/ml). Cells were incubated for 4 weeks with biweekly changes of G418 medium. Positive clones were identified with an XXT assay. The results are reported in FIG. 11.

CAT and LUC Constructs Mapping the 5' PSA Region

Figure 5:
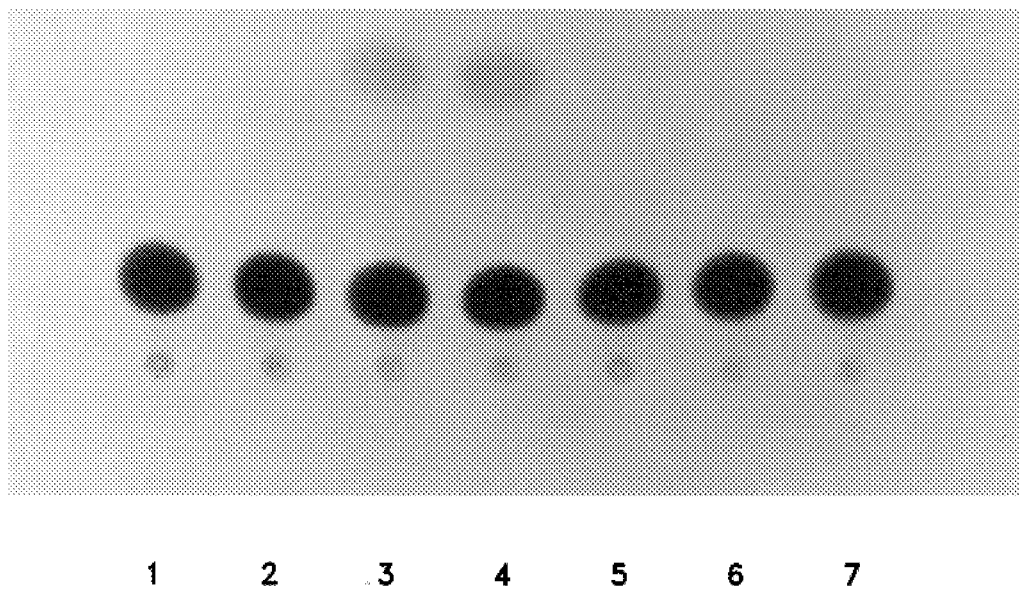
FIG. 5 shows an autoradiogram of the CAT assays of extracts from the prostate cells transfected with the expression constructs shown in FIG. 4.
Figure 6:
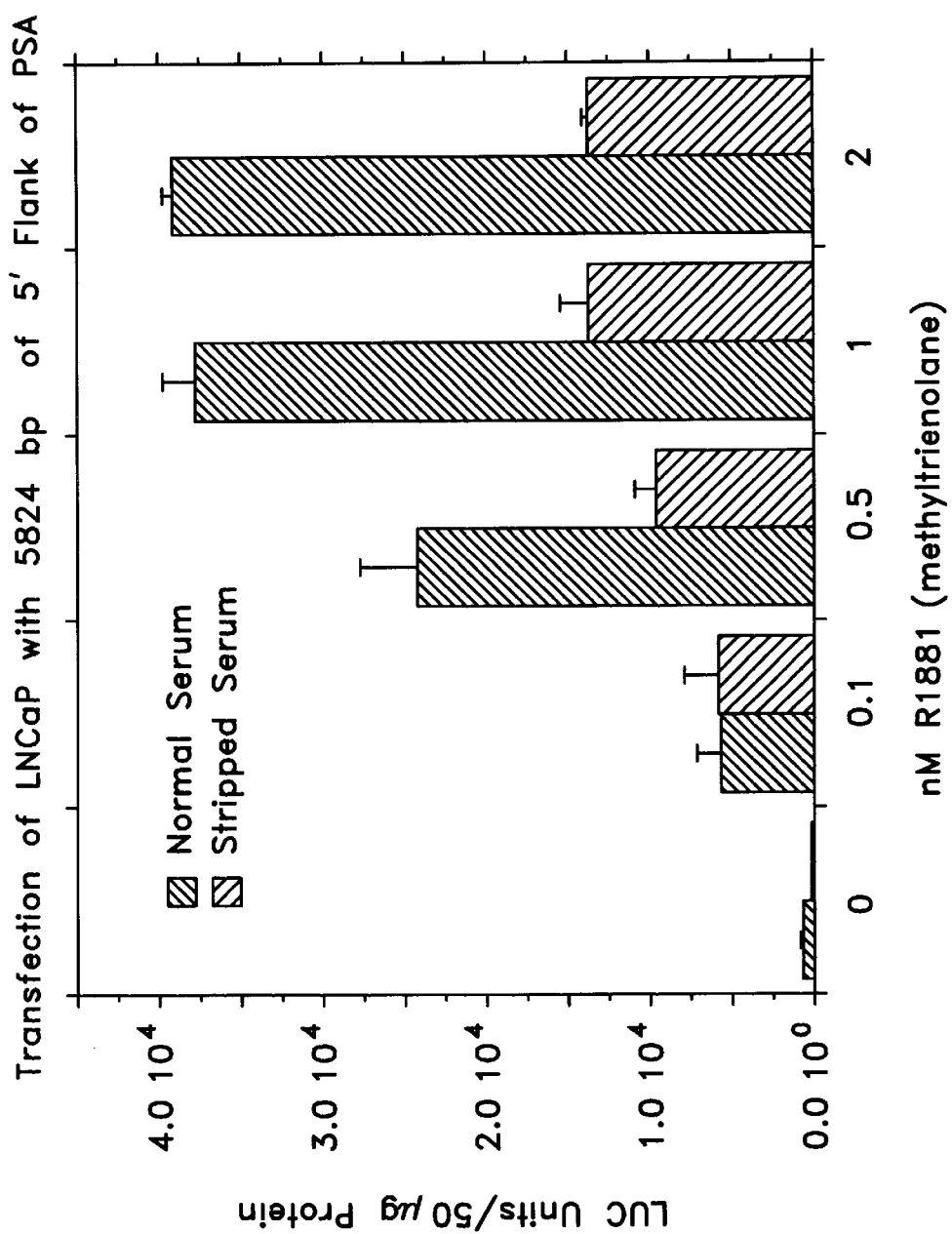
FIG. 6 shows the results of the transfection of LNCaP cells with the entire −5824bp fragment of the 5' flanking region of the PSA gene driving the luciferase gene (LUC) with normal and stripped serum in the presence of increasing amounts of methyltrienolane (R1881).
Figure 7:
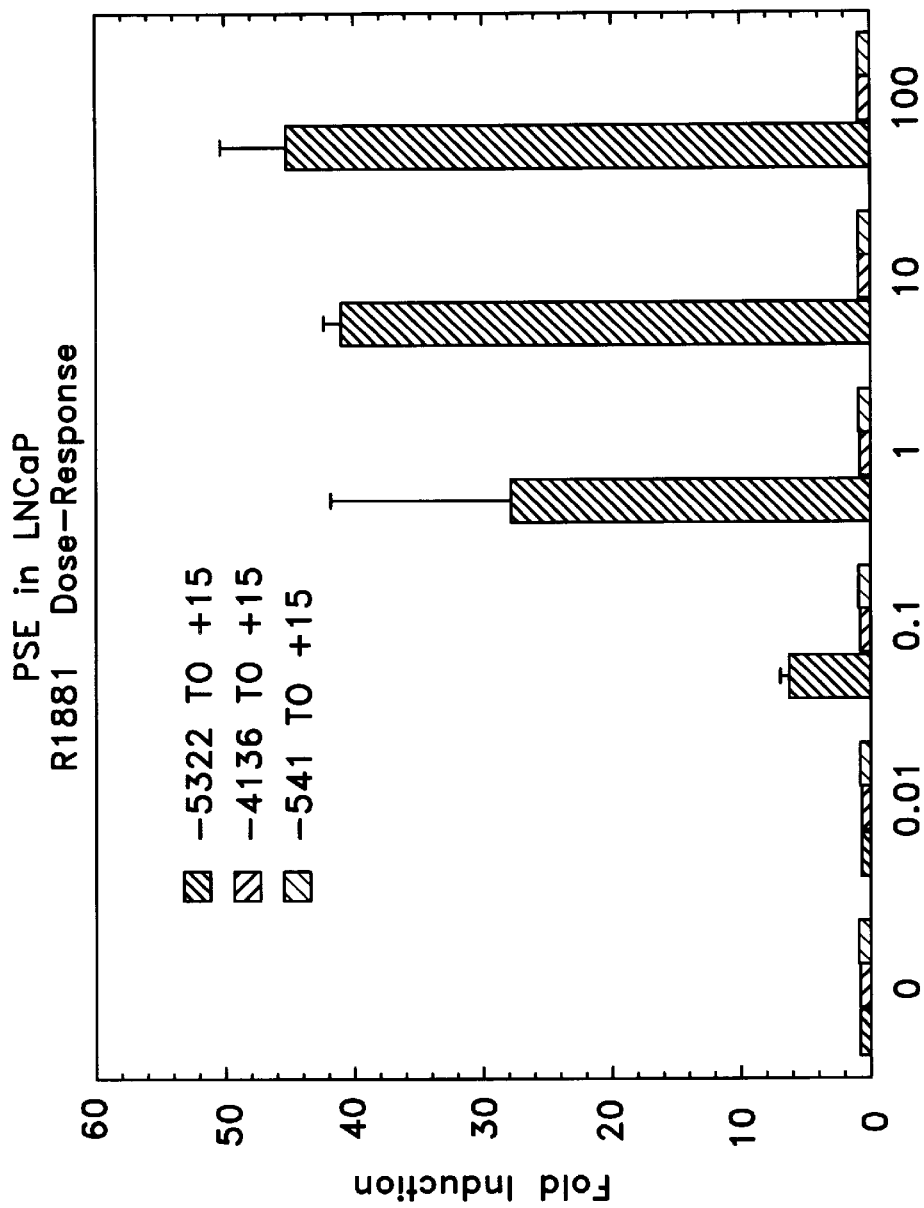
FIG. 7 shows the effect of increasing R1881 concentrations in stripped serum using several constructs of the 5' flanking prostate specific enhancer (PSE) driving CAT.
Figure 8:
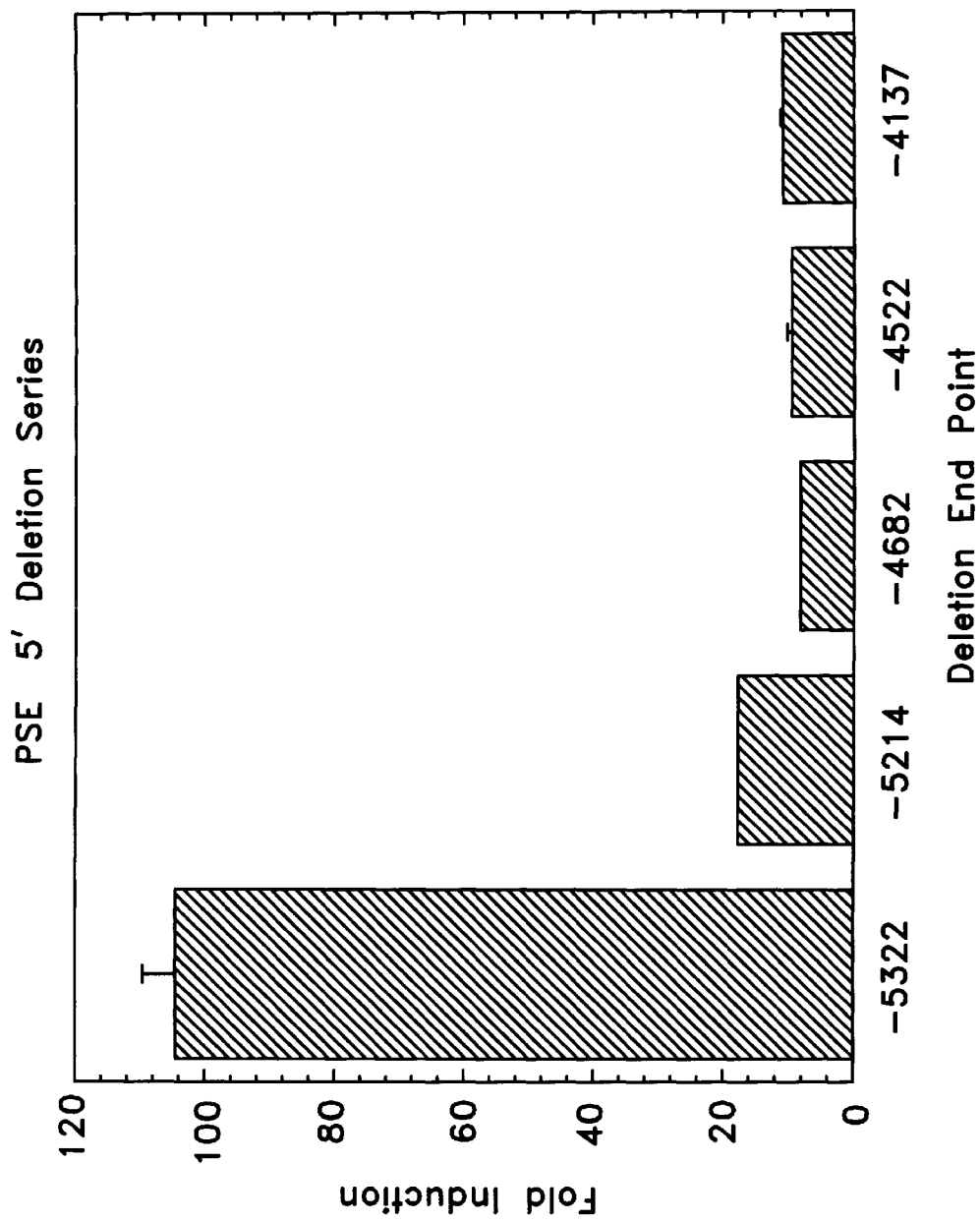
FIG. 8 shows the effect of small deletions designed to define the 5' extent of the required PSE sequence. Constructs were prepared with Exonuclease III in CN42, a construct that contains the XbaI 5' (−5322) to HindIII 3' (+12 ) end driving the CAT gene in a BSKSII backbone, and sequenced. As seen from FIG. 8, even a small deletion 3' from the XbaI site (108 bp) inactivates the PSE.
Figure 9:
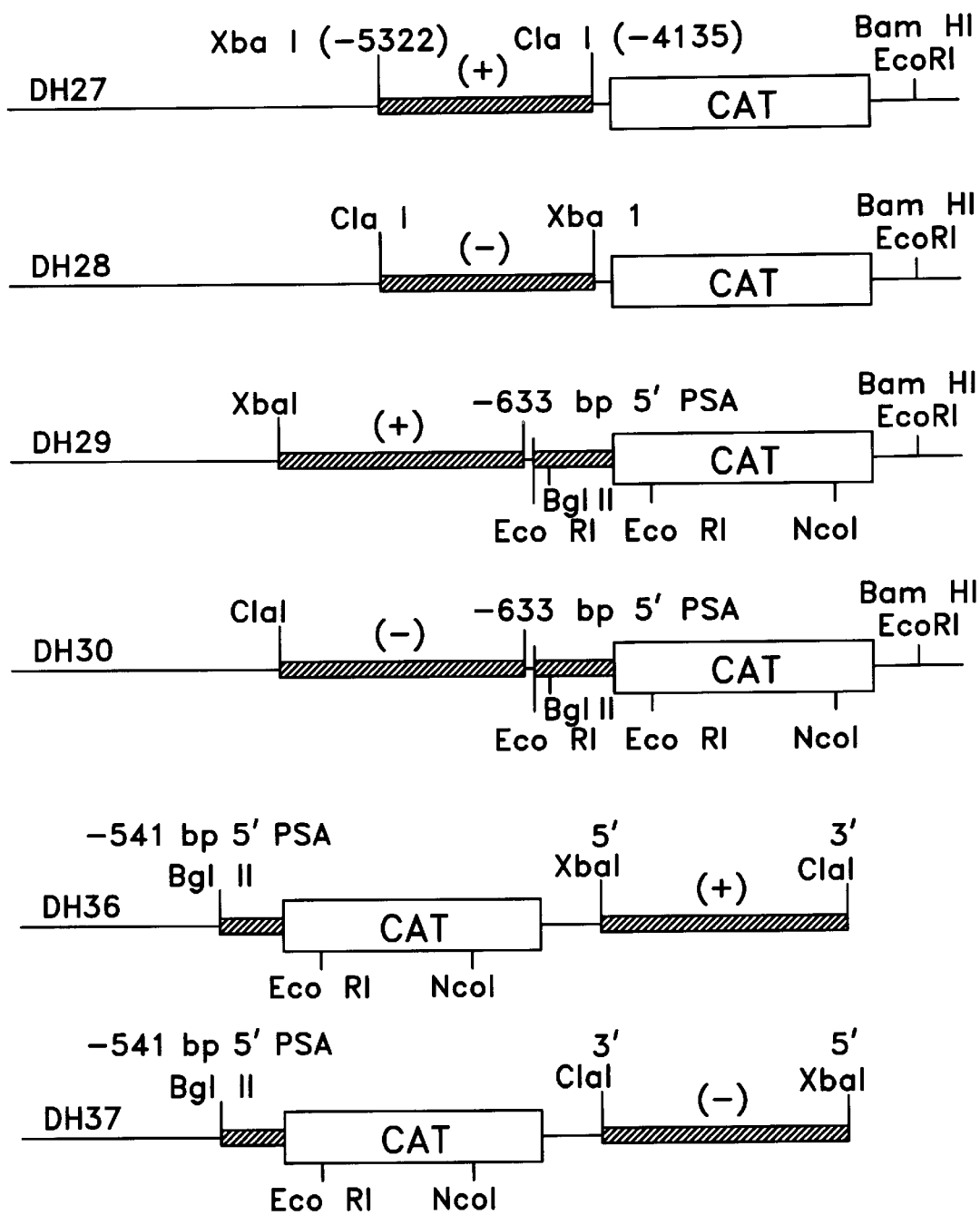
FIG. 9 shows expression constructs where the XbaI-ClaI fragment (SEQ ID NO:02) is moved to various positions in relation to the promoter and coding regions to determine the effect of position of the fragment on its regulatory activity. The 1196bp XbaI-ClaI fragment was moved close to the start site with and without a promoter region in both (+) and (−) orientations, and moved to the 5' end of the CAT gene in both (+) and (−) orientations. None of these constructs showed activity in transfections of LNCaP cells. The conclusion is that the enhancer region within the XbaI (−5322 bp) to ClaI (−4136) is required, but it is not sufficient to function as an enhancer. Rather another sequence between the ClaI (−4136) and the HindIII (+7) is required.
Figure 10:
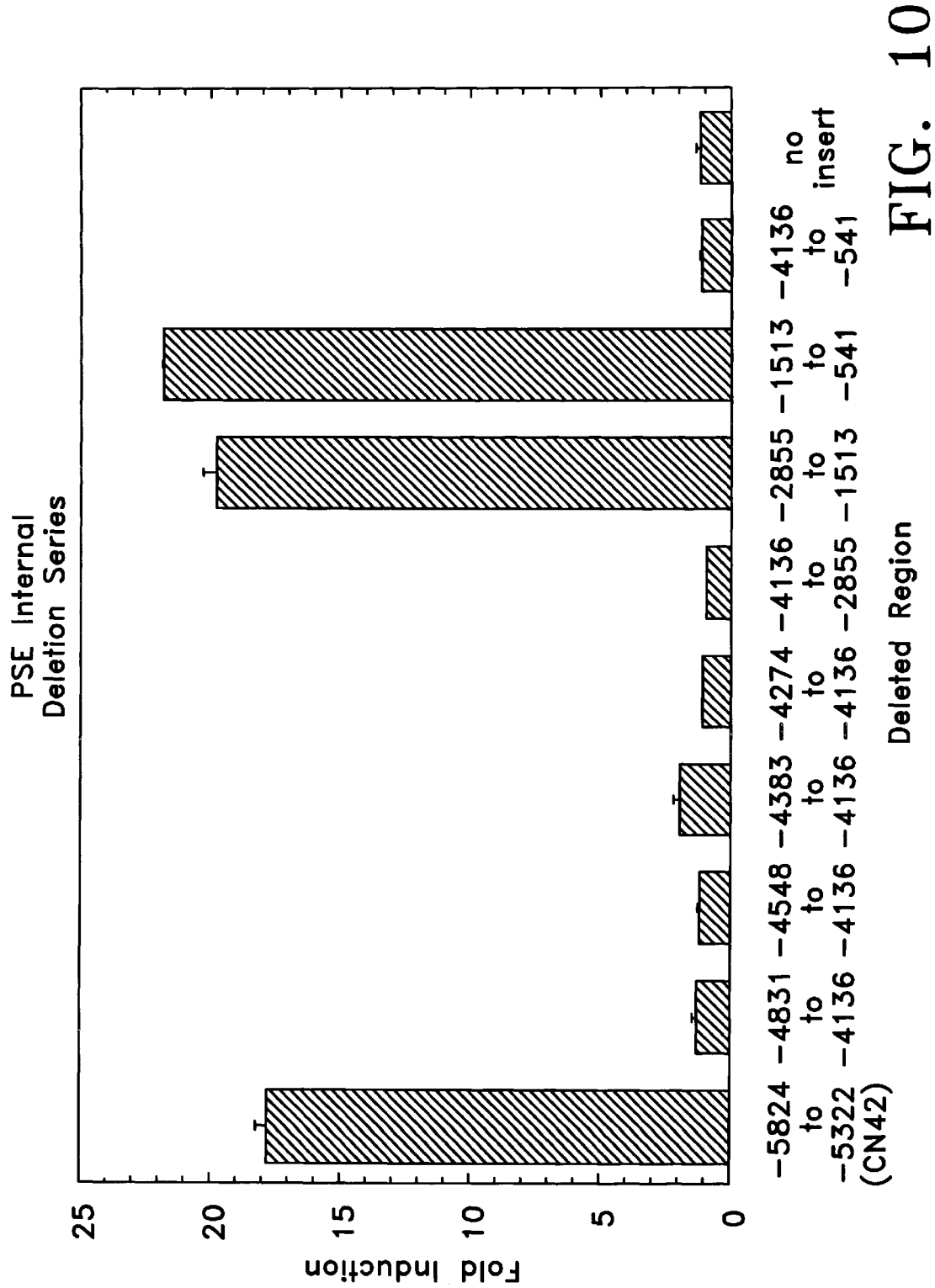
FIG. 10 is a bar diagram of the effect of internal deletions with the PSE driving the CAT gene. The results show that 2310 bp, from the ApaI (−2851) to the BglII (−541) can be deleted. Therefore, the additional sequence required for enhancement is located between the ClaI site and the ApaI site. Thus, the entire PSA enhancer is located between the XbaI (−5322) and the ApaI (−2851), a fragment of 2471 bp. The enhancer functions in concert with a promoter region that extends from the BglII (−541) site to the start of transcription.

CAT and LUC constructs were prepared by standard molecular biology techniques (Sambrook et al., Molecular Cloning: A laboratory manual, Cold Spring Harbor Laboratories, Cold Spring Harbor, N.Y., 1989) in Bluescript KS+ (Stratagene). LNCaP cells were grown in RPMI supplemented with 10% FCS, and antibiotics (100 U penicillin and 100 U streptomycin/ml). 5–7×10⁶ were seeded into 6 cm dishes and grown overnight in RPMI, antibiotics, and 10% stripped serum (Gemini). Cells were washed 2× with 2 ml each PBS and transfected with 25 uM DNA complexed with 50 uM DOTMA:DOPE (1:1) in 1 ml RPMI. DOTMA was synthesized with slight modification of the method of Felgner et al.(Proc. Natl. Acad. Sci. USA 84:7413–7417) and DOPE was from Avanti Polar Lipids (Alabaster, Ala.). Cells were incubated for 3 h, the transfection mix was removed and replaced with RPMI with antibiotics, 10% stripped serum and the indicated concentration of the non-metabolizable synthetic testosterone analog R1881 (New England Nuclear). 48 h post-transfection, the cells were washed twice with PBS and removed with 1 ml of TEN. Cell pellets were redissolved in 100 ul of 0.25M Tris (pH 7.8), subjected to 3× freeze-thaw, and debris removed by centrifugation (10,000 RPM, 5') in an Eppendorf Microfuge. The cell extract was assayed for protein by dye binding (Bio-Rad, Richmond, Calif.). For CAT assays, 50 ug protein was made to 50 ul with 0.25M Tris (pH 7.8) and added to 80 ul of a standard CAT assay mix. After 2 h at 37° C. the mix was extracted with 200 ul of TMPD; mixed xylenes (2:1), vortexed for 20 sec, centrifuged at 10,000 RPM for 5', and 180 ul removed for counting by liquid scintillation. For LUC assays, 50 ug protein was made to 50 ul with 0.25M Tris (pH 7.8) and assayed for LUC activity with a Monolight Luminometer 2010 (Analytical Luminescence Laboratory, San Diego, Calif.). The results are reported in FIGS. 5 to 7.

Polynucleotide Delivery

A polynucleotide construct delivery vehicle can be used for intravenous injection to target lymph node and bone metastases of prostate cancer. In this form, the DNA is condensed and coated with poly-L-lysine to which has been attached a natural ligand for a prostate receptor, such as bFGF. Such structures were found to elicit gene expression preferentially within pancreatic cells. In addition, poly-L-lysine attached to βFGF can be mixed with DNA at levels too low to elicit DNA condensation, and optionally mixed with cationic liposomes at concentrations suitable for DNA condensation and uptake into cells. Such cells can bind specifically to cell surface receptors and deliver the DNA to cells bearing the targeted cell surface receptor.

ANALYSIS OF THE ENHANCER REGION

The following study demonstrates that the enhancer region reported above may be reduced in size, similarly the promoter region, while retaining activity and tissue-specificity. It is noted that there is a limitation as to the truncation with further reductions as the 3' end resulting in degrading of the activity and specificity.

Materials and Methods:

Cells and Culture Methods. LNCaP cells [Horoszewicz et al., Cancer Research (1983) 43:1809–1818] were obtained from the American Type Culture Collection (Rockville, Md.) at passage 9. LNCaP cells were maintained in RPMI medium suplimented with 10% fetal bovine serum (FBS) (Intergen Corp., ), 100 U/ml penicillin, and 100 µg/ml streptomycin. The prostate specific antigen (PSA) production of the cells was tested periodically and was consistently above 20 ng/ml per day. HBL100, MCF-7, Ovcar-3, Panc-1, and DU-145 cells lines were also obtained from the American Type Culture Collection. The 293 cell line was obtained from Microbix, Inc. (Ontartio, Canada). These cells lines were maintainined in Dulbecco's MEM supplemented with 6 gm/l of glucose, as well as FBS and antibiotics as above. Plasmid Constructs. The plasmid CN0 contains the 5.8 kilobase (kb) HinDIII fragment of the human PSA gene covering the region −5834 to +12 relative to the transcription start site cloned into the HinDIII site of pUC18 and was a kind gift of Ake Lundvall [Lundwall and Lilja, FEBS Letters (1987)214:317–322]. pCATbasic and pGL2 promoter vector were purchased from Promega Corp. (Madison, Wis). pCM-Vbeta plasmid was purchased from Clonetech, Inc. (Palo Alto, Calif.). The Bluescript KSII+ (BsKSII+) vector was obtained from Stratagene (La Jolla, Calif.).

DNA manipulations of various plasmids derived in this study were performed by conventional molecular biology techniques. Restriction enzymes and other modifiying enzymes were purchased from various sources including Pharmacia, Bethesda Research Laboratories, and New England biolabs.

CN13 was constructed by inserting the 5.8 kb HinDIII fragment from CN0 in PCAT basic in the correct orientation. CN22 is the 5.8 kb HindIII fragment from CN0 in correct orientation in CN20 (Bluescript KSII+ containing PstI/BamHI of pCAT basic, the CAT gene). CN23 is the 5.3 kb XbaI/HinDIII fragment of CN0 in pCAT basic. CN25 is CN22 cut with ClaI and recircularized; this leaves 4.2 kb 5' PSA fragment driving CAT. CN33 is the BglII/BamHI, (−541 bp to +12 of the PSA gene fused to CAT) from CN22 in BamHI cut BSKSII+; KpnI 5' orientation. CN34 is the BglII/BamHI, (−541 bp to +12 of the PSA gene fused to CAT) from CN22 in BamHI cut BsKSII+ in the opposite orientation to CN33. CN62 is CN13 cut with ClaI and BglII, Klenow end filled, and ligated; the region from −4136 to −541 upstream of the PSA gene is deleted. CN65 was constructed from CN0 PCR amplified with upstream primer 15.59A (5'-TAGGTACCTCTAGAAATCTAGCTGA)(SEQ ID NO:4)) and downstream primer 15.59B (5'-AGCTCGAGCTCGGGATCCTGAG)(SEQ ID NO:5), cut with KpnI and XhoI, ligated into similarly cut CN33; it contains −5322 to −3738 of the PSA upstream region and the promoter from −541 to +12. CN68 was constructed from CN23 cut with ClaI, end-filled with Klenow, and religated. CN69 was constructed from CN23 cut with ClaI, S1 nuclease treated, and religated. CN70 was constructed from CN0 PCR amplified with primers 15.59A and 10.150.2 (5'-AGCTCGAGAAGCAGGCATCCTTG)(SEQ ID NO:6), cut with KpnI and XhoI, ligated into similarly cut CN33 and contains −5322 to −4023 of the PSE and −541 to +12 of the PSA upstream region. CN71 was constructed from CN0 PCR amplified with primers 15.59A and 10.150.1 (5'-AGCTCGAGTTGAGACTGTCCTGC)(SEQ ID NO:7), cut with KpnI and XhoI, ligated into similarly cut CN33. It contains −5322 to −3873 of the PSE and −541 to +12 of the PSA promoter. CN72 was constructed from CN0 PCR amplified with primers 15.59A and 10.164.1 (5'-AGGGTACCTTCGGGATCCTGAG)(SEQ ID NO:8), cut with KpnI, ligated into similarly cut CN33. CN 72 contains −5322 to −3738 upstream of the PSA gene and −541 to +12 of the PSA promoter in the opposite orientation to the wild type enhancer. CN73 was constructed as described for CN72 with the upstream region ligated in the wild type orientation. CN74 and CN75 were constructed as for CN72 and CN73 with the enhancer PCR fragment ligated to KpnI cut CN34; CN75 is in the wild type orientation relative to the promoter and CN74 is in the opposite orientation. To construct a reporter plasmid with the PSA enhancer linked to the SV40 early promoter, CN 20 was cut with HinDIII and XhoI, then ligated to the SV40 early promoter from similarly cut pGL2 to create CN109. CN110 is the KpnI/XhoI fragment of CN65 ligated to similarly cut CN109 placing the PSA enhancer upstream of the SV40 early promoter in the correct orientation.

DNA Sequencing. The 5836 bp HinDIII 5' (−5824 to +12) flanking fragment of the PSA gene was sequenced by the dideoxy chain termination method using Sequenase T4 DNA polymerase (United States Biochemical, Clevland, Ohio). Sequence numbering is according to Lundwall [Biochem. Biophys. Res. Commun. (1989) 161(3):1151–1159]. A series of 3' to 5' nested deletions were made in the plasmid CN0 using exonuclease III timed digestions and were sequenced using the M13 reverse primer. Gaps between sequence data obtained from the exonuclease deletion clones were sequenced using custom sequencing primers synthesized on a Pharmacia Gene Assembler DNA synthesizer. DNA sequence data were assembled using AssemblyLign software (IBI). Both strands of the PSA fragment were sequenced. The sequence has been deposited in Genbank under accession number U37672.

Selected constructs generated by PCR were sequenced to ensure sequence fidelity. The constructs were sequenced on one strand as described above. The constructs which were sequenced were: CN65, CN70 through CN75, CN109, and CN110.

Transfections and Reporter assays. For transfection, LNCaP cells were plated at $5 \times 10^5$ cells per 6 cm culture dish in complete medium. DNAs were introduced into the cells by complexing with DOTMA:DOPE (1:1, Lipofectin, BRL). Briefly, 8 μgm (24.2 nmol) of DNA was diluted into 200 μl of RPMI medium and added to a separate tube containing 50 μmol of Lipofectin in 200 μl of RPMI with gentle mixing. DNA/lipid complexes were allowed to form for 15 minutes at room temperature prior to their dropwise addition to plates of LNCaP cells containing 1 ml of complete medium. The cells were incubated with the complexes overnight at 37° C., 5% $CO_2$. The medium containing the complexes was replaced with RPMI 1640 medium containing 10% charcoal/dextran treated FBS (stripped serum) and supplimented with $10^{-9}$ M methyltrienolone (R1881, NEN DuPont), followed by incubating for a further 48 hours at 37° C. before harvest.

For CAT assays, the cells were harvested by removing the medium, washing the cells once with PBS, and incubating in 1 ml of TEN buffer (50 mM tris pH 7.5, 150 mM NaCl, 1 mM EDTA) for 5 minutes. Cells were scraped off the dishes and extracts made by pelleting the cells, resuspending the cell pellet in 100 μl of 0.25M tris pH7.8, then subjecting the cell suspension to three freeze-thaw cycles. Cell debris was pelleted and the supernatant transfered to fresh tubes and stored at −80° C. Protein concentration of extracts was measured using the BioRad protein dye binding assay.

Quantitative CAT assays were performed as previously described [Kingston and Sheen, in Current Protocols in Molecular Biology, Ausubel et al., eds., 1994, John Wiley & Sons: N.Y. pp9.6.6–9.6.7]. Briefly, cell extracts were normalized for protein content, followed by diluting equal quantities of protein to 90 μl with 0.25M tris pH7.8. Ten microliters of a 10× CAT substrate mix ( 20 mCi/ml $^3$H-chloramphenicol (NEN DuPont), $0.63 \times 10^{-6}$ M chloramphenicol, $2.5 \times 10^{-1}$ M butyryl coenzyme A in water) was added to each sample and vortexed briefly. Samples were incubated at 37° C. for 2 hours followed by a single extraction with 100 μl of a 1:1 mixture of xylenes and tetramethyl pentadecane. The organic phase was transferred to scintillation vials containing Biosafe NA scintillation fluid (Research Products International) and counted. A standard curve was constructed by assaying purified CAT enzyme. Assays for b-galactosidase were performed on cell lysates as previously described [Hidaka and Simonovitch, Mol. Cell. Biol. (1982) 2:1628–1632].

Electrophoretic mobility shift assays (EMSA). Nuclear extracts containing DNA binding proteins were prepared from LNCaP cells by a modification of the method of Dignam et al. [Dignam, et al., Nucleic Acids Res. (1983) 11:1475–1489]. The crude extract was dialyzed against binding buffer (20 mM HEPES pH7.9, 20% glycerol, 100 mM KCl, 0.2 mM EDTA, 0.2 mM phenylmethylsulfonyl fluoride) and stored at −80° C.

DNA probes for EMSA were constructed by synthesizing a series of 16 overlapping polymerase chain reaction (PCR) products spanning −5443 to −3738 relative to the start of PSA gene transcription. The locations of the segments defined by the PCR primer pairs are diagrammed in the results section; primer sequences are omitted here but will be provided upon request. PCR samples were composed of 1 unit of Taq DNA polymerase (Stratagene, La Jolla, Calif.), 1 ng of CN0, PCR buffer supplied by the manufacturer, 200 μM nucleotides, and 50 pmol of each primer. Following an initial denaturing step at 94° C. for 2 minutes, for each of 25 cycles the template was denatured for 45 seconds at 94° C. followed by primer annealing at 50° C. for 90 seconds, then extension of the annealed primers at 72° C. for 60 seconds. Amplification was completed with a final extension step at 72° C. for 5 minutes.

Labeled DNA segments, as defined by the primer pair, were made by modifiying the above PCR protocol. A mixture of 5 pmol of each primer was labeled with $^{32}$P using T4 polynucleotide kinase in a 10 μl reaction volume, and reacted at 37° C. for 1 hour. The kinase reaction mix was then added to 90 μl of PCR mixture containing sufficient template, nucleotides, buffer, and polymerase for a 100 μl reaction. The samples were then cycled as described above. Following amplification, the samples were electrophoresed through a 5% acrylamide/0.5× TBE gel at 150 V. Labeled PCR product was detected by autoradiography. A gel slice containing the labeled DNA was excised, minced, and resuspended in T.E. overnight at 37° C. to elute the DNA. Labeled DNA in the supernatant was removed, an aliquot counted, then diluted to 3,500 cpm/μl.

EMSA procedures were as described [Schuur et al., Cell Growth & Differentiation (1993) 4:761–768]. Binding reactions were assembled with 0.5 µl (approximately 1.5–3.0 µg of protein) of extract, 3 µg of poly dI.dC (1 mg/ml in water, Pharmacia), 10,000 cpm of probe in 3 µl of water, 5 µl (approximately 20–100 ng DNA) unlabeled PCR product as a competitor, and binding buffer to 20 µl. Binding reactions were incubated on ice for 15 minutes, then electrophoresed through a 4% acrylamide, 0.25× TBE gel at 150 V at 4° C. The gels were dried and exposed to Kodak Xomat AR film at −80° C. for 14–40 hours.

Results:

Androgen responsiveness of the PSA gene 5' flanking region. In determining the contribution of regions upstream of the PSA coding region to androgen responsiveness, the 5322 bp XbaI/HinDIII fragment residing at the 5' end of the PSA gene was used to drive the synthesis of reporter genes in PSA-secreting LNCaP cells. This upstream segment of the PSA gene, as well as truncations at −4136 (ClaI) and −541 (BglII) were cloned upstream of the CAT gene to create plasmids CN23, CN25, and CN33. CN23 was highly inducible by the synthetic testosterone analog R1881. Peak level of induction at 100 nM R1881 was 45 fold over the background value of 500 cpm. In contrast, neither CN25 (−4136 to +12) or CN33 (−541 to +12) were inducible at all with R1881. The loss of inducibility with truncation beyond the XbaI site at −5322 reveals the presence of an upstream transcriptional regulatory region whose 5' border is located between the ClaI site at −4136 and the XbaI site at −5322. Typically the levels of induction of CAT synthesis by the extended 5' region in CN23 range from 12 to greater than 50 fold (see below and data not shown) in LNCaP cells. This compares to 1 to 4 fold inducibility of the 5' promoter proximal region of the PSA gene in CN33 which was previously reported to be inactive in LNCaP cells [Riegman, et al., Molecular Endocrinology (1991) 91:1921–1930].

Figure 2:
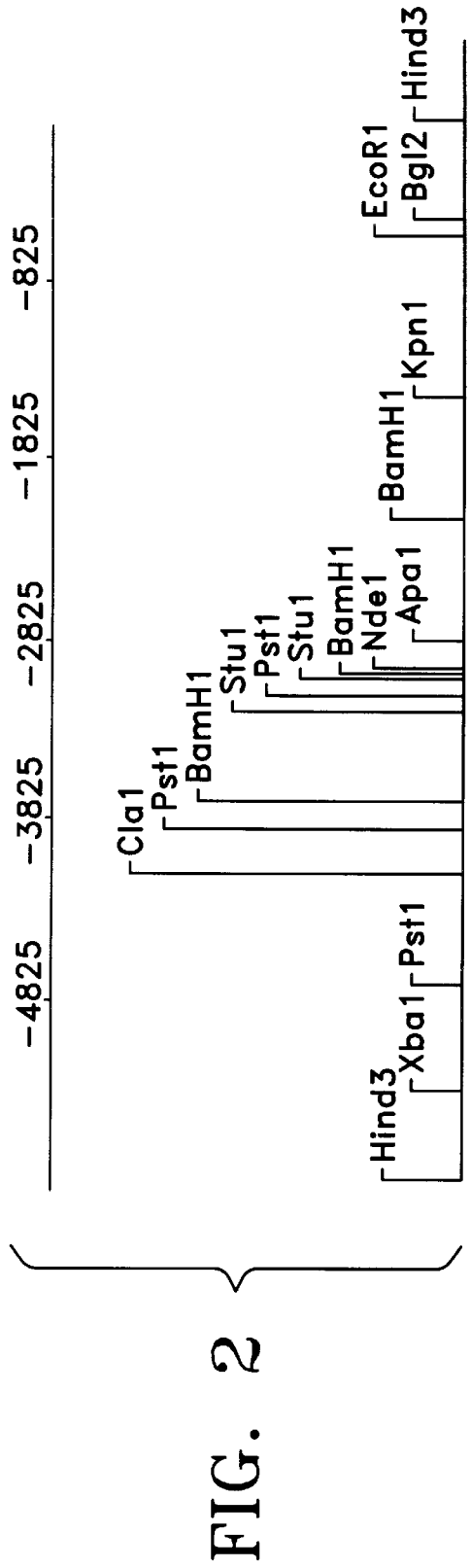
FIG. 2 is a restriction map of the PSA enhancer, extending from the 5' HindIII site to the 3' HindIII site.
Figure 3:
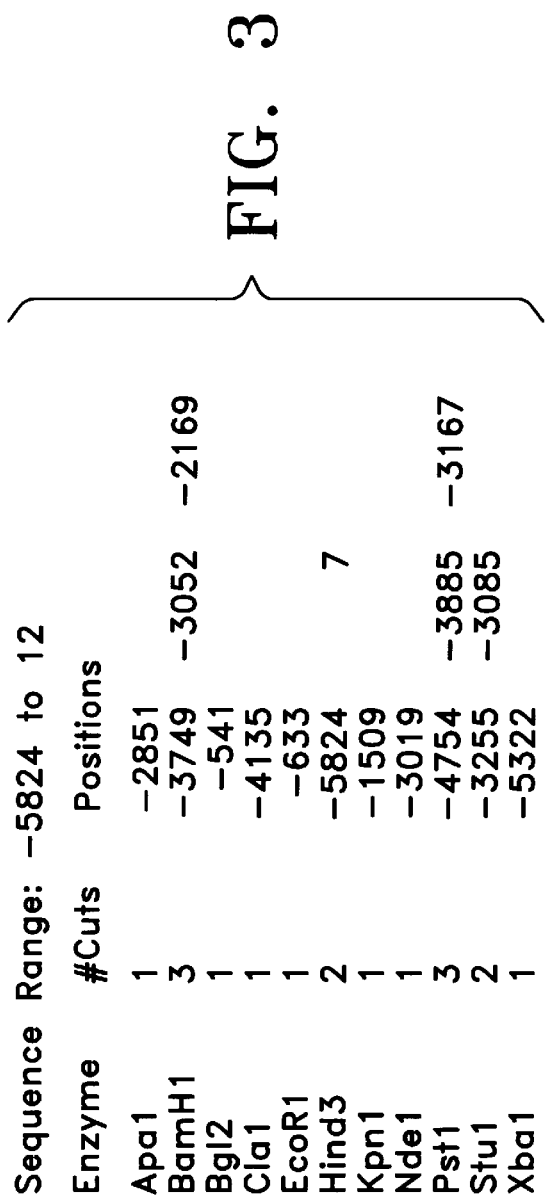
FIG. 3 gives the numerical base positions for the cleavage sites for the indicated restriction enzymes.

Sequence of the 6 kb HinDIII fragment. These results suggest that an enhancer type element resides within this HinDIII fragment somewhere upstream of the ClaI site at −4136 so the sequence of this fragment was determined by the dideoxy chain termination method on both strands. The sequence extends for 5824 bp between the two HinDIII fragment as shown in FIG. 1. Upon inspection, notable features of the sequence are the homonucleotide stretches found in several locations. The largest is a poly purine tract of 57 bases found between −5177 and −5121. In addition, poly T regions are found near −1900 (23 bases) and −1400 (18 bases), and poly A,T regions are found near −1000 (27 bases) and −1100 (26 bases). Computer analysis of the sequence found a number of matches to consensus binding sites for various transcription factors. In particular the sequence between −4148 and −4134 in the minus strand matches the consensus androgen response element (ARE) at 13 of 15 positions [Beato, Cell (1989) 56:335–344; Roche et al., Molecular Endocrinology (1992) 6(12)2229–2235] Glucocorticoid response half sites were also identified at −4726 in the plus strand and −4079 in the minus strand. Additional factor binding sites identified included a 7/7 match to the AP-1 site at −4420, a 7/7 match to the c-Fos serum response element at −4734, and and a 7/7 match to the CREB consensus at −3196. A restriction map showing the relevant restriction sites in the 5.8 kb HinDIII fragment is shown in FIG. 2.

Characterization of the PSA gene enhancer. The 5' border of this potential upstream element was determined by deleting the CN23 construct from the XbaI site using exonuclease III. Transfection of LNCaP cells with CN23 resulted in a 110 fold induction in CAT synthesis. Deletion of 108 bp (CN51) resulted in stimulation of CAT synthesis to 20% of the level induced by CN23. Further deletions toward the 3' end resulted in activity approximately 10% of that stimulated by CN23. These data map the 5' end of this upstream element to within 108 bp of the XbaI site.

The 3' border of the upstream element was mapped by constructing reporter plasmids containing upstream sequences starting at the XbaI site and extending to variable distances downstream of the ClaI site which were cloned upstream of the PSA gene promoter through the BglII site. An induction of 27 fold was observed for CN23 while CN33 was not inducible. Removal of the sequences between −3738 and −541 (CN65) resulted in a 38 fold induction. When the deletion was extended further upstream to −3872 (CN71) the level of induction was approximately double that seen with CN65. Additional deletion to −4022 in CN70 resulted in induction of 32 fold, while removal of the sequences between the ClaI site and the BglII site in CN62 abolished activity of the upstream element. The combination of these results indicate that the 3' border of the upstream enhancer element lies between the ClaI site at −4136 and the endpoint of CN65 at −3738. In addition, these results suggest that the region between −4022 and −3738 is not necessary for enhancer activity but contains elements that influence the level of transcription.

One of the defining features of enhancer elements is their ability to function in stimulating transcription despite their location or orientation relative to the promoter upon which they act [Tijan and Maniatis, Cell (1994) 77:5–8]. To determine if the element defined above has these properties the segment of the upstream region from the XbaI site to −3738 was inserted upstream of the PSA promoter/CAT gene transcription unit in both orientations; the same gene segment was also inserted downstream of the CAT gene in both orientations. CN73 is essentially the same as CN65 and yielded a 44 fold induction in LNCaP cells treated with R1881. The same segment in the opposite orientation resulted in a 36 fold induction (CN72). This level of induction remained unchanged when the upstream element was moved downstream of the CAT gene with an orientation opposite that in CN73 (CN74). Reversal of this orientation downstream of the CAT gene in CN75 also resulted in high level of induction of 25 fold. These levels of induction compared to a 1 fold induction using the promoter construct CN33. These results confirm that the element characterized above possesses the properties of an enhancer.

Despite the presence of ARE sequences within the upstream enhancer it is conceivable that the androgen regulation of PSA expression is contributed by the ARE at −170. To determine if the PSA enhancer contributes to androgen responsiveness, the PSA enhancer was placed upstream of the SV40 early promoter (CN110). Cultures of LNCaP cells transfected with CN110, CN109 (containing the SV40 early promoter alone), CN65 (containing the PSA promoter plus enhancer), or CN33 (containing the PSA promoter alone) were treated with increasing concentrations of R1881, then assayed for CAT activity. Activity of CN110 ranged from 76 fold induction over background in the absence of R1881 to 206 fold induction at $10^{31.8}$ M R1881 while activity of CN65 ranged from 37 to 137 fold at these same R1881 concentrations. CN109 stimulated approximately 16 fold induction of transcription at all R1881 concentrations while CN33 activity did not exceed 2 fold activation. CN110 and CN65 displayed similar patterns of response to increasing R1881 concentrations with peak levels of transcriptional stimulation observed at $10^{-8}$ M R1881. These data show both that the PSA enhancer is androgen responsive and that it's acitivity is independent of the promoter used.

To determine if the potential ARE at −4148 functions in androgen inducibility of the upstream element, alterations were made within the ClaI site in CN23 to construct CN68 and CN69. The plasmid CN23 was cut with ClaI, then either endfilled with Klenow (CN68) or treated with S1 nuclease (CN69), then religated. The former treatment resulted in addition of a CG dinucleotide 3' to −4136, while the latter treatment removed bases −4137 to −4134. The wild type sequence in CN23 yielded a 27 fold induction in LNCaP cells, while addition of two bases within the ClaI site resulted in half the level of induction. Interestingly, removal of the 5 bases within the ClaI site resulted in a three fold increase in the level of CAT synthesis relative to the wild type sequence. The bases removed reside in the right most portion of the potential ARE. These results suggest that this ARE may be functional and that it's activity may be influenced by neighboring sequences. These sequences may bind transcription factors which might be required for formation of prostate-specific DNA-protein complexes and for prostate-specific PSA expression (see below).

Tissue specificity of the PSA gene enhancer. The PSA protein is recognized to be the most useful biomarker of malignant disease. Very little, or no, PSA protein is synthesized by tissues outside of the prostate. It was therefore important to determine if the enhancer described above retained not only androgen responsiveness, but also the high level of tissue specificity characteristic of the PSA gene.

To this end, a variety of cell lines were transfected with three reporter constructs: CN13 containing the 5836 bp 5' region, CN65 containing the minimal enhancer/promoter, and CN33 containing the promoter alone. The cell lines used represent several hormone responsive tissues including human breast epithelia (HBL100), human breast carcinoma (MCF-7), pancreatic cancer (PANC-1), ovarian carcinoma (OVCAR-3), and prostate carcinoma (LNCaP, DU145). The 293 cell line was derived from human embryonic kidney cells transformed by adenovirus DNA. The cell lines were transfected as described in materials and methods with reporter DNAs admixed with an internal control plasmid, pCMVbeta.

In LNCaP cells both CN13 and CN65 stimulate CAT synthesis approximately 9 fold above background, while CN33 stimulated a 2 fold accumulation of CAT. In no other cell line did CN13 or CN65 lead to more than a 2 fold induction of CAT synthesis. The highest levels of activity outside of LNCaP cells were observed in Panc-1 and Ovcar-3, where CN13 reached approximately 1.5 fold and 2.5 fold, respectively; CN65 exhibited less than two fold induction in both of these cell lines. Not surprisingly, all three PSA reporter constructs were inactive in the DU145 prostatic carcinoma cell line since the PSA gene is inactive [Papsidero et al., J. Of the Natl. Cancer Inst. (1981) 66(1):37–42]. In contrast to the enhancer-containing reporters, the CN33 construct stimulated CAT synthesis to approximately two fold in each of the cell lines tested except Panc-1 where a 4 fold induction was observed. In each case CN33 was more active than the enhancer containing constructs.

Preliminary results using LNCaP tumor xenografts in the nude mouse model support the retention of tissue specificity in vivo. When CN23 complexed with a lipid delivery vehicle (e.g. DOTMA/DOPE, 1:1) was introduced into LNCaP tumors as well as other mouse tissues either by direct injection or systemically, CAT activity was only detected in tumor. These results also indicate that the PSA enhancer/promoter combination has retained tissue specific properties to a large degree both in vitro and in vivo.

Figure 13:
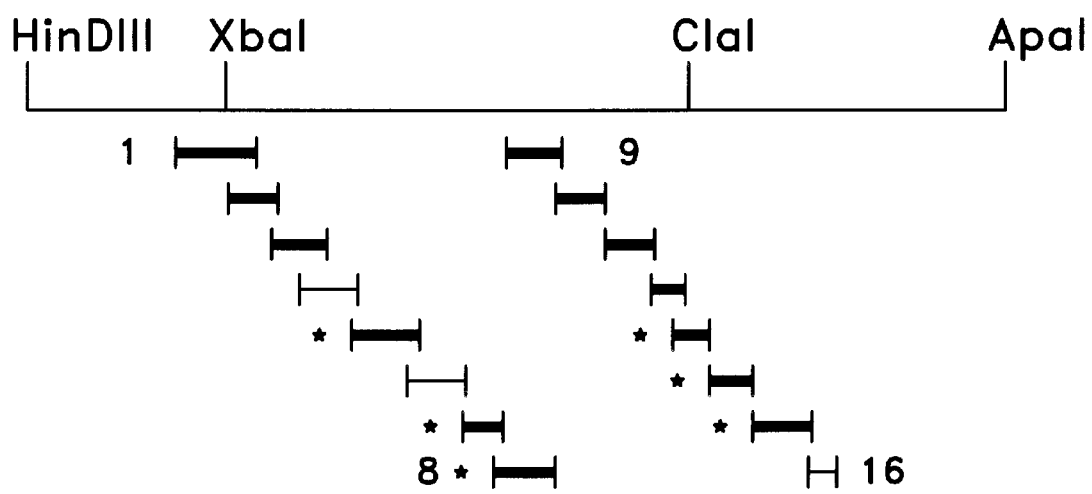
FIG. 13 shows a summary of the EMSA analysis of the PSE. A restriction map spanning the enhancer region is diagrammed at the top; the portions of the enhancer covered by each probe are depicted by brackets below the map are numbered sequentially. Bold brackets indicate probes which formed complexes with either LNCaP or MCF-7 extracts; probes which formed complexes only with LNCaP extracts are indicated by an asterisk; probes which did not form specific DNA protein complexes are indicated by thin brackets. (See Schuur et al., (1996) J. Biol. Chem. 271:7043–7051, which is incorporated herein specifically by reference.).

DNA-protein complexes on the PSA gene enhancer. The above data demonstrate that an enhancer resides upstream of the PSA gene promoter. Furthermore, it supports the conclusion that this enhancer is responsible, at least in part, for the narrow tissue distribution of PSA expression. Protein-DNA complexes which form on this enhancer are likely to control this tissue-specific expression. In characterizing these protein-DNA complexes, segments of the enhancer were assessed for their ability to form such complexes by EMSA. Sixteen subsegments of the enhancer were created by PCR with end labeled primers for use as probes in LNCaP cell and MCF-7 cell extracts by EMSA. The locations of these subsegments and a summary of the the results of this survey are presented in FIG. 13.

Figure 14:
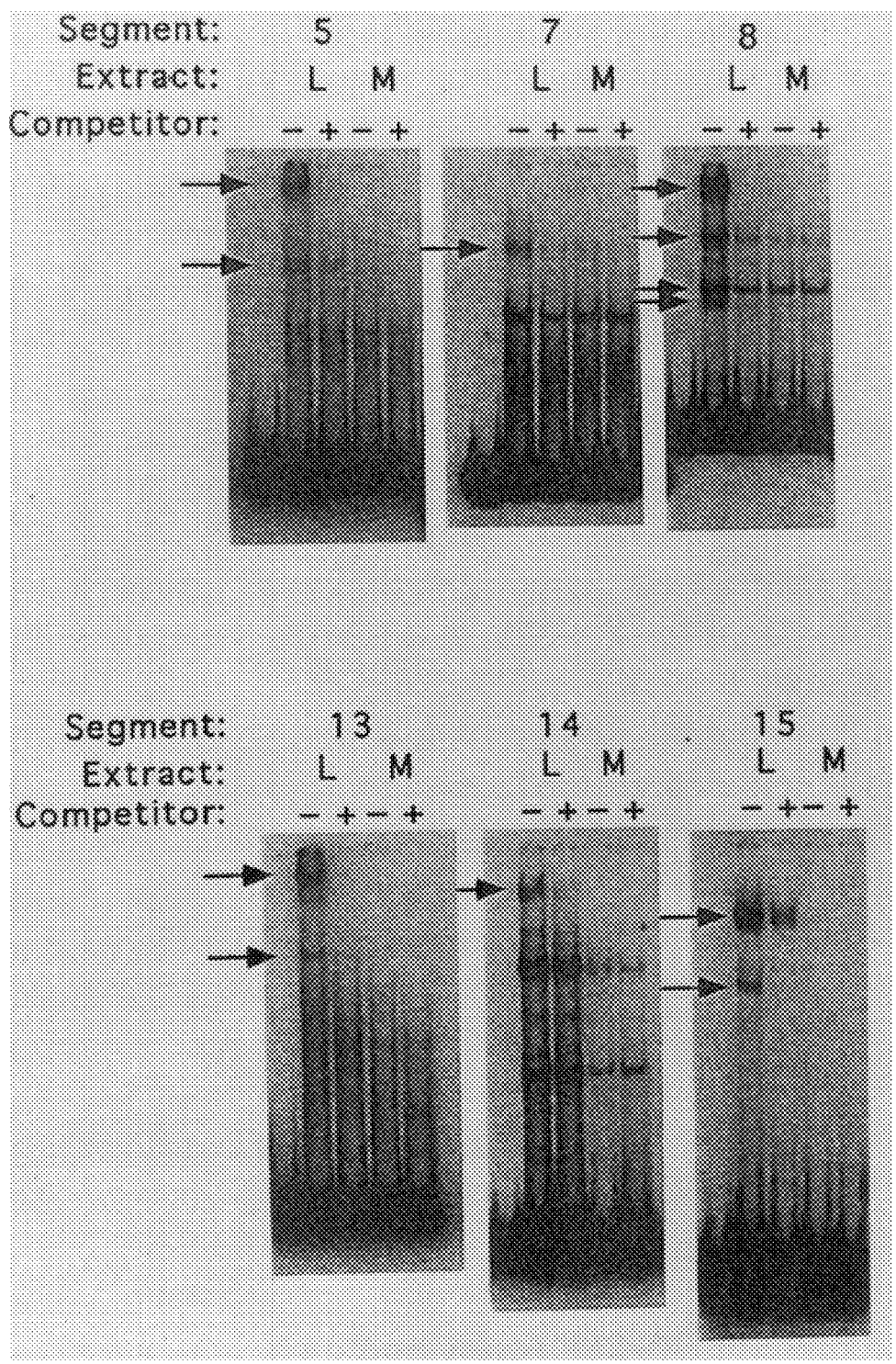
FIG. 14 shows autoradiographs of PCR-amplified segments which bound proteins only in LNCaP extracts.

The PCR-amplified segments which bound proteins only in LNCaP extracts span −4980 to −4797 (segment 5), −4710 to −4479 (segments 7 and 8), and −4168 to −3801 (segments 13 through 15). Autoradiographs of EMSA with these probes are shown in FIG. 14. In each example multiple complexes are formed with the probes; often the faster-migrating complexes are formed with both cell extracts and appear to be non-specific. Complexes specific to LNCaP extracts are indicated by an arrow in lane two of each panel (LNCaP extract+mock competitor). The absence or reduction of these complexes in lanes 3 (LNCaP extract+specific competitor) demonstrated the specific nature of these complexes. Four specific complexes were formed with segment 8, while three specific complexes were formed with probe 13. Two each were formed with probes 5, 13 and 15. One complex each was formed with probes 7 and 14. The relatively large size of the probes and the slow migration of the complexes observed suggests a higher order arrangement of multiple proteins on the DNA segments.

The segments are numbered starting with the 5' most region and range in size from 87 bp (#16) to 184 bp (#5). The ability of the DNA segments to form protein-DNA complexes was scored by two criteria: specific complex formation as judged by competition with unlabeled homologous PCR product and the formation of the complexes by one or both of the cell extracts. Each of the segments formed specific complexes (indicated by a bold bracket) except for segments 4 and 6. Of the segments which formed complexes, six (segments 5, 7, 8, 13, 14, and 15) formed specific complexes only with LNCaP extracts (indicated by *). Two findings are apparent from this analysis: 1) protein-DNA complexes are formed at various locations across the entire enhancer, and 2) complexes specific to LNCaP extracts are formed at several locations on the enhancer.

Effect of truncation of the PSE and PSA promoter on activity and specificity

The PSE and PSA promoter were truncated to varying degrees to determine the effect of removal of 5' and 3' sequences on the activity and specificity of the transcriptional initiation region derived from the transcriptional initiation region of human PSA.

Plasmid Constructs—The plasmid CN0 contains the 5.8 kilobase (kb) HinDIII fragment of the human PSA gene covering the region −5834 to +12 relative to the transcriptional start site cloned into the HinD III site of PUC 18 and was a kind gift of Ake Lundwall [FEBS Letters, 1987 214(2): 317–322]. pCATbasic and the pGL2 promoter were purchased from Promega Corporation. pCMVBeta plasmid was purchased from Clontech Incorporated. (Palo Alto, Calif.). The Bluescript KSII+(BsKSII+) was obtained from Stratagene.

DNA manipulation of various plasmids derived in this study were performed by conventional molecular biology techniques. Restriction enzymes were purchased from various sources including Pharmacia Biotech Incorporated, Life Technologies Incorporated, and New England Biolabs.

CN20 is the PstI/BamHI fragment of pcatbasic in similarly cut BSKSII+. CN22 is the 5.8 kb HinDIII fragment from CN0 in correct orientation in CN20. CN33 is the BglII/BamHI (−541 to +12 of the PSA gene fused to CAT) from CN22 in BamHI cut BSKSII+; KpnI 5' orientation. CN65 was constructed from CN0 PCR amplified with primer 15.59A (5'-TAGGTACCTCTAGAAATCTAGCTGA) (SEQ ID NO:9) and downstream primer 15.59B (5'-AGCTCGAGCTTCGGGATCC-TGAG) (SEQ ID NO:10), cut with KpnI and XhoI, and ligated into similarly cut CN33; It contains −5322 to −3740 of the PSA upstream region and the PSA promoter from −541 to +12. CN102 was constructed from CN0 PCR amplified with upstream primer 18.90.3 (5'-GGACCTCGAGATCTTTTTATGATGAC(SEQ ID NO:11)) and downstream primer 18.69.1 (5'-GCGCAAGCTTGGGCTGGG(SEQ ID NO:12)), cut with XhoI and HinDIII, and ligated into similarly cut CN65; It contains −5322 to −3740 of the PSA upstream region fused directly to the PSA promoter from −541 to +12.

CN103 was constructed from CN0 PCR amplified with upstream primer 18.119 (5'-GGACCTCGAGGTCTCCATGAGCTAC)(SEQ ID NO:13) and downstream primer 18.69.1 (5'-GCGCAAGCTTGGGCTGGG)(SEQ ID NO:14), cut with XhoI and HinDIII, and ligated into similarly cut CN65; It contains −5322 to −3740 of the PSA upstream region fused directly to the PSA promoter from −221 to +12.

CN104 was constructed in several steps. CN70 was constructed from CN0 PCR amplified with upstream primer 15.59A (5'-TAGGTACCTCTAGAAATCTAGCTGA)(SEQ ID NO:15) and downstream primer 10.150.2 (5'AGCTCGAGAAGCAGGCATCCTTG) (SEQ ID NO:16), cut with KpnI and XhoI, and ligated into similarly cut CN33; It contains −5322 to −4023 of the PSA upstream region and the promoter from −541 to +12. CN 104 was constructed from CN0 PCR amplified with upstream primer 18.119 (5'-GGACCTCGAGGTCTCC-ATGAGCTAC) (SEQ ID NO:17) and downstream primer 18.69.1 (5'-GCGCAAGCTTGG-GCTGGG) (SEQ ID NO:18), cut with XhoI and HinDIII, and ligated into similarly cut CN70; It contains from −5322 to −4023 of the PSA upstream region fused directly to the PSA promoter from −221 to +12.

CN105 was constructed in several steps. CN71 was constructed from CN0 PCR amplified with upstream primer 15.59A (5'-TAGGTACCTCTAGAAATCT-AGCTGA) (SEQ ID NO:19) and downstream primer 10.150.1 (5'-AGCTCGAGTTGAGACTG-TCCTGC) (SEQ ID NO:20), cut with KpnI and XhoI, and ligated into similarly cut CN33; It contains from −5322 to −3874 of the PSA upstream region and from −541 to +12 of the PSA promoter. CN105 was constructed from CN0 PCR amplified with upstream primer 15.59A (5'-TAGGTACCTCTAGAAATCTAGCTGA) (SEQ ID NO:21) and downstream primer 10.150.1 (5'-AGCTCGAGTTGAGACTGTCCTGC(SEQ ID NO:22), cut with XhoI and HinDIII, and ligated into similarly cut CN71; It contains from −5322 to −3874 of the PSA upstream region fused directly to the PSA promoter from −221 to +12.

Transfections and Reporter assays—For transfection, cells were plated at $5 \times 10^5$ cells per 6 cm culture dish in complete medium. DNAs were introduced into the cells by complexing with DOTMA:DOPE (1:1, Lipofectin, BRL). Briefly, 8 μgm (24.2 nmol) of DNA was diluted into 200 μl of RPMI medium and added to a separate tube containing 50 μmol of Lipofectin in 200 μl of RPMI with gentle mixing. DNA/lipid complexes were allowed to form for 15 minutes at room temperature prior to their dropwise addition to plates of cells containing 1 ml of complete medium. The cells were incubated with the complexes overnight at 37° C., 5% $CO_2$. The medium containing the complexes was replaced with RPMI 1640 medium containing 10% charcoal/dextran treated FBS (stripped serum) and supplemented with $10^{-9}$ M methyltrienolone (R1881, NEN DuPont), followed by incubating for a further 48 hours at 37° C. before harvest.

For CAT assays, the cells were harvested by removing the medium, washing the cells once with PBS, and incubating in 1 ml of TEN buffer (50 mM tris pH 7.5, 150 mM NaCl, 1 mM EDTA) for 5 minutes. Cells were scraped off the dishes and extracts made by pelleting the cells, resuspending the cell pellet in 100 μl of 0.25M tris pH7.8, then subjecting the cell suspension to three freeze-thaw cycles. Cell debris was pelleted and the supernatant transfered to fresh tubes and stored at −80° C. Protein concentration of extracts was measured using the Bradford assay.

Quantitative CAT assays were performed as previously described [Kingston and Sheen, *A Simple Phase Extraction Assay for CAT Activity*, in *Current Protocols in Molecular Biiology*, F. M. Ausubel et al, Editors, 1995, John Wiley & Sons: New York. P. 9.6.6–9.6.7]. Briefly, cell extracts were normalized for protein content, followed by diluting equal quantities of protein to 90 μl with 0.25M tris pH7.8. Ten microliters of a 10× CAT substrate mix ( 20 mci/ml $^3$H-chloramphenicol (NEN DuPont), $0.63 \times 10^6$ M chloramphenicol, $2.5 \times 10^{-1}$ M butyryl coenzyme A in water) was added to each sample and vortexed briefly. Samples were incubated at 37° C. for 2 hours followed by a single extraction with 100 μl of a 1:1 mixture of xylenes and tetramethyl pentadecane. The organic phase was transfered to scintillation vials containing Biosafe NA scintillation fluid (Research Products International) and counted. A standard curve was constructed by assaying purified CAT enzyme. The results are reported in FIG. 15 All publications and patent applications cited in this specification are herein incorporated by reference as if each individual publication or patent application were specifically and individually indicated to be incorporated by reference.

Although the present invention has been described in some detail by way of illustration for purposes of clarity of understanding, it will be apparent that certain changes and modifications may be practiced within the scope of the claims.

What is claimed is:

1. An isolated polynucleotide comprising a prostate-specific enhancer (PSE) operably linked to a polynucleotide sequence encoding a heterologous polypeptide, wherein said PSE comprises a sequence within SEQ ID NO 1, wherein the PSE activates transcription of an operably linked nucleotide sequence in a cell of a human prostate.

2. The polynucleotide according to claim 1, wherein said PSE is about 2.5 kb.

3. The polynucleotide according to claim 2, wherein said PSE comprises bases about 525 to about 3025 of SEQ ID NO 1.

4. The polynucleotide according to claim 1, wherein said PSE comprises bases about 503 to about 2973 of SEQ ID NO 1.

5. The polynucleotide according to claim 2, wherein said PSE is about 50 to 250 bases.

6. The polynucleotide according to claim 1 wherein said PSE comprises bases about 841 to about 1024 of SEQ ID NO 1.

7. The polynucleotide according to claim 1 wherein said PSE comprises bases about 1111 to about 1342 of SEQ ID NO 1.

8. The polynucleotide according to claim 1 wherein said PSE comprises bases about 1653 to about 2020 of SEQ ID NO 1.

9. An isolated polynucleotide comprising a prostate-specific enhancer (PSE), wherein said PSE comprises a sequence within SEQ ID NO 1, and wherein said isolated polynucleotide is less than about 6 kb, and wherein the PSE activates transcription of an operably linked nucleotide sequence in a prostate cell.

10. The polynucleotide according to claim 9, wherein said PSE is about 2.5 kb.

11. The polynucleotide according to claim 10, wherein said PSE comprises bases about 525 to about 3025 of SEQ ID NO 1.

12. The polynucleotide according to claim 10, wherein said PSE comprises bases about 503 to about 2973 of SEQ ID NO 1.

13. The polynucleotide according to claim 9, wherein said PSE is about 50 to 250 bases.

14. The polynucleotide according to claim 9 wherein said PSE comprises bases about 841 to about 1024 of SEQ ID NO 1.

15. The polynucleotide according to claim 9 wherein said PSE comprises bases about 1111 to about 1342 of SEQ ID NO 1.

16. The polynucleotide according to claim 9 wherein said PSE comprises bases about 1653 to about 2020 of SEQ ID NO 1.

17. A vector comprising the polynucleotide of claim 9.
18. The vector of claim 17, which is a transcription vector.
19. The vector of claim 17, which is an expression vector.

20. A composition for expressing an anti-proliferation construct in a cell of human prostate, said cell expressing prostate-specific antigen (PSA), said composition comprising:

a sterile physiologically acceptable carrier;

a prostate-specific enhancer (PSE), wherein said PSE comprises a sequence in SEQ ID NO 1; and a DNA sequence encoding an anti-proliferation molecule, wherein said PSE is operably linked to said DNA sequence, and wherein said anti-proliferation molecule comprises an anti-proliferation sequence selected from the group consisting of a toxin gene, an antigen gene, a lymphokine gene, a viral gene, and an antisense sequence.

21. The polynucleotide according to claim 9, wherein polynucleotide is less than about 5.5 kb.

22. An isolated polynucleotide comprising a prostate-specific enhancer (PSE) and a heterologous promoter, wherein the PSE comprises a sequence within SEQ ID NO: 1, and wherein the enhancer activates transcription of an operably linked nucleotide sequence in a cell of a human prostate.

23. The polynucleotide according to claim 22, wherein said PSE is about 2.5 kb.

24. The polynucleotide according to claim 23, wherein said PSE comprises bases about 525 to about 3025 of SEQ ID NO 1.

25. The polynucleotide according to claim 22, wherein said PSE comprises bases about 503 to about 2973 of SEQ ID NO 1.

26. The polynucleotide according to claim 23, wherein said PSE is about 50 to 250 bases.

27. The polynucleotide according to claim 22 wherein said PSE comprises bases about 841 to about 1024 of SEQ ID NO 1.

28. The polynucleotide according to claim 22 wherein said PSE comprises bases about 1111 to about 1342 of SEQ ID NO 1.

29. The polynucleotide according to claim 22 wherein said PSE comprises bases about 1653 to about 2020 of SEQ ID NO 1.

30. A viral vector for transfection of human cells comprising a polynucleotide according to any of claims 1 to 8.

31. A method for expressing a structural gene in a cell of a human prostate, said cell expressing a prostate specific antigen (PSA), said method comprising:

introducing a construct comprising said structural gene operably linked to a polynucleotide according to claim 9 into the prostate cells; and expressing said structural gene.

32. A method according to claim 30 wherein said polynucleotide comprises a PSE encompassed within about 525 and 3025 of SEQ ID NO 1.

33. The composition according to claim 20 wherein said DNA sequence is in a lipofection complex or liposome.

34. The composition according to claim 20 wherein said DNA sequence is part of a viral vector.

* * * * *

UNITED STATES PATENT AND TRADEMARK OFFICE

CERTIFICATE OF CORRECTION

PATENT NO. : 6,057,299

DATED : May 2, 2000

INVENTOR(S) : Daniel R. HENDERSON

It is certified that error appears in the above-identified patent and that said Letters Patent is hereby corrected as shown below:

In column 50, claim 31, line 15, after "said cell expressing", please delete [a]; and
In column 50, claim 32, line 21, please replace "30" with --31--.

Signed and Sealed this

Tenth Day of April, 2001

Attest:

NICHOLAS P. GODICI

Attesting Officer       Acting Director of the United States Patent and Trademark Office

SEQUENCE LISTING (1) GENERAL INFORMATION:

(iii) NUMBER OF SEQUENCES: 22

(2) INFORMATION FOR SEQ ID NO:1:

(i) SEQUENCE CHARACTERISTICS:
    (A) LENGTH: 5836 base pairs
    (B) TYPE: nucleic acid
    (C) STRANDEDNESS: single
    (D) TOPOLOGY: linear (xi) SEQUENCE DESCRIPTION: SEQ ID NO:1:

```
AAGCTTCTAG TTTTCTTTTC CCGGTGACAT CGTGGAAAGC ACTAGCATCT CTAAGCAATG      60

ATCTGTGACA ATATTCACAG TGTAATGCCA TCCAGGGAAC TCAACTGAGC CTTGATGTCC     120

AGAGATTTTT GTGTTTTTTT CTGAGACTGA GTCTCGCTCT GTGCCAGGCT GGAGTGCAGT     180

GGTGCAACCT TGGCTCACTG CAAGCTCCGC CTCCTGGGTT CACGCCATTC TCCTGCCTCA     240

GCCTCCTGAG TAGCTGGGAC TACAGGCACC CGCCACCACG CCTGGCTAAT TTTTTTGTAT     300

TTTTAGTAGA GATGGGGTTT CACTGTGTTA GCCAGGATGG TCTCAGTCTC CTGACCTCGT     360

GATCTGCCCA CCTTGGCCTC CCAAAGTGCT GGGATGACAG GCGTGAGCCA CCGCGCCTGG     420

CCGATATCCA GAGATTTTTT GGGGGGCTCC ATCACACAGA CATGTTGACT GTCTTCATGG     480

TTGACTTTTA GTATCCAGCC CCTCTAGAAA TCTAGCTGAT ATAGTGTGGC TCAAAACCTT     540

CAGCACAAAT CACACCGTTA GACTATCTGG TGTGGCCCAA ACCTTCAGGT GAACAAAGGG     600

ACTCTAATCT GGCAGGATAT TCCAAAGCAT TAGAGATGAC CTCTTGCAAA GAAAAAGAAA     660

TGGAAAAGAA AAAGAAAGAA AGGAAAAAAA AAAAAAAAA GAGATGACCT CTCAGGCTCT      720

GAGGGGAAAC GCCTGAGGTC TTTGAGCAAG GTCAGTCCTC TGTTCACAG TCTCCCTCAC      780

AGGGTCATTG TGACGATCAA ATGTGGTCAC GTGTATGAGG CACCAGCACA TGCCTGGCTC     840

TGGGGAGTGC CGTGTAAGTG TATGCTTGCA CTGCTGAATG CTTGGGATGT GTCAGGGATT     900

ATCTTCAGCA CTTACAGATG CTCATCTCAT CCTCACAGCA TCACTATGGG ATGGGTATTA     960

CTGGCCTCAT TTGATGGAGA AAGTGGCTGT GGCTCAGAAA GGGGGGACCA CTAGACCAGG    1020

GACACTCTGG ATGCTGGGA CTCCAGAGAC CATGACCACT CACCAACTGC AGAGAAATTA    1080

ATTGTGGCCT GATGTCCCTG TCCTGGAGAG GGTGGAGGTG GACCTTCACT AACCTCCTAC    1140

CTTGACCCTC TCTTTTAGGG CTCTTTCTGA CCTCCACCAT GGTACTAGGA CCCCATTGTA    1200

TTCTGTACCC TCTTGACTCT ATGACCCCCA CTGCCCACTG CATCCAGCTG GGTCCCCTCC    1260

TATCTCTATT CCCAGCTGGC CAGTGCAGTC TCAGTGCCCA CCTGTTTGTC AGTAACTCTG    1320

AAGGGGCTGA CATTTTACTG ACTTGCAAAC AAATAAGCTA ACTTTCCAGA GTTTTGTGAA    1380

TGCTGGCAGA GTCCATGAGA CTCCTGAGTC AGAGGCAAAG GCTTTTACTG CTCACAGCTT    1440

AGCAGACAGC ATGAGGTTCA TGTTCACATT AGTACACCTT GCCCCCCCCA AATCTTGTAG    1500

GGTGACCAGA GCAGTCTAGG TGGATGCTGT GCAGAAGGGG TTTGTGCCAC TGGTGAGAAA    1560

CCTGAGATTA GGAATCCTCA ATCTTATACT GGGACAACTT GCAAACCTGC TCAGCCTTTG    1620

TCTCTGATGA AGATATTATC TTCATGATCT TGGATTGAAA ACAGACCTAC TCTGGAGGAA    1680

CATATTGTAT CGATTGTCCT TGACAGTAAA CAAATCTGTT GTAAGAGACA TTATCTTTAT    1740

TATCTAGGAC AGTAAGCAAG CCTGGATCTG AGAGAGATAT CATCTTGCAA GGATGCCTGC    1800

TTTACAAACA TCCTTGAAAC AACAATCCAG AAAAAAAAG GTGTTGCTGT CTTTGCTCAG     1860

AAGACACACA GATACGTGAC AGAACCATGG AGAATTGCCT CCCAACGCTG TTCAGCCAGA    1920

GCCTTCCACC CTTGTCTGCA GGACAGTCTC AACGTTCCAC CATTAAATAC TTCTTCTATC    1980

ACATCCTGCT TCTTTATGCC TAACCAAGGT TCTAGGTCCC GATCGACTGT GTCTGGCAGC    2040

ACTCCACTGC CAAACCCAGA ATAAGGCAGC GCTCAGGATC CCGAAGGGGC ATGGCTGGGG    2100
```

```
ATCAGAACTT CTGGGTTTGA GTGAGGAGTG GGTCCACCCT CTTGAATTTC AAAGGAGGAA    2160

GAGGCTGGAT GTGAAGGTAC TGGGGGAGGG AAAGTGTCAG TTCCGAACTC TTAGGTCAAT    2220

GAGGGAGGAG ACTGGTAAGG TCCCAGCTCC CGAGGTACTG ATGTGGGAAT GGCCTAAGAA    2280

TCTCATATCC TCAGGAAGAA GGTGCTGGAA TCCTGAGGGG TAGAGTTCTG GGTATATTTG    2340

TGGCTTAAGG CTCTTTGGCC CCTGAAGGCA GAGGCTGGAA CCATTAGGTC CAGGGTTTGG    2400

GGTGATAGTA ATGGGATCTC TTGATTCCTC AAGAGTCTGA GGATCGAGGG TTGCCCATTC    2460

TTCCATCTTG CCACCTAATC CTTACTCCAC TTGAGGGTAT CACCAGCCCT TCTAGCTCCA    2520

TGAAGGTCCC CTGGGCAAGC ACAATCTGAG CATGAAAGAT GCCCCAGAGG CCTTGGGTGT    2580

CATCCACTCA TCATCCAGCA TCACACTCTG AGGGTGTGGC CAGCACCATG ACGTCATGTT    2640

GCTGTGACTA TCCCTGCAGC GTGCCTCTCC AGCCACCTGC AACCGTAGA GCTGCCCATC     2700

CTCCTCTGGT GGGAGTGGCC TGCATGGTGC CAGGCTGAGG CCTAGTGTCA GACAGGGAGC    2760

CTGGAATCAT AGGGATCCAG GACTCAAAAG TGCTAGAGAA TGGCCATATG TCACCATCCA    2820

TGAAATCTCA AGGGCTTCTG GGTGGAGGGC ACAGGGACCT GAACTTATGG TTTCCCAAGT    2880

CTATTGCTCT CCCAAGTGAG TCTCCCAGAT ACGAGGCACT GTGCCAGCAT CAGCCTTATC    2940

TCCACCACAT CTTGTAAAAG GACTACCCAG GGCCCTGATG AACACCATGG TGTGTACAGG    3000

AGTAGGGGGT GGAGGCACGG ACTCCTGTGA GGTCACAGCC AAGGGAGCAT CATCATGGGT    3060

GGGGAGGAGG CAATGGACAG GCTTGAGAAC GGGGATGTGG TTGTATTTGG TTTTCTTTGG    3120

TTAGATAAAG TGCTGGGTAT AGGATTGAGA GTGGAGTATG AAGACCAGTT AGGATGGAGG    3180

ATCAGATTGG AGTTGGGTTA GATAAAGTGC TGGGTATAGG ATTGAGAGTG GAGTATGAAG    3240

ACCAGTTAGG ATGAGGATC AGATTGGAGT TGGGTTAGAG ATGGGTAAA ATTGTGCTCC      3300

GGATGAGTTT GGGATTGACA CTGTGGAGGT GGTTTGGGAT GGCATGGCTT TGGGATGGAA    3360

ATAGATTTGT TTTGATGTTG GCTCAGACAT CCTTGGGGAT TGAACTGGGG ATGAAGCTGG    3420

GTTTGATTTT GGAGGTAGAA GACGTGGAAG TAGCTGTCAG ATTTGACAGT GGCCATGAGT    3480

TTTGTTTGAT GGGGAATCAA ACAATGGGGG AAGACATAAG GGTTGGCTTG TTAGGTTAAG    3540

TTGCGTTGGG TTGATGGGGT CGGGGCTGTG TATAATGCAG TTGGATTGGT TTGTATTAAA    3600

TTGGGTTGGG TCAGGTTTTG GTTGAGGATG AGTTGAGGAT ATGCTTGGGG ACACCGGATC    3660

CATGAGGTTC TCACTGGAGT GGAGACAAAC TTCCTTTCCA GGATGAATCC AGGGAAGCCT    3720

TAATTCACGT GTAGGGGAGG TCAGGCCACT GGCTAAGTAT ATCCTTCCAC TCCAGCTCTA    3780

AGATGGTCTT AAATTGTGAT TATCTATATC CACTTCTGTC TCCCTCACTG TGCTTGGAGT    3840

TTACCTGATC ACTCAACTAG AAACAGGGGA AGATTTTATC AAATTCTTTT TTTTTTTTT    3900

TTTTTTTTGA GACAGAGTCT CACTCTGTTG CCCAGGCTGG AGTGCAGTGG CGCAGTCTCG    3960

GCTCACTGCA ACCTCTGCCT CCCAGGTTCA AGTGATTCTC CTGCCTCAGC CTCCTGAGTT    4020

GCTGGGATTA CAGGCATGCA GCACCATGCC CAGCTAATTT TTGTATTTTT AGTAGAGATG    4080

GGGTTTCACC AATGTTTGCC AGGCTGGCCT CGAACTCCTG ACCTGGTGAT CCACCTGCCT    4140

CAGCCTCCCA AAGTGCTGGG ATTACAGGCG TCAGCCACCG CGCCCAGCCA CTTTTGTCAA    4200

ATTCTTGAGA CACAGCTCGG GCTGGATCAA GTGAGCTACT CTGGTTTTAT TGAACAGCTG    4260

AAATAACCAA CTTTTTGGAA ATTGATGAAA TCTTACGGAG TTAACAGTGG AGGTACCAGG    4320

GCTCTTAAGA GTTCCCGATT CTCTTCTGAG ACTACAAATT GTGATTTTGC ATGCCACCTT    4380

AATCTTTTTT TTTTTTTTTT TAAATCGAGG TTTCAGTCTC ATTCTATTTC CCAGGCTGGA    4440

GTTCAATAGC GTGATCACAG CTCACTGTAG CCTTGAACTC CTGGCCTTAA GAGATTCTCC    4500
```

```
TGCTTCGGTC TCCCAATAGC TAAGACTACA GTAGTCCACC ACCATATCCA GATAATTTTT     4560

AAATTTTTTG GGGGGCCGGG CACAGTGGCT CACGCCTGTA ATCCCAACAC CATGGGAGGC     4620

TGAGATGGGT GGATCACGAG GTCAGGAGTT TGAGACCAGC CTGACCAACA TGGTGAAACT     4680

CTGTCTCTAC TAAAAAAAAA AAAAATAGAA AAATTAGCCG GGCGTGGTGG CACACGGCAC     4740

CTGTAATCCC AGCTACTGAG GAGGCTGAGG CAGGAGAATC ACTTGAACCC AGAAGGCAGA     4800

GGTTGCAATG AGCCGAGATT GCGCCACTGC ACTCCAGCCT GGGTGACAGA GTGAGACTCT     4860

GTCTCAAAAA AAAAAAATTT TTTTTTTTTT TTTGTAGAGA TGGATCTTGC TTTGTTTCTC     4920

TGGTTGGCCT TGAACTCCTG GCTTCAAGTG ATCCTCCTAC CTTGGCCTCG AAAGTGTTG      4980

GGATTACAGG CGTGAGCCAC CATGACTGAC CTGTCGTTAA TCTTGAGGTA CATAAACCTG     5040

GCTCCTAAAG GCTAAAGGCT AAATATTTGT TGGAGAAGGG GCATTGGATT TTGCATGAGG     5100

ATGATTCTGA CCTGGGAGGG CAGGTCAGCA GGCATCTCTG TTGCACAGAT AGAGTGTACA     5160

GGTCTGGAGA ACAAGGAGTG GGGGGTTATT GGAATTCCAC ATTGTTTGCT GCACGTTGGA     5220

TTTTGAAATG CTAGGGAACT TTGGGAGACT CATATTTCTG GGCTAGAGGA TCTGTGGACC     5280

ACAAGATCTT TTTATGATGA CAGTAGCAAT GTATCTGTGG AGCTGGATTC TGGGTTGGGA     5340

GTGCAAGGAA AAGAATGTAC TAAATGCCAA GACATCTATT TCAGGAGCAT GAGGAATAAA     5400

AGTTCTAGTT TCTGGTCTCA GAGTGGTGCA GGGATCAGGG AGTCTCACAA TCTCCTGAGT     5460

GCTGGTGTCT TAGGGCACAC TGGGTCTTGG AGTGCAAAGG ATCTAGGCAC GTGAGGCTTT     5520

GTATGAAGAA TCGGGATCG TACCCACCCC CTGTTTCTGT TTCATCCTGG GCATGTCTCC      5580

TCTGCCTTTG TCCCCTAGAT GAAGTCTCCA TGAGCTACAA GGGCCTGGTG CATCCAGGGT     5640

GATCTAGTAA TTGCAGAACA GCAAGTGCTA GCTCTCCCTC CCCTTCCACA GCTCTGGGTG     5700

TGGGAGGGGG TTGTCCAGCC TCCAGCAGCA TGGGGAGGGC CTTGGTCAGC CTCTGGGTGC     5760

CAGCAGGGCA GGGGCGGAGT CCTGGGGAAT GAAGGTTTTA TAGGGCTCCT GGGGGAGGCT     5820

CCCCAGCCCC AAGCTT                                                    5836

(2) INFORMATION FOR SEQ ID NO:2:

(i) SEQUENCE CHARACTERISTICS:
        (A) LENGTH: 1192 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:2:

TCTAGAAATC TAGCTGATAT AGTGTGGCTC AAAACCTTCA GCACAAATCA CACCGTTAGA      60

CTATCTGGTG TGGCCCAAAC CTTCAGGTGA ACAAAGGGAC TCTAATCTGG CAGGATATTC     120

CAAAGCATTA GAGATGACCT CTTGCAAAGA AAAGAAATG GAAAGAAAA AGAAAGAAAG       180

GAAAAAAAAA AAAAAAAGA GATGACCTCT CAGGCTCTGA GGGGAAACGC CTGAGGTCTT      240

TGAGCAAGGT CAGTCCTCTG TTGCACAGTC TCCCTCACAG GGTCATTGTG ACGATCAAAT     300

GTGGTCACGT GTATGAGGCA CCAGCACATG CCTGGCTCTG GGGAGTGCCG TGTAAGTGTA     360

TGCTTGCACT GCTGAATGCT TGGGATGTGT CAGGGATTAT CTTCAGCACT TACAGATGCT     420

CATCTCATCC TCACAGCATC ACTATGGGAT GGGTATTACT GGCCTCATTT GATGGAGAAA     480

GTGGCTGTGG CTCAGAAAGG GGGGACCACT AGACCAGGGA CACTCTGGAT GCTGGGGACT     540

CCAGAGACCA TGACCACTCA CCAACTGCAG AGAAATTAAT TGTGGCCTGA TGTCCCTGTC     600
```

```
CTGGAGAGGG TGGAGGTGGA CCTTCACTAA CCTCCTACCT TGACCCTCTC TTTTAGGGCT      660

CTTTCTGACC TCCACCATGG TACTAGGACC CCATTGTATT CTGTACCCTC TTGACTCTAT      720

GACCCCCACT GCCCACTGCA TCCAGCTGGG TCCCCTCCTA TCTCTATTCC CAGCTGGCCA      780

GTGCAGTCTC AGTGCCCACC TGTTTGTCAG TAACTCTGAA GGGGCTGACA TTTTACTGAC      840

TTGCAAACAA ATAAGCTAAC TTTCCAGAGT TTTGTGAATG CTGGCAGAGT CCATGAGACT      900

CCTGAGTCAG AGGCAAAGGC TTTTACTGCT CACAGCTTAG CAGACAGCAT GAGGTTCATG      960

TTCACATTAG TACACCTTGC CCCCCCCAAA TCTTGTAGGG TGACCAGAGC AGTCTAGGTG     1020

GATGCTGTGC AGAAGGGGTT TGTGCCACTG GTGAGAAACC TGAGATTAGG AATCCTCAAT     1080

CTTATACTGG GACAACTTGC AAACCTGCTC AGCCTTTGTC TCTGATGAAG ATATTATCTT     1140

CATGATCTTG GATTGAAAAC AGACCTACTC TGGAGGAACA TATTGTATCG AT            1192
```

(2) INFORMATION FOR SEQ ID NO:3:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:3:

```
GGTACANNNT GTTCCT                                                      16
```

(2) INFORMATION FOR SEQ ID NO:4:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:4:

```
TAGGTACCTC TAGAAATCTA GCTGA                                            25
```

(2) INFORMATION FOR SEQ ID NO:5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:5:

```
AGCTCGAGCT CGGGATCCTG AG                                               22
```

(2) INFORMATION FOR SEQ ID NO:6:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:6:

```
AGCTCGAGAA GCAGGCATCC TTG                                              23
```

(2) INFORMATION FOR SEQ ID NO:7:

(i) SEQUENCE CHARACTERISTICS:
        (A) LENGTH: 23 base pairs
        (B) TYPE: nucleic acid (C) STRANDEDNESS: single
            (D) TOPOLOGY: linear (xi) SEQUENCE DESCRIPTION: SEQ ID NO:7:

AGCTCGAGTT GAGACTGTCC TGC                                            23

(2) INFORMATION FOR SEQ ID NO:8:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (xi) SEQUENCE DESCRIPTION: SEQ ID NO:8:

AGGGTACCTT CGGGATCCTG AG                                             22

(2) INFORMATION FOR SEQ ID NO:9:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (xi) SEQUENCE DESCRIPTION: SEQ ID NO:9:

TAGGTACCTC TAGAAATCTA GCTGA                                          25

(2) INFORMATION FOR SEQ ID NO:10:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO:10:

AGCTCGAGCT TCGGGATCCT GAG                                            23

(2) INFORMATION FOR SEQ ID NO:11:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (xi) SEQUENCE DESCRIPTION: SEQ ID NO:11:

GGACCTCGAG ATCTTTTTAT GATGAC                                         26

(2) INFORMATION FOR SEQ ID NO:12:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (xi) SEQUENCE DESCRIPTION: SEQ ID NO:12:

GCGCAAGCTT GGGCTGGG                                                  18

(2) INFORMATION FOR SEQ ID NO:13:

(i) SEQUENCE CHARACTERISTICS:
            (A) LENGTH: 25 base pairs
            (B) TYPE: nucleic acid
            (C) STRANDEDNESS: single (D) TOPOLOGY: linear (xi) SEQUENCE DESCRIPTION: SEQ ID NO:13:

GGACCTCGAG GTCTCCATGA GCTAC                                                     25

(2) INFORMATION FOR SEQ ID NO:14:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (xi) SEQUENCE DESCRIPTION: SEQ ID NO:14:

GCGCAAGCTT GGGCTGGG                                                             18

(2) INFORMATION FOR SEQ ID NO:15:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (xi) SEQUENCE DESCRIPTION: SEQ ID NO:15:

TAGGTACCTC TAGAAATCTA GCTGA                                                     25

(2) INFORMATION FOR SEQ ID NO:16:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO:16:

AGCTCGAGAA GCAGGCATCC TTG                                                       23

(2) INFORMATION FOR SEQ ID NO:17:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (xi) SEQUENCE DESCRIPTION: SEQ ID NO:17:

GGACCTCGAG GTCTCCATGA GCTAC                                                     25

(2) INFORMATION FOR SEQ ID NO:18:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (xi) SEQUENCE DESCRIPTION: SEQ ID NO:18:

GCGCAAGCTT GGGCTGGG                                                             18

(2) INFORMATION FOR SEQ ID NO:19:

(i) SEQUENCE CHARACTERISTICS:
            (A) LENGTH: 25 base pairs
            (B) TYPE: nucleic acid
            (C) STRANDEDNESS: single
            (D) TOPOLOGY: linear

```
    (xi) SEQUENCE DESCRIPTION: SEQ ID NO:19:

TAGGTACCTC TAGAAATCTA GCTGA                                         25

(2) INFORMATION FOR SEQ ID NO:20:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:20:

AGCTCGAGTT GAGACTGTCC TGC                                           23

(2) INFORMATION FOR SEQ ID NO:21:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:21:

TAGGTACCTC TAGAAATCTA GCTGA                                         25

(2) INFORMATION FOR SEQ ID NO:22:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:22:

AGCTCGAGTT GAGACTGTCC TGC                                           23
```